United States Patent
Bergman et al.

(10) Patent No.: US 8,426,557 B2
(45) Date of Patent: Apr. 23, 2013

(54) IGF-1R BINDING POLYPEPTIDES AND THEIR USE

(75) Inventors: Thomas Bergman, Knivsta (SE); Anders Jarstad, Uppsala (SE); Torbjörn Gräslund, Hägersten (SE); Tove Eriksson, Nacka (SE); Andreas Jonsson, Bromma (SE); Jingjing Li, Stockholm (SE); Christofer Lendel, Farsta (SE)

(73) Assignee: Affibody AB, Solna (SE)

( * ) Notice: Subject to any disclaimer, the term of this patent is extended or adjusted under 35 U.S.C. 154(b) by 287 days.

(21) Appl. No.: 12/452,996

(22) PCT Filed: Jul. 17, 2008

(86) PCT No.: PCT/EP2008/059391
§ 371 (c)(1),
(2), (4) Date: Jun. 7, 2010

(87) PCT Pub. No.: WO2009/019117
PCT Pub. Date: Feb. 12, 2009

(65) Prior Publication Data
US 2010/0292434 A1    Nov. 18, 2010

Related U.S. Application Data

(60) Provisional application No. 60/963,223, filed on Aug. 3, 2007.

(51) Int. Cl.
*A61K 38/00* (2006.01)
*C07K 5/00* (2006.01)
*C07K 7/00* (2006.01)
*C07K 16/00* (2006.01)
*C07K 17/00* (2006.01)

(52) U.S. Cl.
USPC .......................................... 530/324; 514/1.1

(58) Field of Classification Search ........................ None
See application file for complete search history.

(56) References Cited

U.S. PATENT DOCUMENTS
2003/0236190 A1    12/2003  Pillutla et al.

FOREIGN PATENT DOCUMENTS
| WO | WO 95/19374    | 7/1995 |
| WO | WO 2005/000883 A1 | 1/2005 |
| WO | WO 2006/092338 A2 | 9/2006 |
| WO | WO 00/63243    | 10/2006 |

OTHER PUBLICATIONS

Nilsson, Björn et al., "*A synthetic IgG-binding domain based on staphylococcal protein A*", Protein Engineering, vol. 1, No. 2, pp. 107-113 (1987).

*Primary Examiner* — Marcela M Cordero Garcia
(74) *Attorney, Agent, or Firm* — Todd E. Garabedian; Wiggin and Dana LLP

(57) ABSTRACT

This invention relates to polypeptides which bind to IGF-1R and to applications of those polypeptides in medicine, veterinary medicine, diagnostics and imaging.

44 Claims, 26 Drawing Sheets

| Polypeptide | Amino acid sequence | SEQ ID NO: |
|---|---|---|
| IBM01781 | EGFYAAIEIL ALPNLNRKQS TAFITSLED | 1 |
| IBM02003 | RGFYAAIEIL SLPNLMHSQR GAFITSLID | 2 |
| IBM02998 | EKFYAAIEIL ALPNLMRKQS TAFIRSLED | 3 |
| IBM02215 | EGFYAAMEIL TLPNLMNGQR RAFISINB | 4 |
| IBM02216 | EGFYAAIEIL LLPNLMPSQW TAFTSLGD | 5 |
| IBM02986 | RGFYAALEIL VLPNLNTQQR GAFITSLSD | 6 |
| IBM02987 | EGFYAAMEIL SLPNLMHSQR GAFITSLID | 7 |
| IBM04279 | EGFYAAMEIL ALPNLMSRQS KAFINSLID | 8 |
| IBM04280 | EGFYAAVEIL GLPNLMARQR GAFITSLED | 9 |
| IBM04281 | RGFYAAMEIV TLPNLTHRQR TAFINSLED | 10 |
| IBM04282 | EGFYAAIEIL SLPNLTQKQH AAFIGSLID | 11 |
| IBM04283 | EGFYAAMEIL ALPNLMGRQR TAFIGSLID | 12 |
| IBM04284 | EGFYAAIEIL TLPNLMRPQR SAFITSIND | 13 |
| IBM04285 | RGFYAALEIL ALPNLMRRQR SAFITSLID | 14 |
| IBM04286 | EGFYAAIEIV SLPNLTERQR TAFISLDD | 15 |
| IBM04287 | EGFYAAVEIV TLPNLTKGQR AAFIGSLDD | 16 |
| IBM04288 | EGFYAALEIL TLPNLMTKQH RAFISLGD | 17 |
| IBM04289 | RGFYAAIKIV ALPNLMRRQR RAFIRSLID | 18 |
| IBM04290 | EGFYAAMEIL ALPNLMTPRQR SAFIRSLED | 19 |
| IBM04291 | EGFYAGIEIL ILPNLMREQR TAFIGSLED | 20 |
| IBM04292 | EGFYAALEIV ALPNLTSRQR AAFIRSLSD | 21 |
| IBM04293 | RGFYAAIEIL ILPNLMGSQR RAFIFSLED | 22 |
| IBM04294 | EGFYAAIEIL ALPNLMTRQR SAFISSLAD | 23 |
| IBM04295 | EGFYAALEIL VLPNLTQRQR TAFITSLPD | 24 |
| IBM04296 | EGFYAAIEIL TLPNLMRQE TAFISLED | 25 |
| IBM04297 | EGFYAAVEIL VLPNLTSRQR TAFIGSLID | 26 |
| IBM04298 | EGFYAALEIL ALPNLMHRQR GAFISSLGD | 27 |
| IBM04299 | EGFYAALEIV SLPNLMQRQR TAFISLED | 28 |
| IBM04300 | EGFYAAIEIL TLPNLMERQR GAFIGSLSD | 29 |
| IBM04301 | RGFYAALKIL ILPNLMRNQR DAFITSLGD | 30 |
| IBM04302 | EGFYAALEIL TLPNLMEROR DAFITSIND | 31 |

FIGURE 1A

| Polypeptide | Amino acid sequence | SEQ ID NO: |
|---|---|---|
| IBM04303 | EGFYAAIEIM SLPNLTRRQR SAFIGSLED | 32 |
| IBM04304 | EGFYAALEIL VLPNLMSHQR AAFIASLED | 33 |
| IBM04305 | EGFYAGIEIL TLPNLMRQR EAFIGSLND | 34 |
| IBM04306 | EGFYAAVEIL TLPNLTERQR SAFIGSLGD | 35 |
| IBM04307 | EGFYAAIEIV ALPNLTGRQR SAFIKSLGD | 36 |
| IBM04308 | EGFYAAMEIV TLPNLMERQR RAFIASLTD | 37 |
| IBM04309 | EGFYAAMEIV ALPNLMAROR TAFIGSLTD | 38 |
| IBM04310 | EGFYAAIEII TLPNLTHRQQ RAFINSLED | 39 |
| IBM04311 | EGFYAAIEIV ALPNLTERQR RAFINSLGD | 40 |
| IBM04312 | EGFYAAVEII TLPNLTENQR SAFIGSLGD | 41 |
| IBM04313 | EGFYAAIEIL TLPNLMQRQH RAFIGSLGD | 42 |
| IBM04314 | EGFYAAIEIV TLPNLNKQCR DAFISSLND | 43 |
| IBM04315 | EGFYAAIEII TLPNLNAQQR RAFIGSLHD | 44 |
| IBM04316 | EGFYAAVEIL VLPNLMKSQR DAFIGSLND | 45 |
| IBM04317 | EGFYAAMEIV ALPNLMNNQR TAFIRSLGD | 46 |
| IBM04319 | EGFYAALEIL VLPNLMRRQR SAFISSLED | 47 |
| IBM04320 | EGFYAAIEIL GLPNLMRRQR TAFIGSLTD | 48 |
| IBM04490 | EGFYAAIEIV ALPNLNRRQR SAFIGSLED | 49 |
| IBM04491 | EGFYAAIEIL SLPNLMGRQR TAFINSLED | 50 |
| IBM04492 | EGFYAAIEIL TLPNLMSGQR SAFIGSLTD | 51 |
| IBM04493 | EGFYAAIEIL TLPNLTKNQR SAFIGSLGD | 52 |
| IBM04494 | EGFYAAIEIV ALPNLMRRQR TAFITSLTD | 53 |
| IBM04495 | EGFYAAIEIV SLPNLMGRQR RAFIGSLGD | 54 |
| IBM04496 | EGFYAAIEII TLPNLMNTQR KAFITSLGD | 55 |
| IBM04497 | EGFYAALEIL ALPNLMRKQR GAFIDSLND | 56 |
| IBM04498 | EGFYAAIEIL SLPNLMKRQH RAFINSLND | 57 |
| IBM04499 | EGFYAAIEIV TLPNLMANQR TAFIGSLGD | 58 |
| IBM04500 | EGFYAAIEIV ALPNLTNRQR SAFITSLED | 59 |
| IBM04501 | EGFYAAIEIL TLPNLMRRQH EAFIASLGD | 60 |
| IBM04502 | EGFYAAMEIL VLPNLTQRQR EAFIRSLND | 61 |
| IBM04503 | EGFYAAIEIV ALPNLMSNQR TAFIRSLTD | 62 |

FIGURE 1B

| Polypeptide | Amino acid sequence | SEQ ID NO: |
|---|---|---|
| IBM04504 | EGFYAAIEIV ALPNLTPRQE AAFITRSLAD | 63 |
| IBM04505 | EGFYAALEIL SLPNLNKRQR RAFISSLED | 64 |
| IBM04506 | EGFYAAIEIV ALPNLMQQQR RAFIQSLGD | 65 |
| IBM04507 | EGFYAAVEIL ALPNLMQRQR TAFITSLSD | 66 |
| IBM04508 | EGFYAAIEIT SLPNLNRBQE GAFIASLID | 67 |
| IBM04509 | EGFYAALEIV ALPNLNSKQR RAFITSLED | 68 |
| IBM04510 | EGFYAAMEII ALPNLTQRQR TAFISSLED | 69 |
| IBM04511 | EGFYAAIEIV VLPNLMESQR SAFIRSLGD | 70 |
| IBM04512 | EGFYAAIEIL VLPNLTQSQE RAFITSLED | 71 |
| IBM04513 | EGFYAAMEIL TLPNLNKKQH RAFINSLED | 72 |
| IBM04514 | EGFYAALEIL TLPNLMRRQR TAFITSLGD | 73 |
| IBM04515 | EGFYAAMEIL VLPNLNSKQR TAFIHSLSD | 74 |
| IBM04516 | EGFYAAIEIL ALPNLNTKQE TAFIESLED | 75 |
| IBM04517 | EGFYAAMKIL TLPNLNPRQR TAFIESLTD | 76 |
| IBM04518 | EGFYAALEIL TLPNLMRQR RAFITSLDD | 77 |
| IBM04519 | EGFYAAIEIT TLPNLTHRQH TAFIRSLGD | 78 |
| IBM04520 | EGFYAAIEIV SLPNLMQRQE GAFIASLGD | 79 |
| IBM04521 | EGFYAAIKIV TLPNLNRRQR DAFIASLGD | 80 |
| IBM04522 | EGFYAAMEIL TLPNLTRKQE SAFIGSLTD | 81 |
| IBM04523 | EGFYAALEIL TLPNLMRKQH AAFINSLED | 82 |
| IBM04524 | EGFYAALEIL ILPNLNRGQH AAFIRSLTD | 83 |
| IBM04525 | EGFYAAMKII ALPNLNRKQR TAFISSLAD | 84 |
| IBM04526 | EGFYAALEIL ALPNLMTSKQR EAFIGSLGD | 85 |
| IBM04527 | EGFYASIEIL VLPNLNSRQR SAFISSLGD | 86 |
| IBM04528 | EGFYAAIEIV ALPNLMTRBQE AAFIASLDD | 87 |
| IBM04529 | EGFYAAIKIL TLPNLMQRQR GAFINSLGD | 88 |
| IBM04530 | EGFYAAIEII ALPNLMTQRQH RAFINSLED | 89 |
| IBM04531 | EGFYAAIEIV ALPNLTRKQR RAFISSLND | 90 |
| IBM04532 | EGFYAAIEIV VLPNLTTRQH KAFIGSLSD | 91 |
| IBM04533 | EGFYAAIEIL SLPNLTSRQR TAFIHSLQD | 92 |
| IBM04534 | EGFYAAIEIV ALPNLMRMRQR TAFIRSLTD | 93 |

FIGURE 1C

| Polypeptide | Amino acid sequence | SEQ ID NO: |
|---|---|---|
| IBM04535 | EGFYAAIEIT SLPMLMRKQR GAFIASLTD | 94 |
| IBM04536 | EGFYAAIEIL ILPMLNRKQS RAFIASLED | 95 |
| IBM04537 | EGFYAAMEIL SLPMLNKRQR TAFIGSLED | 96 |
| IBM04538 | EGFYAAIEIL VLPNLMQNQR GAFISLSD | 97 |
| IBM04539 | EGFYAALEIV SLPMLNRNQR GAFIASLTD | 98 |
| IBM04540 | EGFYAAMEII SLPMLTKRQR RAFITSLGD | 99 |
| IBM04541 | EGFYAAIEIV SLPMLNKRQR RAFIESLGD | 100 |
| IBM04542 | EGFYAAIEIL ALPMLTHKQR TAFIGSLED | 101 |
| IBM04543 | EGFYAAIEIL ALPMLMRRQR TAFIGSLGD | 102 |
| IBM04544 | EGFYAAIEIL TLPMLNSRQR DAFIGSLGD | 103 |
| IBM04545 | EGFYAAIEIV SLPMLTPRQR QAFIGSLGD | 104 |
| IBM04546 | EGFYAALEIV SLPMLNMRQR EAFIASLED | 105 |
| IBM04547 | EGFYAAIEIL TLPMLTQRQR TAFIRSLGD | 106 |
| IBM04548 | EGFYAAIEIV VLPNLMNKQR SAFIKSLDD | 107 |
| IBM04549 | EGFYAAIEIL TLPMLTSRQH RAFIASLED | 108 |
| IBM04550 | EGFYAAIEIV TLPMLMQRQR QAFIASLGD | 109 |
| IBM04551 | EGFYAAIEIL TLPMLTQKQR GAFIASLSD | 110 |
| IBM04552 | EGFYAAMEII ILPMLNLTPRQR AAFIASLED | 111 |
| IBM04553 | EGFYAAVEIL VLPNLMSKQR TAFIASLED | 112 |
| IBM04554 | EGFYAAIEIL GLPMLNEKQR SAFIASLED | 113 |
| IBM04555 | EGFYAAIEIV ALPMLNGGQR SAFIGSLED | 114 |
| IBM04557 | EGFYAAIEIL ALPMLTNKQR RAFIGSLND | 115 |
| IBM04558 | EGFYAAIEIL TLPMLIDRQR SAFIGSLND | 116 |
| IBM04559 | EGFYAAIEIL TLPMLNPKQR SAFIGSLED | 117 |
| IBM04560 | EGFYAAIEIL SLPMLNSRQR QAFIGSLED | 118 |
| IBM04561 | EGFYAAIEIV ILPMLNTNRQR DAFIRSLAD | 119 |
| IBM04562 | EGFYAAIEIV SLPMLMQRQR TAFISLAD | 120 |
| IBM04563 | EGFYAGIEIT ALPMLMNQR RAFISLAD | 121 |
| IBM04564 | EGFYAAIEIL SLPMLNSRQH RAFISLSD | 122 |
| IBM04565 | EGFYAALEIV SLPMLNSNQR RAFIGSLSD | 123 |
| IBM04566 | EGFYAALEIV SLPMLMHKQR NAFIGSLMD | 124 |

FIGURE 1D

| Polypeptide | Amino acid sequence | SEQ ID NO: |
|---|---|---|
| IBM04567 | EGFYAALEIV ALPNLNPRQR TAFTRSLED | 125 |
| IBM04568 | EGFYAAIKIL TLPNLNRRQR SAFIASLGD | 126 |
| IBM04569 | EGFYAALEIV QLPNLTGRQR TAFTQSLGD | 127 |
| IBM04570 | EGFYAAMEIV ALPNLMGRQR RAFIRSLED | 128 |
| IBM04571 | EGFYAAIEIV TLPNLTGNQR TAFTRSLGD | 129 |
| IBM04572 | EGFYAAIKIL TLPNLTRHQR TAFIDSLGD | 130 |
| IBM04573 | EGFYASMEIL SLPNLMGKQR TAFTSLED | 131 |
| IBM04574 | EGFYAAIEIL TLPNLNTKQR TAFIGSLGD | 132 |
| IBM04575 | EGFYAAMEIV ALPNLNRQQR TAFINSLTD | 133 |
| IBM04576 | EGFYAAIEII ILPNLTPRQR SAFIDSLED | 134 |
| IBM04577 | EGFYAAMEIL QLPMLTNRQR AAFTSSLPD | 135 |
| IBM04578 | EGFYAAIEIL VLPNLMQDQR TAFITSLTD | 136 |
| IBM04579 | EGFYAAIEIL ILPNLNSSQR TAFIGSLED | 137 |
| IBM04580 | EGFYAAIEIL ALPNLNTRQH RAFIRSLED | 138 |
| IBM04581 | EGFYAALEIL VLPNLNRKQR TAFIGSLED | 139 |
| IBM04582 | EGFYAAIEIL SLPNLTRRQR GAFIRSLED | 140 |
| IBM04583 | EGFYAAIEIL SLPNLNRFQE TAFTASLGD | 141 |
| IBM04584 | EGFYAAIKIL ALPNLNRTQR SAFIGSLAD | 142 |
| IBM04585 | EGFYAAIEIL SLPMLMFRQR TAFITSLTD | 143 |
| IBM04586 | EGFYAAIEIL VLPNLNRQR AAFIGSLED | 144 |
| IBM04587 | EGFYAAIEIL ALPNLNRKQR TAFIQSLDD | 145 |
| IBM04588 | EGFYAALKIL SLPNLTQRQH EAFIRSLGD | 146 |
| IBM04589 | EGFYAAIEII TLPNLTMMQH TAFTRSLGD | 147 |
| IBM04590 | EGFYAAIEIL TLPNLNKQH RAFIASLGD | 148 |
| IBM04591 | EGFYAAMEIV ALPNLNTSKQR CAFIGSLND | 149 |
| IBM04592 | EGFYAAIEII ILPNLMRTKQR CAFIGSLND | 150 |
| IBM04593 | EGFYAAIEIL SLPMLMBROR SAFIGSLGD | 151 |
| IBM04594 | EGFYAALEIL SLPNLNRQR SAFIGSLED | 152 |
| IBM04595 | EGFYAAIEIL TLPNLMQNQR TAFTRSLGD | 153 |
| IBM04596 | EGFYAAIEIL TLPNLNSPQR DAFISSLGD | 154 |
| IBM04597 | EGFYAAIEII TLPNLTQGQR TAFIRSLSD | 155 |

FIGURE 1E

| Polypeptide | Amino acid sequence | SEQ ID NO: |
|---|---|---|
| IBM04598 | EGFYAAMEIL ILPNLTRGQR RAFIASLGD | 156 |
| IBM04599 | EGFYAAMEIL TLPNLMQKQR DAFITSLGD | 157 |
| IBM04600 | EGFYAAMEIL TLPNLMKRQR TAFIESLTD | 158 |
| IBM04601 | EGFYAAIEII ALPNLMKRQR TAFIRSLED | 159 |
| IBM04602 | EGFYAAIEIV TLFNLTHRQR SAFIGSLGD | 160 |
| IBM04604 | EGFYAAMEIL TLPNLMTRQR TAFINSLPD | 161 |
| IBM04605 | EGFYAAIEII TLPNLMTQRQR SAFINSLGD | 162 |
| IBM04606 | EGFYAAIEII TLPNLMTGRQR TAFIRSLED | 163 |
| IBM04607 | EGFYAAIEII SLFNLMRFQR AAFIRSLED | 164 |
| IBM04608 | EGFYAAIEIV SLPNLTSKQR GAFITSLTD | 165 |
| IBM04609 | EGFYAAIEIL SLPNLMTQRQR TAFITSLED | 166 |
| IBM04610 | EGFYAAIEIL ILPNLMTQHQR TAFITSLGD | 167 |
| IBM04611 | EGFYAAIEIL TLPNLTSQQR RAFIQSLTD | 168 |
| IBM04612 | EGFYAALEII TLPNLMPKQR TAFINSLTD | 169 |
| IBM04614 | EGFYAAMEIL TLPNLNTCQR SAFIKSLED | 170 |
| IBM04615 | EGFYAAIEIL VLPNLMTRQR RAFITSLED | 171 |
| IBM04616 | EGFYAAIEIV SLPNLNTRQR SAFITSLGD | 172 |
| IBM04617 | EGFYAAIEIL VLPNLMTKQR EAFIGSLTD | 173 |
| IBM04618 | EGFYAAMEIL VLPNLMQKQR RAFIGSLGD | 174 |
| IBM04619 | EGFYAAIEIL TLPNLMTRQR SAFITSLQD | 175 |
| IBM04620 | EGFYAAIEIL SLPNLMTGRQH RAFITSLED | 176 |
| IBM04621 | EGFYAASIEIL ALPNLMRPKQR SAFIESLPD | 177 |
| IBM04623 | EGFYAAIEII VLPNLMTGRQR SAFIGSLQD | 178 |
| IBM04624 | EGFYAAIEIL TLPNLNSPQR TAFIGSLGD | 179 |
| IBM04625 | EGFYAAIEIV VLPNLMKPKQR TAFIDSLGD | 180 |
| IBM04626 | EGFYAAIEIL VLPNLMSRQR RAFIGSLQD | 181 |
| IBM04627 | EGFYAAIEIL TLPNLMSRQR RAFIGSLQD | 182 |
| IBM04628 | EGFYAAIEIL TLPNLMKRQR SAFIGSLTD | 183 |
| IBM04629 | EGFYAAIEII ILPNLMQRQR SAFIESLGD | 184 |
| IBM04630 | EGFYAAIEIL ALPNLMRPKQR SAFIRSLGD | 185 |
| IBM04631 | EGFYAALEIV ALPNLMFRKQR TAFISSLTD | 186 |

FIGURE 1F

| Polypeptide | Amino acid sequence | SEQ ID NO: |
|---|---|---|
| IBM04632 | EGFYAAMEIL GLFNLMFRQR RAFITSLID | 187 |
| IBM04633 | EGFYAAVEIL TLPNLTRRQH RAFITSLGD | 188 |
| IBM04634 | EGFYAAIEIV ALPMLTTKQR SAFIKSLGD | 189 |
| IBM04635 | EGFYAALEIL VLPNLTQNQR TAFITSLID | 190 |
| IBM04636 | EGFYAALEIT ALFNLMQKQR SAFIQSLGD | 191 |
| IBM04637 | EGFYAAIEIL VLPNLMSFQR DAFIRSLSD | 192 |
| IBM04638 | EGFYAALEIL TLPMLMQGQR DAFITSLGD | 193 |
| IBM04639 | EGFYAAMEIL HLPNLTKRQH RAFITSLED | 194 |
| IBM04640 | EGFYAALEIL SLPNLTPKQR SAFITSLID | 195 |
| IBM04641 | EGFYAAIEIV VLPNLTPRQR SAFIKSLID | 196 |
| IBM04642 | EGFYAAIEIL TLPMLMFQQR TAFIKSLED | 197 |
| Z01781 | VDNKFNKEGF YAAIEILALP NLNRKQSTAF ISSLEDDPSQ SANLLAEAKK LNDAQAPK | 198 |
| Z02003 | VDNKFNKEGF YAAIEILSLP NLMHSQRGAF ITSLTDDPSQ SANLLAEAKK LNDAQAPK | 199 |
| Z02998 | VDNKFNKEKF YAAMEILALP NLMRKQSTAF ISLEDDPSQ SANLLAEAKK LNDAQAPK | 200 |
| Z02215 | VDNKFNKEGF YAAMEILTLP NLNNGQBRAF ISLNDDPSQ SANLLAEAKK LNDAQAPK | 201 |
| Z03984 | VDNKFNKEGF YAALEILLLP NLNPSQWTAF ITSLGDDPSQ SANLLAEAKK LNDAQAPK | 202 |
| Z03085 | VDNKFNKEGF YAALEIVLIP NLMTQQRGAF ITSLSDDPSQ SANLLAEAKK LNDAQAPK | 203 |
| Z02987 | VDNKFNKEGF YAAMEISLP NLTHRQRGAF ITSLTDDPSQ SANLLAEAKK LNDAQAPK | 204 |
| Z04279 | VDNKFNKEGF YAALEILSLP NLTQKQHTAF ITSLNDDPSQ SANLLAEAKK LNDAQAPK | 205 |
| Z04280 | VDNKFNKEGF YAAMEILALP NLNGBQBSAF ITSLNDDPSQ SANLLAEAKK LNDAQAPK | 206 |
| Z04281 | VDNKFNKEGF YAALEIKILP NLMRKQRSAF ITSLEDDPSQ SANLLAEAKK LNDAQAPK | 207 |
| Z04282 | VDNKFNKEGF YAALEIVSLP NLMTKGQBEAF IGSLDDDPSQ SANLLAEAKK LNDAQAPK | 208 |
| Z04283 | VDNKFNKEGF YAAVEIVTLP NLTKGQEEAF IGSLGDDPSQ SANLLAEAKK LNDAQAPK | 209 |
| Z04284 | VDNKFNKEGF YAALEILTLP NLMRKQRSAF ITSLNDDPSQ SANLLAEAKK LNDAQAPK | 210 |
| Z04285 | VDNKFNKEGF YAALEILALP NLMRKQRTAF ISSLEDDPSQ SANLLAEAKK LNDAQAPK | 211 |
| Z04286 | VDNKFNKEGF YAALEIVSLP NLMTKQRRAF IGSLDDDPSQ SANLLAEAKK LNDAQAPK | 212 |
| Z04287 | VDNKFNKEGF YAAMEILSLP NLMTKQHRAF ITSLGDDPSQ SANLLAEAKK LNDAQAPK | 213 |
| Z04288 | VDNKFNKEGF YAALEIILLP NLMRQHRAAF ITSLGDDPSQ SANLLAEAKK LNDAQAPK | 214 |
| Z04289 | VDNKFNKEGF YAAIEIVALP NLMRRQRSAF IRSLEDDPSQ SANLLAEAKK LNDAQAPK | 215 |
| Z04290 | VDNKFNKEGF YAALEIVALP NLITPQRTAF IGSLEDDPSQ SANLLAEAKK LNDAQAPK | 216 |
| Z04291 | VDNKFNKEGF YAGIEILILP NLNEFQRAAF IRSLSDDPSQ SANLLAEAKK LNDAQAPK | 217 |

FIGURE 1G

| Polypeptide | Amino acid sequence | | | | | SEQ ID NO: |
|---|---|---|---|---|---|---|
| Z04292 | VDNKFNKEGF YAALEIVALP NLTSKQREAF IGSLGDDPSQ SANLLAEAKK LNDAQAPK | | | | | 218 |
| Z04293 | VDNKFNKEGF YAAIEILILP NLMGSQRRAF ISSLADDPSQ SANLLAEAKK LNDAQAPK | | | | | 219 |
| Z04294 | VDNKFNKEGF YAALEILLALP NLMTRQESAF ISSLFDDPSQ SANLLAEAKK LNDAQAPK | | | | | 220 |
| Z04295 | VDNKFNKEGF YAALEILVLP NLTQRQRTAF ITSLEDDPSQ SANLLAEAKK LNDAQAPK | | | | | 221 |
| Z04296 | VDNKFNKEGF YAAIEILTLP NLMNRQRTAF ITSLPDDPSQ SANLLAEAKK LNDAQAPK | | | | | 222 |
| Z04297 | VDNKFNKEGF YAAVEILVLP NLTSRQRTAF IGSLTDDPSQ SANLLAEAKK LNDAQAPK | | | | | 223 |
| Z04298 | VDNKFNKEGF YAALEILALP NLMHRQBGAF ISSLDDDPSQ SANLLAEAKK LNDAQAPK | | | | | 224 |
| Z04299 | VDNKFNKEGF YAALRIVSLP NLMQRQRTAF ITSLEDDPSQ SANLLAEAKK LNDAQAPK | | | | | 225 |
| Z04300 | VDNKFNKEGF YAAIEILTLP NLMERQRGAF IGSLGDDPSQ SANLLAEAKK LNDAQAPK | | | | | 226 |
| Z04301 | VDNKFNKEGF YAAIEILILP NLMRRQRTAF ISSLGDDPSQ SANLLAEAKK LNDAQAPK | | | | | 227 |
| Z04302 | VDNKFNKEGF YAAIEILTLP NLNRBQRDAF ITSLNDDPSQ SANLLAEAKK LNDAQAPK | | | | | 228 |
| Z04303 | VDNKFNKEGF YAAIEIMSLP NLTRKQRSAF IGSLEDDPSQ SANLLAEAKK LNDAQAPK | | | | | 229 |
| Z04304 | VDNKFNKEGF YAALEILTLP NLMSHQRAAF IASLEDDPSQ SANLLAEAKK LNDAQAPK | | | | | 230 |
| Z04305 | VDNKFNKEGF YAGLEILTLP NLMRRQREAF IGSLNDDPSQ SANLLAEAKK LNDAQAPK | | | | | 231 |
| Z04306 | VDNKFNKEGF YAALEILTLP NLTRBQESAF ISSLGDDPSQ SANLLAEAKK LNDAQAPK | | | | | 232 |
| Z04307 | VDNKFNKEGF YAAVEILTLP NLTGRQRHAF IKSLGDDPSQ SANLLAEAKK LNDAQAPK | | | | | 233 |
| Z04308 | VDNKFNKEGF YAAIKIVALP NLMERQRAAF IASLTDDPSQ SANLLAEAKK LNDAQAPK | | | | | 234 |
| Z04309 | VDNKFNKEGF YAALEIVTLP NLMARQRTAF IGSLTDDPSQ SANLLAEAKK LNDAQAPK | | | | | 235 |
| Z04310 | VDNKFNKEGF YAAMEIVALP NLMKSQRDAF IGSLNDDPSQ SANLLAEAKK LNDAQAPK | | | | | 236 |
| Z04311 | VDNKFNKEGF YAALEITLLP NLMNNQRTAF IRSLGDDPSQ SANLLAEAKK LNDAQAPK | | | | | 237 |
| Z04312 | VDNKFNKEGF YAALEIVALP NLTHRQQRAF INSLGDDPSQ SANLLAEAKK LNDAQAPK | | | | | 238 |
| Z04313 | VDNKFNKEGF YAAVEIITLP NLTEKQRSAF ISSIEDDPSQ SANLLAEAKK LNDAQAPK | | | | | 239 |
| Z04314 | VDNKFNKEGF YAALEILTLP NLMQRQHRAF ISSLGDDPSQ SANLLAEAKK LNDAQAPK | | | | | 240 |
| Z04315 | VDNKFNKEGF YAALEITTLP NLMNRQQEDAF ISSLMDDPSQ SANLLAEAKK LNDAQAPK | | | | | 241 |
| Z04316 | VDNKFNKEGF YAAIEILTLP NLMKSQRRAF IGSLMDDPSQ SANLLAEAKK LNDAQAPK | | | | | 242 |
| Z04317 | VDNKFNKEGF YAAMEIVALP NLMNNQRTAF IGSLGDDPSQ SANLLAEAKK LNDAQAPK | | | | | 243 |
| Z04319 | VDNKFNKEGF YAALEILGLP NLMRFQBTAF ISSLQDDPSQ SANLLAEAKK LNDAQAPK | | | | | 244 |
| Z04320 | VDNKFNKEGF YAALEILLLP NLMRRQRSAF ISSIEDDPSQ SANLLAEAKK LNDAQAPK | | | | | 245 |
| Z04490 | VDNKFNKEGF YAAMEILTLP NLMPGQRTAF INSLEDDPSQ SANLLAEAKK LNDAQAPK | | | | | 246 |
| Z04491 | VDNKFNKEGF YAAMEILTLP NLMSGQRSAF IRSLTDDPSQ SANLLAEAKK LNDAQAPK | | | | | 247 |
| Z04492 | VDNKFNKEGF YAAIEILTLP NLTRNQESAF IGSLGDDPSQ SANLLAEAKK LNDAQAPK | | | | | 248 |

FIGURE 1H

| Polypeptide | Amino acid sequence | SEQ ID NO: |
|---|---|---|
| Z04493 | VDNKFNKEGF YAALEIVALP NLMFRQRTAF ITSLTDDPSQ SANLLAEAKK LNDAQAPK | 249 |
| Z04494 | VDNKFNKEGF YAALEIVALP NLMRKQRSAF IRSLGDDPSQ SANLLAEAKK LNDAQAPK | 250 |
| Z04495 | VDNKFNKEGF YAAIEIVSLP NLMGEQRRAF ITSLGDDPSQ SANLLAEAKK LNDAQAPK | 251 |
| Z04496 | VDNKFNKEGF YAALEIVTLP NLMNTQRKAF ITSLGDDPSQ SANLLAEAKK LNDAQAPK | 252 |
| Z04497 | VDNKFNKEGF YAALEIVALP NLMRKQRGAF IDSINDDPSQ SANLLAEAKK LNDAQAPK | 253 |
| Z04498 | VDNKFNKEGF YAAIEILSLP NLMSKQHRAF INSITDDPSQ SANLLAEAKK LNDAQAPK | 254 |
| Z04499 | VDNKFNKEGF YAALEILTLP NLMNANQETAF IGSLGDDPSQ SANLLAEAKK LNDAQAPK | 255 |
| Z04500 | VDNKFNKEGF YAALEIVALP NLTNKRQRSAF ITSLEDDPSQ SANLLAEAKK LNDAQAPK | 256 |
| Z04501 | VDNKFNKEGF YAALEILTLP NLMRRQHEAF IASLGDDPSQ SANLLAEAKK LNDAQAPK | 257 |
| Z04502 | VDNKFNKEGF YAAMEILVLP NLTQRQREAF ITSINDDPSQ SANLLAEAKK LNDAQAPK | 258 |
| Z04503 | VDNKFNKEGF YAALEIISLP NLMSNQETAF IRSLTDDPSQ SANLLAEAKK LNDAQAPK | 259 |
| Z04504 | VDNKFNKEGF YAALEIVALP NLTPRQNAAF IRSLADDPSQ SANLLAEAKK LNDAQAPK | 260 |
| Z04505 | VDNKFNKEGF YAALEITLP NLMKHQRRAF ISSLEDDPSQ SANLLAEAKK LNDAQAPK | 261 |
| Z04506 | VDNKFNKEGF YAALEIVALP NLMESQRRAF IQSLGDDPSQ SANLLAEAKK LNDAQAPK | 262 |
| Z04507 | VDNKFNKEGF YAAVEILALP NLMNRRQRTAF ITSLSDDPSQ SANLLAEAKK LNDAQAPK | 263 |
| Z04508 | VDNKFNKEGF YAALEIISLP NLMRKQRGAF IASLITDDPSQ SANLLAEAKK LNDAQAPK | 264 |
| Z04509 | VDNKFNKEGF YAALEIVALP NLMSKQRRAF ITSLEDDPSQ SANLLAEAKK LNDAQAPK | 265 |
| Z04510 | VDNKFNKEGF YAAMEITALP NLTQRQRTAF IRSLEDDPSQ SANLLAEAKK LNDAQAPK | 266 |
| Z04511 | VDNKFNKEGF YAALEILVLP NLMSEQENAF IKSLGDDPSQ SANLLAEAKK LNDAQAPK | 267 |
| Z04512 | VDNKFNKEGF YAAIEILALP NLMTKQRTAF INSLEDDPSQ SANLLAEAKK LNDAQAPK | 268 |
| Z04513 | VDNKFNKEGF YAAMEILTLP NLMFRQRTAF IESLITDDPSQ SANLLAEAKK LNDAQAPK | 269 |
| Z04514 | VDNKFNKEGF YAALEIISLP NLMKKQRRAF INSLEDDPSQ SANLLAEAKK LNDAQAPK | 270 |
| Z04515 | VDNKFNKEGF YAALEITTLP NLMKQRQRIAF ITSLGDDPSQ SANLLAEAKK LNDAQAPK | 271 |
| Z04516 | VDNKFNKEGF YAAIEHLSLP NLMNSEQENAF IHSLSDDPSQ SANLLAEAKK LNDAQAPK | 272 |
| Z04517 | VDNKFNKEGF YAALEIVTLP NLMLMRQRDAF IASLGDDPSQ SANLLAEAKK LNDAQAPK | 273 |
| Z04518 | VDNKFNKEGF YAAMEILTLP NLMFRQRRAF IESLITDDPSQ SANLLAEAKK LNDAQAPK | 274 |
| Z04519 | VDNKFNKEGF YAALEILTLP NLMNTQRTAF ITSLDDDPSQ SANLLAEAKK LNDAQAPK | 275 |
| Z04520 | VDNKFNKEGF YAAIEILTLP NLMKQRQRGAF IRSLGDDPSQ SANLLAEAKK LNDAQAPK | 276 |
| Z04521 | VDNKFNKEGF YAALEIVTLP NLMKRQRSAF IASLGDDPSQ SANLLAEAKK LNDAQAPK | 277 |
| Z04522 | VDNKFNKEGF YAAMEILILP NLMHQRSRAF IGSITDDPSQ SANLLAEAKK LNDAQAPK | 278 |
| Z04523 | VDNKFNKEGF YAALEITILP NLTHRQHAAF INSLEDDPSQ SANLLAEAKK LNDAQAPK | 279 |

FIGURE 11

| Polypeptide | Amino acid sequence | SEQ ID NO: |
|---|---|---|
| Z04524 | VDNKFNKEGF YAALEILILP NLMEGQHAAF IRSLIDDPSQ SAMLLAEAKK LNDAQAPK | 280 |
| Z04525 | VDNKFNKEGF YAAMEITALP NLTKGRTAF ISSLANDPSQ SAMLLAEAKK LNDAQAPK | 281 |
| Z04526 | VDNKFNKEGF YAALEILALP NLTSKQBEAF IGSLGDDPSQ SAMLLAEAKK LNDAQAPK | 282 |
| Z04527 | VDNKFNKEGF YASIEILVLP NLMSKQRSAF ISSLGDDPSQ SAMLLAEAKK LNDAQAPK | 283 |
| Z04528 | VDNKFNKEGF YAALEIVALP NLTKRQRAAF IASLEDDPSQ SAMLLAEAKK LNDAQAPK | 284 |
| Z04529 | VDNKFNKEGF YAALEITLP NLMQRQRGAF INSLEDDPSQ SAMLLAEAKK LNDAQAPK | 285 |
| Z04530 | VDNKFNKEGF YAALEITALP NLTQRQHRAF ITSLMDDPSQ SAMLLAEAKK LNDAQAPK | 286 |
| Z04531 | VDNKFNKEGF YAALEIITLP NLTKKQRAAF IGSLSDDPSQ SAMLLAEAKK LNDAQAPK | 287 |
| Z04532 | VDNKFNKEGF YAALEILILP NLTRQHKAF INSLGDDPSQ SAMLLAEAKK LNDAQAPK | 288 |
| Z04533 | VDNKFNKEGF YAAIEIVSLP NLTSKQRTAF IHSLGDDPSQ SAMLLAEAKK LNDAQAPK | 289 |
| Z04534 | VDNKFNKEGF YAALEIVALP NLRNQETAF IRSLTDDPSQ SAMLLAEAKK LNDAQAPK | 290 |
| Z04535 | VDNKFNKEGF YAALEIISLP NLRRKQRGAF IASLTDDPSQ SAMLLAEAKK LNDAQAPK | 291 |
| Z04536 | VDNKFNKEGF YAALEILILP NLMPKQSRAF IASLEDDPSQ SAMLLAEAKK LNDAQAPK | 292 |
| Z04537 | VDNKFNKEGF YAAMEILSLP NLMKRQRTAF ITSLKDDPSQ SAMLLAEAKK LNDAQAPK | 293 |
| Z04538 | VDNKFNKEGF YAALEILTLP NLMQHQEGAF ISSLSDDPSQ SAMLLAEAKK LNDAQAPK | 294 |
| Z04539 | VDNKFNKEGF YAALEIVSLP NLMRPNQRGAF IQSLTDDPSQ SAMLLAEAKK LNDAQAPK | 295 |
| Z04540 | VDNKFNKEGF YAAMEIISLP NLMSRQRDAF ITSLGDDPSQ SAMLLAEAKK LNDAQAPK | 296 |
| Z04541 | VDNKFNKEGF YAALEIVALP NLTRKQRGAF IGSLGDDPSQ SAMLLAEAKK LNDAQAPK | 297 |
| Z04542 | VDNKFNKEGF YAALEILALP NLMHEQETAF IESLGDDPSQ SAMLLAEAKK LNDAQAPK | 298 |
| Z04543 | VDNKFNKEGF YAALEILSLP NLMRKQRGAF ISSLGDDPSQ SAMLLAEAKK LNDAQAPK | 299 |
| Z04544 | VDNKFNKEGF YAALEITILP NLMSRQRDAF IGSLGDDPSQ SAMLLAEAKK LNDAQAPK | 300 |
| Z04545 | VDNKFNKEGF YAALEIVSLP NLTPRQRGAF ISSIGDDPSQ SAMLLAEAKK LNDAQAPK | 301 |
| Z04546 | VDNKFNKEGF YAAIEIVSLP NLMRQBEQAF ITSLEDDPSQ SAMLLAEAKK LNDAQAPK | 302 |
| Z04547 | VDNKFNKEGF YAALEITILP NLTGRQRTAF IRSLGDDPSQ SAMLLAEAKK LNDAQAPK | 303 |
| Z04548 | VDNKFNKEGF YAALEILSLP NLMRKQRSAF IKSLDDDPSQ SAMLLAEAKK LNDAQAPK | 304 |
| Z04549 | VDNKFNKEGF YAALEIITLP NLTSROHRAF IASLGDDPSQ SAMLLAEAKK LNDAQAPK | 305 |
| Z04550 | VDNKFNKEGF YAALEITALP NLMKQEQAF IASLEDDPSQ SAMLLAEAKK LNDAQAPK | 306 |
| Z04551 | VDNKFNKEGF YAALEIVLP NLTQKQRGAF IASLSDDPSQ SAMLLAEAKK LNDAQAPK | 307 |
| Z04552 | VDNKFNKEGF YAAMEIIILP NLTPRQRAAF ITSLEDDPSQ SAMLLAEAKK LNDAQAPK | 308 |
| Z04553 | VDNKFNKEGF YAAIEILVLP NLMSRQRTAF IASLSDDPSQ SAMLLAEAKK LNDAQAPK | 309 |
| Z04554 | VDNKFNKEGF YAAVEILGLP NLRRKQBSAF IASLDDDPSQ SAMLLAEAKK LNDAQAPK | 310 |

FIGURE 1J

| Polypeptide | Amino acid sequence | | | | | SEQ ID NO: |
|---|---|---|---|---|---|---|
| Z04555 | VDNKFNKEGF | YAALEILALP | NLMGGQRSAF | IRSLEDDPSQ | SANLLAEAKK LNDAQAPK | 311 |
| Z04557 | VDNKFNKEGF | YAAIEILTLP | NLMENKQRRAF | IGSLEDDPSQ | SANLLAEAKK LNDAQAPK | 312 |
| Z04558 | VDNKFNKEGF | YAALEILILP | NLMNDRQERAF | IGSLNDDPSQ | SANLLAEAKK LNDAQAPK | 313 |
| Z04559 | VDNKFNKEGF | YAALEITVTLP | NLMPKQRSAF | ISSLSDDPSQ | SANLLAEAKK LNDAQAPK | 314 |
| Z04560 | VDNKFNKEGF | YAAIEILSLP | NLMSRQRQAF | IGSLEDDPSQ | SANLLAEAKK LNDAQAPK | 315 |
| Z04561 | VDNKFNKEGF | YAAIEIVILP | NLMLRTQRTAF | IRSLADDPSQ | SANLLAEAKK LNDAQAPK | 316 |
| Z04562 | VDNKFNKEGF | YAALEIIIALP | NLMQFQETAF | ISSLADDPSQ | SANLLAEAKK LNDAQAPK | 317 |
| Z04563 | VDNKFNKEGF | YAGIEILIALP | NLMQHQREAF | IKSLNDDPSQ | SANLLAEAKK LNDAQAPK | 318 |
| Z04564 | VDNKFNKEGF | YAALEITSLP | NLEMSRQHRAF | TTSLADDPSQ | SANLLAEAKK LNDAQAPK | 319 |
| Z04565 | VDNKFNKEGF | YAALEIVSLP | NLEMSRQRTAF | TTSLSBDDPSQ | SANLLAEAKK LNDAQAPK | 320 |
| Z04566 | VDNKFNKEGF | YALIEIVSLP | NLEHMKQEMAF | TRSLNDDPSQ | SANLLAEAKK LNDAQAPK | 321 |
| Z04567 | VDNKFNKEGF | YAALEIVALP | NLMPKQRTAF | TRSLEDDPSQ | SANLLAEAKK LNDAQAPK | 322 |
| Z04568 | VDNKFNKEGF | YAAIEILILTLP | NLMPRQRSAF | IASLGDDPSQ | SANLLAEAKK LNDAQAPK | 323 |
| Z04569 | VDNKFNKEGF | YAAIEIVGLP | NLMTGQRTAF | IQSLGDDPSQ | SANLLAEAKK LNDAQAPK | 324 |
| Z04570 | VDNKFNKEGF | YAAMEIVALP | NLMGBQERAF | TRSLGDDPSQ | SANLLAEAKK LNDAQAPK | 325 |
| Z04571 | VDNKFNKEGF | YAAIEIVILP | NLIGNQRTAF | IRSLGDDPSQ | SANLLAEAKK LNDAQAPK | 326 |
| Z04572 | VDNKFNKEGF | YAAIEILILP | NLMTRHQRTAF | IDSLGDDPSQ | SANLLAEAKK LNDAQAPK | 327 |
| Z04573 | VDNKFNKEGF | YASMEILSLP | NLMGCKQRTAF | TTSLEDDPSQ | SANLLAEAKK LNDAQAPK | 328 |
| Z04574 | VDNKFNKEGF | YAALEILTLP | NLMTKQETAF | IGSLGDDPSQ | SANLLAEAKK LNDAQAPK | 329 |
| Z04575 | VDNKFNKEGF | YAAMEIVALP | NLMRQQRTAF | INSLITDDPSQ | SANLLAEAKK LNDAQAPK | 330 |
| Z04576 | VDNKFNKEGF | YAAIEIIILP | NLTPRQRSAF | IDSLEDDPSQ | SANLLAEAKK LNDAQAPK | 331 |
| Z04577 | VDNKFNKEGF | YAAMEILQLP | NLMTNKQRAAF | ISSLPDDPSQ | SANLLAEAKK LNDAQAPK | 332 |
| Z04578 | VDNKFNKEGF | YAAIEILVLP | NLMQDQETAF | TTSLTDDPSQ | SANLLAEAKK LNDAQAPK | 333 |
| Z04579 | VDNKFNKEGF | YAALEIILTLP | NLMSSQRTAF | IGSLEDDPSQ | SANLLAEAKK LNDAQAPK | 334 |
| Z04580 | VDNKFNKEGF | YAAIEILILP | NLMTWKQRRAF | IRSLTDDPSQ | SANLLAEAKK LNDAQAPK | 335 |
| Z04581 | VDNKFNKEGF | YAALEIVLVLP | NLMMHKQRTAF | TRSLEDDPSQ | SANLLAEAKK LNDAQAPK | 336 |
| Z04582 | VDNKFNKEGF | YAAIEILSLP | NLMTREQEGAF | TTSLEDDPSQ | SANLLAEAKK LNDAQAPK | 337 |
| Z04583 | VDNKFNKEGF | YAAIEILTLP | NLMAKQRTAF | IASLGDDPSQ | SANLLAEAKK LNDAQAPK | 338 |
| Z04584 | VDNKFNKEGF | YAALEIILTLP | NLMRTQRSAF | IGSLADDPSQ | SANLLAEAKK LNDAQAPK | 339 |
| Z04585 | VDNKFNKEGF | YAAIEIISLP | NLMNPQRTAF | TTSLITDDPSQ | SANLLAEAKK LNDAQAPK | 340 |
| Z04586 | VDNKFNKEGF | YAAIEILVLP | NLMNKFQEAAF | IGSLEDDPSQ | SANLLAEAKK LNDAQAPK | 341 |

FIGURE 1K

| Polypeptide | Amino acid sequence | | | | | | SEQ ID NO: |
|---|---|---|---|---|---|---|---|
| Z04587 | VDNKFNKEGF | YAAIEILALP | NLMKQRTAF | IQSLDDDPSQ | SANLLAEAKK | LNDAQAPK | 342 |
| Z04588 | VDNKFNKKGF | YAAIEILSLP | NLTQRQHEAF | IRSLGDDPSQ | SANLLAEAKK | LNDAQAPK | 343 |
| Z04589 | VDNKFNKEGF | YAAIELTLP | NLTQNQHTAF | IRSLGDDPSQ | SANLLAEAKK | LNDAQAPK | 344 |
| Z04590 | VDNKFNKEGF | YAAIEKTLP | NLWQKQRAF | IASLGDDPSQ | SANLLAEAKK | LNDAQAPK | 345 |
| Z04591 | VDNKFNKEGF | YAAMETVALP | NLTSKQRTAF | IRSLGDDPSQ | SANLLAEAKK | LNDAQAPK | 346 |
| Z04592 | VDNKFNKEGF | YAAIEILLP | NLMTRQRGAF | IGSINDDPSQ | SANLLAEAKK | LNDAQAPK | 347 |
| Z04593 | VDNKFNKEGF | YAAIEILSLP | NLMREQSAF | ISSLGDDPSQ | SANLLAEAKK | LNDAQAPK | 348 |
| Z04594 | VDNKFNKEGF | YAALRILSLP | NLTKQRTAF | IRSLGDDPSQ | SANLLAEAKK | LNDAQAPK | 349 |
| Z04595 | VDNKFNKEGF | YAAIEILTLP | NLMQNQRSAF | IRSLGDDPSQ | SANLLAEAKK | LNDAQAPK | 350 |
| Z04596 | VDNKFNKEGF | YAAIEILTLP | NLMSPQRDAF | ISSLGDDPSQ | SANLLAEAKK | LNDAQAPK | 351 |
| Z04597 | VDNKFNKEGF | YAAIEITLP | NLTQGQRTAF | IRSLSDDPSQ | SANLLAEAKK | LNDAQAPK | 352 |
| Z04598 | VDNKFNKEGF | YAAMEILLP | NLTGRQRRAF | IASLGDDPSQ | SANLLAEAKK | LNDAQAPK | 353 |
| Z04599 | VDNKFNKEGF | YAAIEILIP | NLMQKQRDAF | ITSLGDDPSQ | SANLLAEAKK | LNDAQAPK | 354 |
| Z04600 | VDNKFNKEGF | YAAIEITLP | NLMKRQRTAF | IESLTDDPSQ | SANLLAEAKK | LNDAQAPK | 355 |
| Z04601 | VDNKFNKEGF | YAAIEITALP | NLTRBQHTAF | ITSLEDDPSQ | SANLLAEAKK | LNDAQAPK | 356 |
| Z04602 | VDNKFNKEGF | YAAIEIVTLP | NLTHRQRGAF | IRSLGDDPSQ | SANLLAEAKK | LNDAQAPK | 357 |
| Z04604 | VDNKFNKEGF | YAAMEILLP | NLMQRQRTAF | IASLGDDPSQ | SANLLAEAKK | LNDAQAPK | 358 |
| Z04605 | VDNKFNKEGF | YAALEITLP | NLTQRQRTAF | INSLPRDPSQ | SANLLAEAKK | LNDAQAPK | 359 |
| Z04606 | VDNKFNKEGF | YAALEIILP | NLTGRQRTAF | IRSLEDDPSQ | SANLLAEAKK | LNDAQAPK | 360 |
| Z04607 | VDNKFNKEGF | YAAIEHISLP | NLTRRQRAAF | IRSLEDDPSQ | SANLLAEAKK | LNDAQAPK | 361 |
| Z04608 | VDNKFNKEGF | YAAIEIVSLP | NLTSKQRGAF | ITSLTDDPSQ | SANLLAEAKK | LNDAQAPK | 362 |
| Z04609 | VDNKFNKEGF | YAALEIILP | NLMTQRQRTAF | ITSLEDDPSQ | SANLLAEAKK | LNDAQAPK | 363 |
| Z04610 | VDNKFNKEGF | YAALEIITLP | NLMTQRSAF | ITSLGDDPSQ | SANLLAEAKK | LNDAQAPK | 364 |
| Z04611 | VDNKFNKEGF | YAALEIVLP | NLTSQQRAF | INSLGDDPSQ | SANLLAEAKK | LNDAQAPK | 365 |
| Z04612 | VDNKFNKEGF | YAALRIIILLP | NLMFRQRTAF | IRSLGDDPSQ | SANLLAEAKK | LNDAQAPK | 366 |
| Z04614 | VDNKFNKEGF | YAALETVSLP | NLMKRQRSAF | IRSLGDDPSQ | SANLLAEAKK | LNDAQAPK | 367 |
| Z04615 | VDNKFNKEGF | YAAIEILVLP | NLMNTQQBRAF | ITSLEDDPSQ | SANLLAEAKK | LNDAQAPK | 368 |
| Z04616 | VDNKFNKEGF | YAALRTVSLP | NLMMTRQRSAF | ITSLGDDPSQ | SANLLAEAKK | LNDAQAPK | 369 |
| Z04617 | VDNKFNKEGF | YAAMEILVLP | NLMKQRQRTAF | ISSLTDDPSQ | SANLLAEAKK | LNDAQAPK | 370 |
| Z04618 | VDNKFNKEGF | YAAIEILVLP | NLMQKQRRAF | INSLGDDPSQ | SANLLAEAKK | LNDAQAPK | 371 |
| Z04619 | VDNKFNKEGF | YAAIEILTLP | NLTRRQSSAF | ITSLQDDPSQ | SANLLAEAKK | LNDAQAPK | 372 |

FIGURE 1L

| Polypeptide | Amino acid sequence | SEQ ID NO: |
|---|---|---|
| Z04620 | VDNKFNKEQQ NAFYEILHLP NLTGRQRAF ITSLEDDPSQ SANLLAEAKK LNDAQAPK | 373 |
| Z04621 | VDNKFNKEGF YAALEHIALP NLMRKQRSAF IRSLQDDPSQ SANLLAEAKK LNDAQAPK | 374 |
| Z04623 | VDNKFNKEGF YAALEIVLP NLTGRQEKAF IESLPDDPSQ SANLLAEAKK LNDAQAPK | 375 |
| Z04624 | VDNKFNKEGF YAAIEILTLP NLNSKQRTAF IGSLGDDPSQ SANLLAEAKK LNDAQAPK | 376 |
| Z04625 | VDNKFNKEGF YAALEIVLP NLNPKQRTAF IDSLSDDPSQ SANLLAEAKK LNDAQAPK | 377 |
| Z04626 | VDNKFNKEGF YASIEIVLP NLMGRQRTAF ITSLADDPSQ SANLLAEAKK LNDAQAPK | 378 |
| Z04627 | VDNKFNKEGF YAAIETLTLP NLNSFQRRAF IGSLQDDPSQ SANLLAEAKK LNDAQAPK | 379 |
| Z04628 | VDNKFNKEGF YAAMELTLP NLWRKQRSAF ITSLTDDPSQ SANLLAEAKK LNDAQAPK | 380 |
| Z04629 | VDNKFNKEGF YAAIETLIP NLWRQQRSAF IGSLTDDPSQ SANLLAEAKK LNDAQAPK | 381 |
| Z04630 | VDNKFNKEGF YAAIEHALP NLNRKQRSAF INSLGDDPSQ SANLLAEAKK LNDAQAPK | 382 |
| Z04631 | VDNKFNKEGF YAALEIVALP NLNRKQRTAF ISSLTDDPSQ SANLLAEAKK LNDAQAPK | 383 |
| Z04632 | VDNKFNKEGF YAAMETLGLP NLWNRQRAF ITSLGDDPSQ SANLLAEAKK LNDAQAPK | 384 |
| Z04633 | VDNKFNKEGF YAAVEITILP NLNBRQRTAF ITSLSDDPSQ SANLLAEAKK LNDAQAPK | 385 |
| Z04634 | VDNKFNKEGF YAALEIVALP NLTTKQRSAF IRSLGDDPSQ SANLLAEAKK LNDAQAPK | 386 |
| Z04635 | VDNKFNKEGF YAAIETLSLP NLTGNQRTAF ITSLQDDPSQ SANLLAEAKK LNDAQAPK | 387 |
| Z04636 | VDNKFNKEGF YAAIEIIALP NLNWQKQRSAF IQSLGDDPSQ SANLLAEAKK LNDAQAPK | 388 |
| Z04637 | VDNKFNKEGF YAAIETLTLP NLNSPQRSAF IRSLSDDPSQ SANLLAEAKK LNDAQAPK | 389 |
| Z04638 | VDNKFNKEGF YAALEIVVLP NLNGQRDAF ITSLEDDPSQ SANLLAEAKK LNDAQAPK | 390 |
| Z04639 | VDNKFNKEGF YAALEIILP NLNQRQRAF ITSLGDDPSQ SANLLAEAKK LNDAQAPK | 391 |
| Z04640 | VDNKFNKEGF YAAMEILLP NLTRPQRHAF ITSLEDDPSQ SANLLAEAKK LNDAQAPK | 392 |
| Z04641 | VDNKFNKEGF YAAIETLSLP NLTPKQRSAF ITSLTDDPSQ SANLLAEAKK LNDAQAPK | 393 |
| Z04642 | VDNKFNKEGF YAAIETLVLP NLTPQRSAF IKSLDDDPSQ SANLLAEAKK LNDAQAPK | 394 |
| Z00000 | VDNKFNKEGF YAAIEILTLP NLNPQRTAF INSLEDDPSQ SANLLAEAKK LNDAQAPK | 395 |
| IGF1R | MKSGSGGGSP TSLWGLFLS AALSLWPTSG EICGPGIDIR MDYQCLKRIE MCTVIEGYLH | 396 |
| | ILLISKAEDY RSYRPKLTV ITEYILLFRV AGLESLGDLF PNLTVIRGWK LFYNYALVTF | |
| | EMTMLKDIGL YMLRNITRGA IRIERNADLC VLSTVDWSLI LDAVSNNYIV GNKFPKECGD | |
| | LCTGTMEEKP MCEKTTINNE YNYRCWTTNR CQRMCPSTCG KRACTENNEC CHPECLGSCS | |
| | APDNDTACVA CRHYYYAGVC VPACPPNTYR FEGWRCVDRD FCANILSAES SDSEGFVIBD | |
| | GECMQECPSG FIRNGSQSMY CIPCEGPCPK VCEEEKKTKT IDSVTSAQML QGCTIFKGNL | |
| | LINIRRGNWT ASELENFMGL IEVTGYVKI RHSHALVSLS FLKMLRLILG EEQLEGNYSF | |
| | YVLDNQMLCQ LWDWDHRNLT IRAGKMYFAF NPKLCVSEIY RMEEVTGTKG RQSKGDIWTR | |

FIGURE 1M

| Polypeptide | Amino acid sequence | SEQ ID NO: |
|---|---|---|
| EGF1R ectodomain | MNGERASCES DVLHFTSTIT SKMRIIITWH RYRPPDYRDL ISFTVYKEA PFKNVTEYDG QDACGSNSWN MVDVDLPPNK DVEPGILHG LKPWTQYAVY VKAVTLMVE MDHIRGAKSE ILYIRTNASV PSIPLDVLSA SNSSQLIVK WNPPSLPNGN LSYYIVRMQR QPQDGYLYRH MYCSKDKIPI RKYADGTIDI EEVTENPKTE VCGGEKGPCC ACPKTEAEKQ AEKEEAEYRK VFENFLHNSI FVPRPERKRR DVMQVANITM SSRSRMTTAA DTYNITDPEE LETEYPFFES RVDNKERTVI SMLRPFTLYR EKLGCSASNF VFARTMPAEG ADDIPGPVTW ADDIPGPVTW BRPENSIPL KWPEPENPNG LILMZEIKYG SRQEYRKYGG SROEYRKYGG AKLNRLMPGN YTARIQATSL SGNGSWTDPV FFYVQANTGY ENFIHLIAL PVAVLLIVGG LVIMLYVFHR KRNNSRLGNG VLYASVNFFY FSAADVYVPD EWEVAREKIT MSRELGQGSF GMVYEGVAKG VYKDEPETRV AIKTVNEAAS MRERIEFLNE ASVMKEFNCH HVVRLLGVVS QGQFTLVIME LMTRGDLKSY LRSLRPEMEM MPVLAPPSLS KMIQMAGEIA DGMAYLNAMK FVHRDLAARN CMVAEDFTVK IGDFGMTRDI YETDYYRKGG KGLLPVRWMS PESLKDGVFT TYSDVWSFGV VLMELATLAE QPYQGLSNEQ VLRFVMEGGL LDKPDNCPDM LFELMRMCWQ YNPKMRPSFL EIISSIKERM EPGFREVSFY YSEEMKLPEP EELDLEPENM ESVFLDPSAS SSSLPLPDRH SGHKAENGPG PGVLVLRASF DERQPYAHMN GGRKMERALP LPQSSTC | |
| | EHCGPGIDIR MDYQQLKRLE NCTVIEGYLH ILLISKAEDY RSYRFPKLTV ITEYLLFRV AGLESLGDLF PNLTVIRGWN LFYNIALVIF EMTNLRDIGL YMLRNITRGA IRIEKNADLC YLSTVDWSLI LDAVSNNIIV GNKPEKECGD LCPGTMEEKP MCEKTTINNE YNIECWTINR COKMCPSTCG KRACTENNEC CHFECLGSCS APDNDTACVA CRHYYAGVC VPACPPNTYR FEGWRCVDRD FCANILSAES SDSEGFVIHD GECMQECPSG FIRNGSQSMY CIPCEGPCPK VCEEEKKTKT IDSVTSAQML QGCTIFKGNL LINIRRGMNI ASELENFMGI IEVVTGYVKI RHSHALVSLS FLKNLRLILG EEQLEGNYSF YVLDMQMLQQ LMDWDHRMLT IKAGKMYFAF NPKLCVSEIY BMEEVTGTKG ROSKGDIWTR NNGERASCES DVLHFTSTIT SKNRIIITWH RYRPPDYRDL ISFTVYKEA PFKNVTEYDG QDACGSNSWN MVDVDLPPNK DVEPGILHG LKPWTQYAVY VKAVTLMVE MDHIRGAKSE ILYIRTNASV PSIPLDVLSA SNSSQLIVK WNPPSLPNGN LSYYIVRMQR QPQDGYLYRH MYCSKDKIPI RKYADGTIDI EEVTENPKTE VCGGEKGPCC ACPKTEAEKQ AEKEEAEYRK VFENFLHNSI FVPRPERKRR DVMQVANTTM SSRSRMTTAA DTYNITDPEE LETEYPFFES RVDNKERTVI SMLRPFTLYR IDIHSCNHEA EKLGCSASNF VFARTMPAEG ADDIPGPVTW LILMYEIKYG SRQEYRKYGG AKLNSRLMPGN YTARIQATSL SGNGSWTDPV FFYVQAKTGY B | 397 |

FIGURE 1N

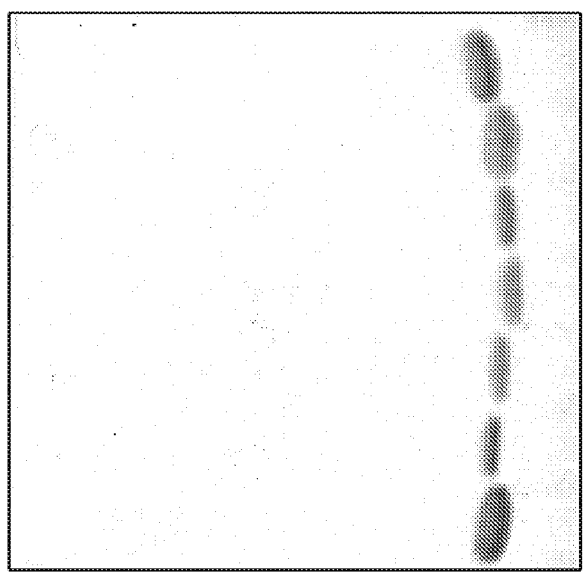
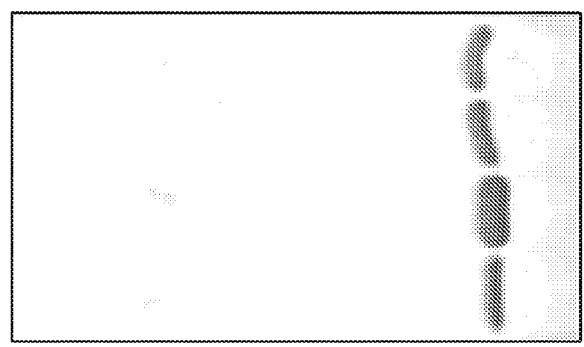
FIGURE 2

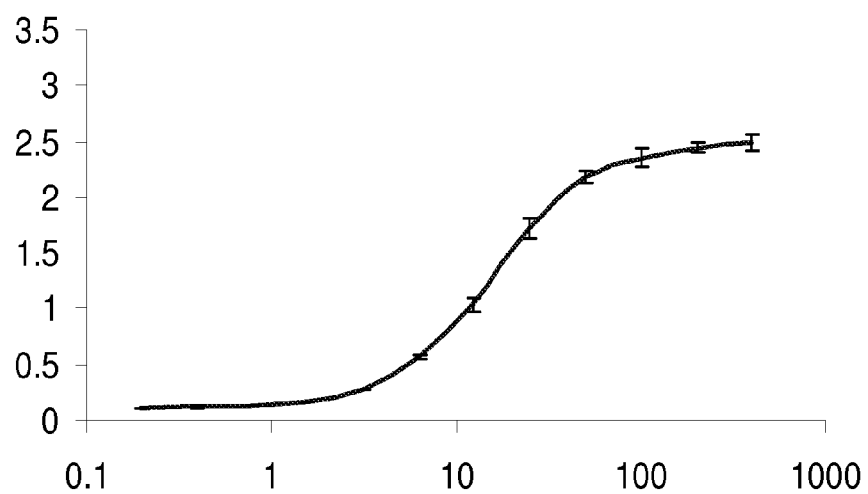
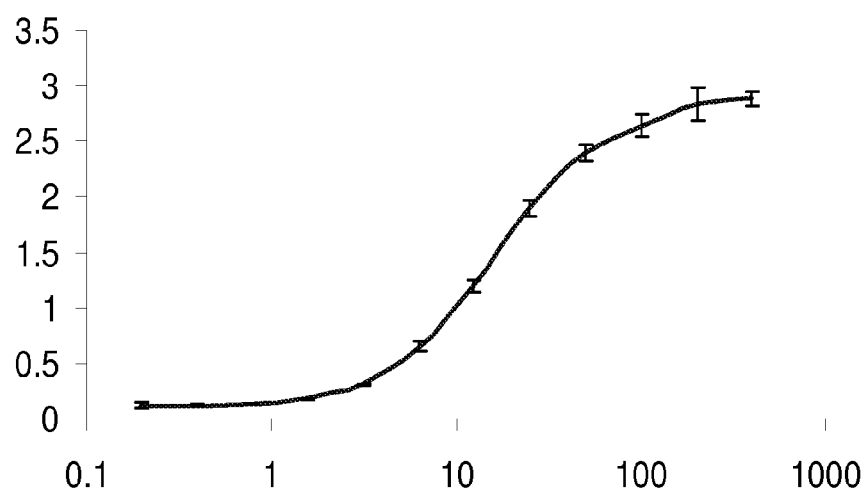
FIGURE 8A

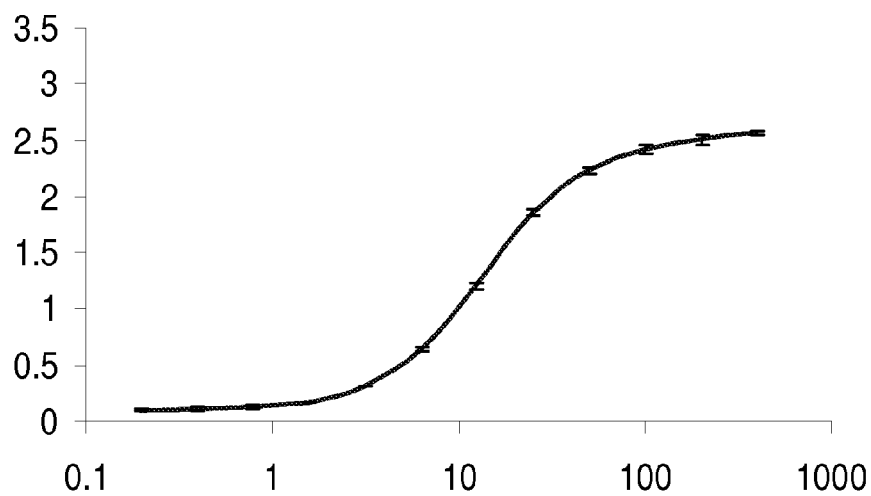
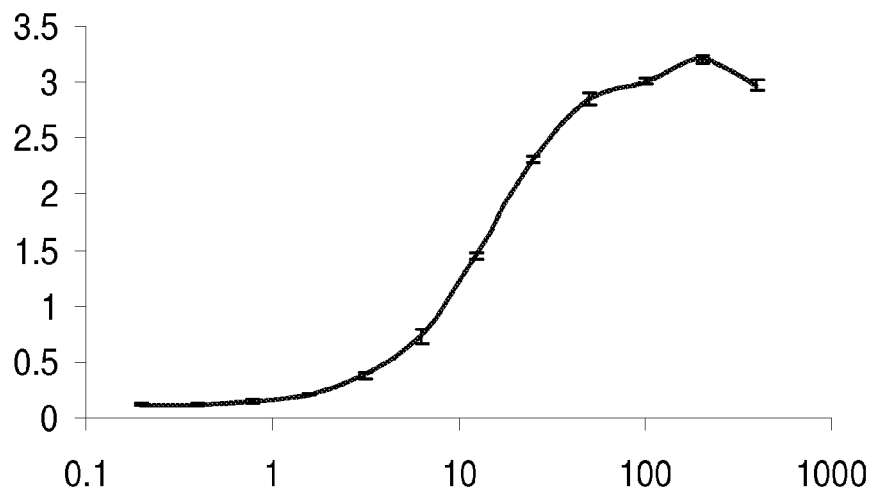
FIGURE 8B

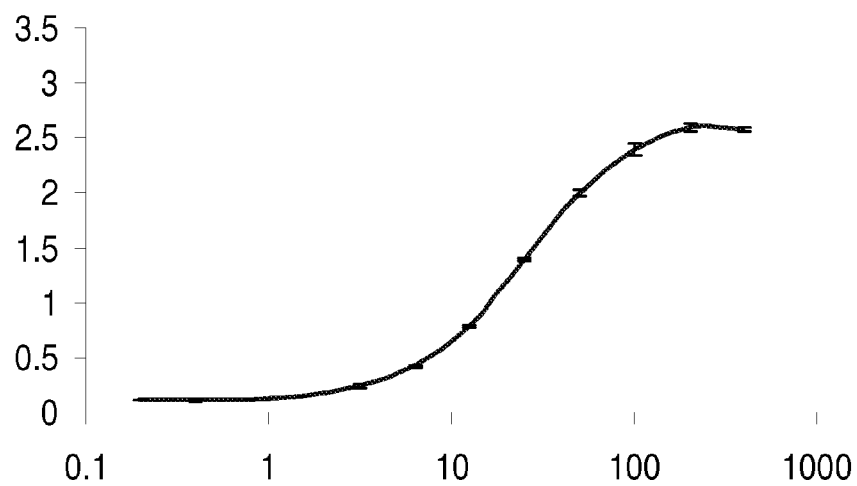
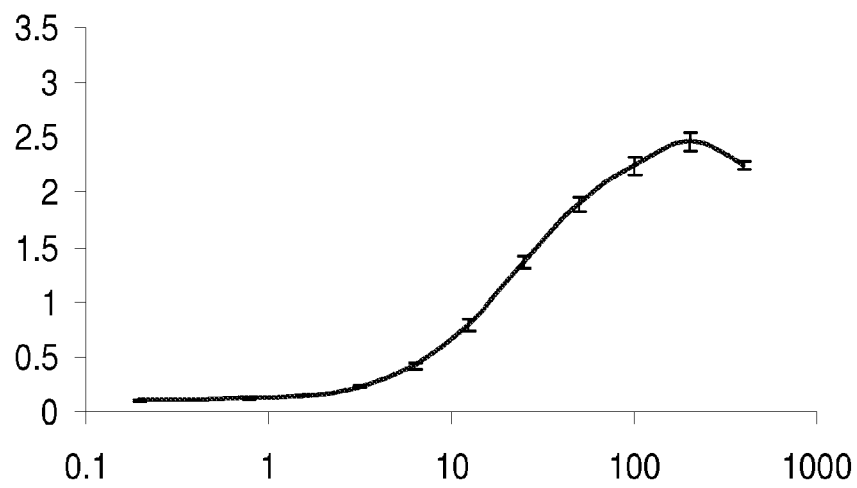
FIGURE 8C

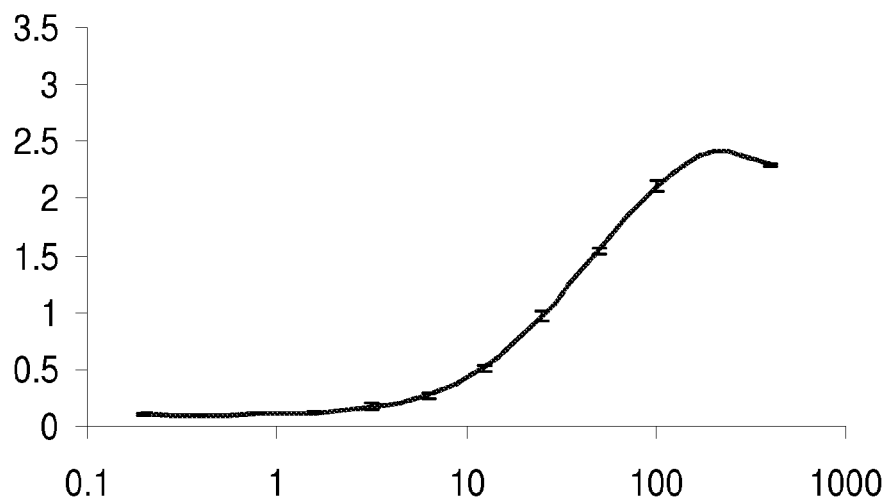
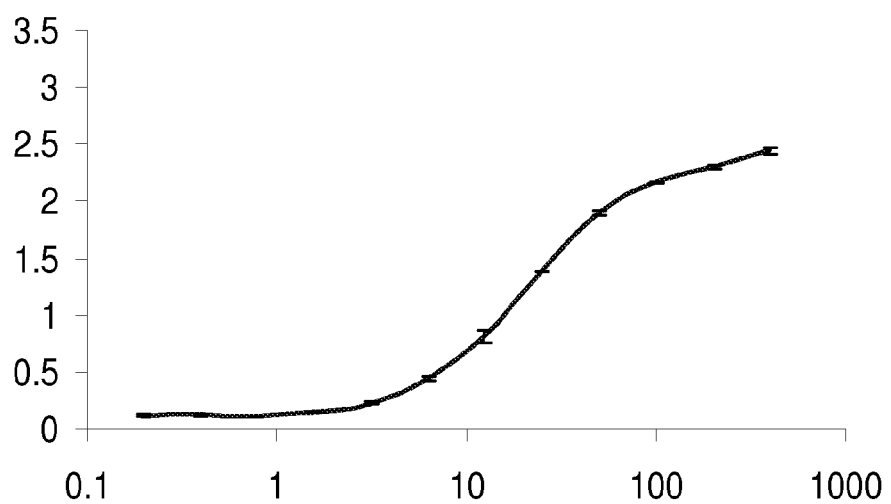
FIGURE 8D

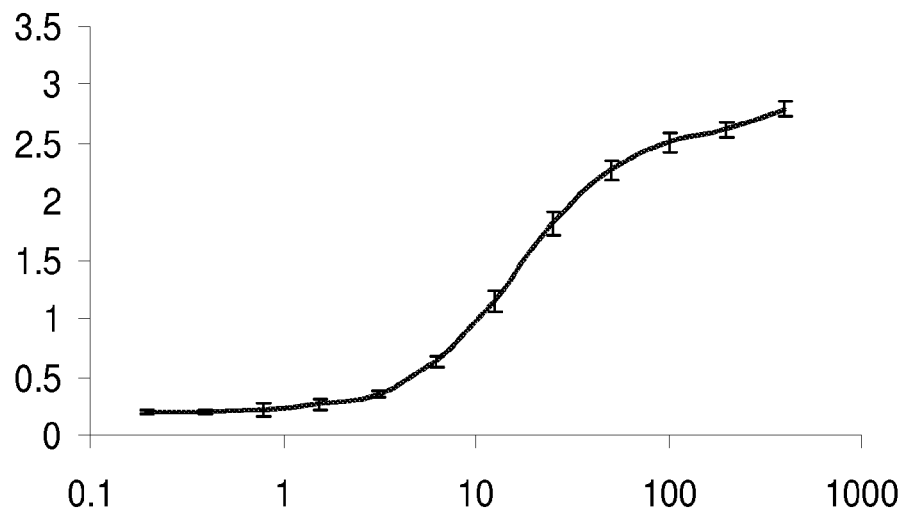
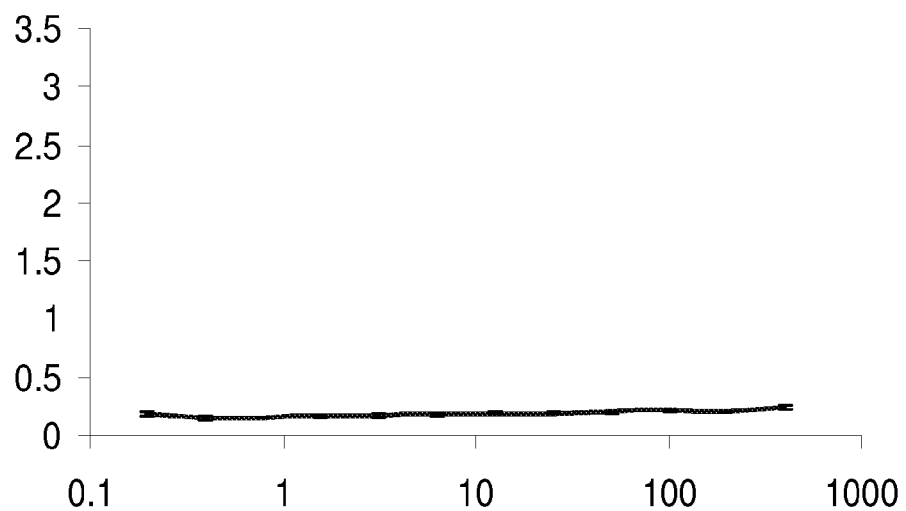
FIGURE 8E

IGF-1R BINDING POLYPEPTIDES AND THEIR USE

CROSS-REFERENCE TO RELATED APPLICATIONS

This application is a US National Stage application of PCT/EP2008/059391 filed 17 Jul. 2008, which claims priority to U.S. Patent Application Ser. No. 60/963,223 filed Aug. 3, 2007.

FIELD OF THE INVENTION

This invention relates to polypeptides which bind to insulin-like growth factor 1 receptor (IGF-1R). The polypeptides have industrial applications for example in medicine, veterinary medicine, imaging, separation techniques and diagnostics.

BACKGROUND

The insulin-like growth factor 1 receptor (IGF-1R) is a membrane-spanning tyrosine kinase. It is a hetero-tetrameric complex consisting of two extracellular α chains and two membrane-spanning β chains, which are interconnected by several disulphide bridges. Binding of insulin-like growth factor 1 (IGF-1), and to a lesser extent insulin-like growth factor 2 and insulin, activates the receptor and leads to an autophosphorylation of tyrosines in the intracellular kinase domain in the β-chains. The activated receptor subsequently submits a mitogenic signal through, among others, the ras signaling pathway (McCormick, Nature 363:15-16 (1993)).

IGF-1R is expressed in most cell types and involved in cell growth, but it is not an absolute requirement for growth (Baker et al, Cell 75:73-82 (1993); Sell et al, Mol Cell Biol 14:3604-3612 (1994)). The over-expression and hyperactivation of IGF-1R, however, is implicated in transformation and tumorigenesis. Increased expression of IGF-1R has been observed in many human malignancies, including carcinomas of the lung, breast, thyroid, gastrointestinal tract and prostate, glioblastomas, neuroblastomas, rhabdomyosarcomas and leukemias (Macaulay, Br J Cancer 65:311-320 (1992)). IGF-1R also functions as a positive regulator of the invasive/metastatic phenotype (Long et al, Exp Cell Res 238: 116-121 (1998)). Based on those features, IGF-1R is an attractive target for cancer therapy. A number of antibodies to IGF-1R have been developed, and some of them have been found to block IGF-1 binding and inhibit growth of several cancer cells (Rohlik et al, Biochem Biophys Res Commun 149:276-281 (1987); Scotlandi et al, Cancer Res58:4127-4131 (1998)). It was also able to enhance the antitumor activity of conventional chemotherapy (Benini et al, Clin Cancer Res 7:1790-1797 (2001)). The mouse monoclonal antibodies MAB 391 and mAb 4G11 were able to down-regulate IGF-1R expression (Hailey et al, Mol Cancer Ther 1:1349-1353 (2002); Jackson-Booth et al, Horm Metab Res 35:850-856 (2003)) and cause reversal of tumor phenotype (Burtrum et al, Cancer Res 63:8912-8921 (2003)). An engineered humanized antibody, mAb1H7, was shown to suppress tumor growth of MCF7 xenografts (Sachdev et al, Cancer Res 63:627-635 (2003)). The fully human antibody A12 could block IGF-1 binding, deactivating IGF-1R and inducing receptor degradation (Burtrum et al, supra). One antibody (CP-751,871) is currently subject to a phase I clinical trial for the treatment of multiple myeloma (Miller et al, Cancer Res 65:10123-10127 (2005)).

Despite the comparable success of currently used IGF-1R antibodies, a substantial number of important questions remain concerning the future of this strategy. As a consequence, the continued provision of agents with a comparable affinity for IGF-1R remains a matter of substantial interest within the field, as well as the provision of uses of such molecules in the treatment and diagnosis of disease. It is therefore an object of the invention to provide new IGF-1R-binding agents, that could for example be used for diagnostic, in vitro or in vivo imaging, and therapeutic applications.

SUMMARY OF THE INVENTION

According to one aspect thereof, the invention provides an insulin-like growth factor 1 receptor (IGF-1R) binding polypeptide, comprising an insulin-like growth factor 1 receptor binding motif, IBM, which motif consists of an amino acid sequence selected from:

i) $EX_2X_3X_4AX_6X_7EIX_{10}X_{11}LPNLX_{16}X_{17}X_{18}QX_{20}X_{21}\text{-}AFIX_{25}SLX_{28}D$ (SEQ ID NO:398), wherein, independently of each other,
$X_2$ is selected from G, P and K;
$X_3$ is selected from F and Y;
$X_4$ is selected from Y and F;
$X_6$ is selected from A, L, S and G;
$X_7$ is selected from I, L, M and V;
$X_{10}$ is selected from I, L, and V;
$X_{11}$ is selected from T, A, S, G, L, Q, I and V;
$X_{16}$ is selected from N and T;
$X_{17}$ is selected from S, Q, H, R, N, K, P, A, D, E, G and T;
$X_{18}$ is selected from S, Q, H, R, N, K, D, P, T and G;
$X_{20}$ is selected from S, Q, H, R, and W;
$X_{21}$ is selected from T, G, R, A, N, D, Q, E, K and S;
$X_{25}$ is selected from T, G, R, A, N, D, Q, E, K, H and S; and
$X_{28}$ is selected from E, N, G, S, A, T, K, P, Q and D;
and ii) an amino acid sequence which has at least 85% identity to the sequence defined in i).

The above definition of a class of sequence related, IGF-1R-binding polypeptides according to the invention is based on an analysis of a number of random polypeptide variants of a parent scaffold, that were selected for their interaction with IGF-1R in selection experiments. The identified IGF-1R-binding motif, or "IBM", corresponds to the target binding region of the parent scaffold, which region constitutes two alpha helices within a three-helical bundle protein domain. In the parent scaffold, the varied amino acid residues of the two IBM helices constitute a binding surface for interaction with the constant Fc part of antibodies. In the present invention, the random variation of binding surface residues and the subsequent selection of variants have replaced the Fc interaction capacity with a capacity for interaction with IGF-1R.

As the skilled person will realize, the function of any polypeptide, such as the IGF-1R-binding capacity of the polypeptides according to the invention, is dependent on the tertiary structure of the polypeptide. It is therefore possible to make minor changes to the sequence of amino acids in a polypeptide without affecting the function thereof. Thus, the invention encompasses modified variants of the IBM of i), which are such that the resulting sequence is at least 85% identical to a sequence belonging to the class defined by i). For example, it is possible that an amino acid residue belonging to a certain functional grouping of amino acid residues (e.g. hydrophobic, hydrophilic, polar etc) could be exchanged for another amino acid residue from the same functional group.

In one embodiment of the polypeptide according to the invention, $X_2$ is G.

In one embodiment of the polypeptide according to the invention, $X_3$ is F.

In one embodiment of the polypeptide according to the invention, $X_4$ is Y.

In one embodiment of the polypeptide according to the invention, $X_6$ is A.

In a more specific embodiment of the polypeptide according to the invention, $X_3X_4$ is FY and $X_6$ is A.

In one embodiment of the polypeptide according to the invention, $X_{10}$ is L.

In a more specific embodiment of the polypeptide according to the invention, $X_2X_3X_4$ is GFY, $X_6$ is A and $X_{10}$ is L.

In one embodiment of the polypeptide according to the invention, $X_7$ is I.

In a more specific embodiment of the polypeptide according to the invention, $X_2X_3X_4$ is GFY, $X_6X_7$ is AI and $X_{10}$ is L.

In one embodiment of the polypeptide according to the invention, $X_{16}$ is N.

In one embodiment of the polypeptide according to the invention, $X_{17}$ is H.

In one embodiment of the polypeptide according to the invention, $X_{18}$ is selected from K and S, and may in particular be S.

In one embodiment of the polypeptide according to the invention, $X_{20}$ is R.

In one embodiment of the polypeptide according to the invention, $X_{21}$ is selected from T and G, and may in particular be T.

In one embodiment of the polypeptide according to the invention, $X_{25}$ is T.

In a more specific embodiment of the polypeptide according to the invention, $X_{20}X_{21}$ is RG and $X_{25}$ is T.

In a more specific embodiment of the polypeptide according to the invention, $X_{11}$ is S, $X_{17}X_{18}$ is HS, $X_{20}X_{21}$ is RG and $X_{25}$ is T.

In one embodiment of the polypeptide according to the invention, $X_{28}$ is E.

In a more specific embodiment of the polypeptide according to the invention, $X_{11}$ is A, $X_{17}X_{18}$ is RK, $X_{20}X_{21}$ is ST and $X_{28}$ is E.

As described in detail in the experimental section to follow, the selection of IGF-1R-binding variants has led to the identification of individual IGF-1R-binding motif (IBM) sequences. These sequences constitute individual embodiments of the IBM sequence i) in the definition of IGF-1R-binding polypeptides according to this aspect of the present invention. The sequences of individual IGF-1R-binding motifs are presented in FIG. 1A-1N and as SEQ ID NO:1-197. In embodiments of this aspect of the invention, the IBM sequence i) may in particular be selected from SEQ ID NO:1-2, 52, 58, 101, 110, 115, 126, 130 and 166. In a more specific embodiment, the IBM sequence i) is selected from SEQ ID NO:110, 115 and 126.

In embodiments of the present invention, the IBM may form part of a three-helix bundle protein domain. For example, the IBM may essentially constitute or form part of two alpha helices with an interconnecting loop, within said three-helix bundle protein domain.

In particular embodiments of the invention, such a three-helix bundle protein domain is selected from domains of bacterial receptor proteins. Non-limiting examples of such domains are the five different three-helical domains of protein A from *Staphylococcus aureus*, and derivatives thereof. Thus, an IGF-1R-binding polypeptide according to the invention may comprise an amino acid sequence selected from:

```
                                     (SEQ ID NO: 399)
ADNNFNK-[IBM]-DPSQSANLLSEAKKLNESQAPK (IBM within
domain A of staphylococcal protein A);

(SEQ ID NO: 400)
ADNKFNK-[IBM]-DPSQSANLLAEAKKLNDAQAPK (IBM within
domain B of staphylococcal protein A);

(SEQ ID NO: 401)
ADNKFNK-[IBM]-DPSVSKEILAEAKKLNDAQAPK (IBM within
 staphylococcal protein A);

(SEQ ID NO: 402)
ADAQQNNFNK-[IBM]-DPSQSTNVLGEAKKLNESQAPK (IBM
within domain C of domain D of staphylococcal
protein A);

(SEQ ID NO: 403)
AQHDE-[IBM]-DPSQSANVLGEAQKLNDSQAPK (IBM within
domain E of staphylococcal protein A);
and (SEQ ID NO: 404)
VDNKFNK-[IBM]-DPSQSANLLAEAKKLNDAQAPK (IBM within
the protein Z derivative of domain B of staphylo-
coccal protein A);
``` wherein [IBM] is an IGF-1R-binding motif as defined above.

According to another alternative aspect thereof, the invention provides an IGF-1R-binding polypeptide, whose amino acid sequence comprises a sequence which fulfils one definition selected from the following: iii) it is selected from SEQ ID NO:198-394, and iv) it is an amino acid sequence having 85% or greater identity to a sequence selected from SEQ ID NO: 198-394. In embodiments of this aspect of the invention, the IGF-1R-binding polypeptide may in particular comprise a sequence selected from SEQ ID NO:198-199, 249, 255, 298, 307, 312, 323, 327 and 363, and sequences having 85% or greater identity thereto. In one specific embodiment, the IGF-1R-binding polypeptide may in particular comprise a sequence selected from SEQ ID NO: 307, 312 and 323, and sequences having 85% or greater identity thereto.

An IGF-1R-binding polypeptide according to any aspect of the invention may bind to IGF-1R such that the $K_D$ value of the interaction is at most $1 \times 10^{-6}$ M, for example at most $1 \times 10^{-7}$ M.

When reference is made herein to the degree of identity between the amino acid sequences of different polypeptides, the lower limit of 85% identity to a sequence disclosed herein is given. In some embodiments, the inventive polypeptide may have a sequence which is at least 86%, at least 87%, at least 88%, at least 89%, at least 90%, at least 91%, at least 92%, at least 93%, at least 94%, at least 95%, at least 96%, at least 97%, at least 98% or at least 99 identical to the sequence described herein. The comparison may be performed over a window corresponding to the shortest of the sequences being compared, or over a window corresponding to an IGF-1R-binding motif in at least one of the sequences being compared.

The polypeptides are advantageous in that they bind well to an IGF-1R. The polypeptides may for example bind to the ectodomain of IGF-1R, such as the ectodomain corresponding to SEQ ID NO:397. Typically, the polypeptides can be relatively short and by virtue of their small size they should have better penetration in tumor tissue than antibodies while at the same time have better systemic circulation properties than conventional low molecular weight IGF-1R-binding substances (often too short half-lives) and monoclonal antibodies (often too long circulation times). In addition to the development of marketed molecular imaging agents, applications include use in the drug development and screening procedure where specific imaging agents are desired to measure outcome of treatment in in vivo models and subsequently during clinical development. Molecular imaging provides a direct read-out of efficacy of a pharmaceutical aimed to down-regulate a growth factor receptor, as well as for assessing the anti-tumor effect.

A polypeptide in accordance with the invention may be about 53-58 amino acids in length. However, the length can be greater or smaller. The length of the polypeptide can for example be reduced at the N terminus by up to four amino acids.

The use of the term "position" is relative. In a polypeptide in accordance with the invention which has as many amino acid residues as a specifically disclosed polypeptide, i.e. those described above, the positions of amino acids in the polypeptide correspond exactly to those in the disclosed polypeptides. In a situation where there is, for example, an N terminal extension compared to the disclosed polypeptides, those amino acid residues in the extended peptide that correspond to those of the non-extended peptide have the same position numbers. For example, if there is a six amino acid residue extension on the extended polypeptide, then amino acid number seven of that modified polypeptide, counting from the N terminus, corresponds to the amino acid in position number one of the disclosed polypeptide.

Accordingly, a polypeptide according to the invention may be used as an alternative to conventional antibodies or low molecular weight substances in various medical, veterinary, diagnostic and imaging applications. For example, the IGF-1R-binding polypeptides of the invention may be used in the treatment of IGF-1R-related cancers such as those caused by over-expression of IGF-1R described above, e.g. carcinomas of the lung, breast, thyroid, gastrointestinal tract and prostate, glioblastomas, neuroblastomas, rhabdomyosarcomas and leukemias. The IGF-1R-binding polypeptides of the invention may be used to inhibit cell signaling by binding to an IGF-1R on a cell surface. Such blocking of receptor function may be utilized to obtain a therapeutic effect, in analogy with antibodies that compete with IGF-1 for binding to the receptor The IGF-1R-binding polypeptides of the invention may also be used in the diagnosis of cancer, both in vivo and in vitro, in targeting agents to cells which express IGF-1R, particularly cells which over-express IGF-1R, in histochemical methods for the detection of IGF-1R, in methods of separation and other applications. In addition to the development of molecular imaging agents for the clinic, an application exists for specific preclinical imaging agents to measure outcome of treatment in in vivo models and subsequently during clinical development. Molecular imaging should provide a direct read-out of the efficacy of a pharmaceutical aimed to down-regulate a growth factor receptor e.g. IGF-1R, as well as for assessing the anti-tumor effect. The polypeptides of the invention may be useful in any method which relies on affinity for IGF-1R of a reagent. Thus, the polypeptides may be used as a detection reagent, a capture reagent or a separation reagent in such methods, but also as a therapeutic or diagnostic agent in their own right or as a means for targeting other therapeutic or diagnostic agents, with direct (e.g. toxic molecules, toxins) or indirect effects (e.g. cancer vaccines, immunostimulatory molecules) to the IGF-1R protein.

Methods that employ the polypeptides in accordance with the invention in vitro may be performed in different formats, such as microtitre plates, in protein arrays, on biosensor surfaces, on beads, in flow cytometry, on tissue sections, and so on.

The skilled addressee will appreciate that various modifications and/or additions can be made to a polypeptide according to the invention in order to tailor the polypeptide to a specific application without departing from the scope of the present invention. These modifications and additions are described in more detail below and may include additional amino acids in the same polypeptide chain, or labels and/or therapeutic agents that are chemically conjugated or otherwise bound to the polypeptide of the invention.

Furthermore, the invention also encompasses fragments of IGF-1R-binding polypeptides according to the invention that retain IGF-1R-binding. The possibility of creating fragments of a wild-type *Staphylococcus aureus* protein A domain with retained binding specificity was shown by Braisted A C et al in Proc Natl Acad Sci USA 93:5688-5692 (1996). In the experiments described in that paper, using a structure-based design and phage display methods, the binding domain of a three-helix bundle of 59 residues was reduced to a resulting two-helix derivative of 33 residues. This was achieved by stepwise selection of random mutations from different regions, which caused the stability and binding affinity to be iteratively improved. Following the same reasoning, with the polypeptides of the present invention, the skilled addressee will be able to obtain a "minimized" IGF-1R-binding polypeptide with the same binding properties as that of the "parent" IGF-1R-binding polypeptide. Thus, a polypeptide constituting a fragment of a polypeptide according to the invention, which fragment retains target binding, is within the scope of the invention. Such a fragment may for example comprise an N terminal reduction, such as by up to four amino acid residues, of a polypeptide as described above.

The terms "IGF-1R-binding" and "binding affinity for IGF-1R" as used in this specification refers to a property of a polypeptide which may be tested for example by the use of surface plasmon resonance technology, such as in a Biacore instrument (Biacore AB). For example as described in the examples below, IGF-1R-binding affinity may be tested in an experiment in which IGF-1R, or a fragment of IGF-1R such as the ectodomain comprising amino acid residues 1-901 (Jansson et al, J Biol Chem 272:8189-8197 (1997)), is immobilized on a sensor chip of the instrument, and the sample containing the polypeptide to be tested is passed over the chip. Alternatively, the polypeptide to be tested is immobilized on a sensor chip of the instrument, and a sample containing IGF-1R, or fragment thereof, is passed over the chip. Thus, IGF-1R may, in this regard, be a polypeptide comprising the amino acid sequence SEQ ID NO:396, and its ectodomain may be a polypeptide comprising the amino acid sequence SEQ ID NO:397. The skilled person may then interpret the results obtained by such experiments to establish at least a qualitative measure of the binding affinity of the polypeptide for IGF-1R. If a qualitative measure is desired, for example to determine a $K_D$ value for the interaction, surface plasmon resonance methods may also be used. Binding values may for example be defined in a Biacore 2000 instrument (Biacore AB). IGF-1R is immobilized on a sensor chip of the measurement, and samples of the polypeptide whose affinity is to be determined are prepared by serial dilution and injected in random order. $K_D$ values may then be calculated from the results using for example the 1:1 Langmuir binding model of the BIAevaluation 4.1 software provided by the instrument manufacturer.

Where amino acid substitutions are introduced, these should not affect the basic structure of the polypeptide. For example, the overall folding of the Cα backbone of the central three-helix bundle of the polypeptide can be essentially the same as that of a Z "wild-type" domain to which it may be related, i.e. having the same elements of secondary structure in the same order. Thus polypeptides having this basic structure will have similar CD spectra to the Z "wild-type" domain. The skilled addressee is aware of other parameters that may be relevant. The requirement of conserving the basic structure, places restrictions on which positions of the amino acid sequence may be subject to substitution. For example, it is preferred that amino acid residues located on the surface of the polypeptide are substituted, whereas amino acid residues buried within the core of the polypeptide "three-helix bundle" should be kept constant in order to preserve the structural properties of the molecule. The same reasoning applies to fragments of polypeptides of the invention.

The invention also covers polypeptides in which the IGF-1R-binding polypeptide described above is present as an IGF-1R-binding domain to which additional amino acid residues have been added at either terminal. These additional amino acid residues may play a role in enhancing the binding of IGF-1R by the polypeptide, but may equally well serve other purposes, related for example to improving one or more of the production, purification, stabilization in vivo and/or in vitro, coupling or detection of the polypeptide. Such additional amino acid residues may comprise one or more amino acid residues added for the purpose of chemical coupling. One example of this, is the addition of a cysteine residue at the very first or very last position in the polypeptide chain, i.e. at the N or C terminus. Such additional amino acid residues may also provide a "tag" for purification or detection of the polypeptide such as a $His_6$ tag or a "myc" (c-myc) tag or a "FLAG" tag for interaction with antibodies specific to the tag.

The present invention also covers IGF-1R-binding polypeptides in which a IGF-1R-binding polypeptide as described above is present as an IGF-1R-binding domain to which additional peptides or proteins or other functional groups are coupled N- or C-terminally or to any other residues (specifically or non-specifically) by means of chemical conjugation (using known organic chemistry methods).

The "additional amino acid residues" discussed above may also provide one or more polypeptide domains with any desired function, such as the same binding function as the first, IGF-1R-binding domain, or another binding function, or an enzymatic function, toxic function (e.g. an immunotoxin), or a fluorescent signaling function, or combinations thereof.

The polypeptide of the invention may be in monomeric or multimeric forms. Multimeric forms of the polypeptide may be advantageous in that they may have enhanced binding properties. Preferred multimeric forms include dimeric and trimeric forms. Multimeric forms of the polypeptides may comprise a suitable number of polypeptides of the invention. These polypeptides essentially form domains within the multimer. These domains may all have the same amino acid sequence, but alternatively, they may have different amino acid sequences. The polypeptides may be joined by covalent coupling using known organic chemistry methods, or expressed as one or more fusion polypeptides in a system for recombinant expression of polypeptides, or joined in any other fashion, either directly or via a linker, for example an amino acid linker.

Additionally, fusion polypeptides, in which the IGF-1R-binding polypeptide of the invention provides a first domain or moiety, and second or further moieties have other functions than binding IGF-1R are also contemplated and within the scope of the present invention. The second or further moieties of such a fusion polypeptide may comprise a binding domain with an affinity for another target molecule than IGF-1R. Such a binding domain may be another, similar polypeptide binder. For example, the polypeptide binder may be a Z variant. This makes it possible to create multi-specific reagents that may be used in several types of applications such as medicine, veterinary medicine, diagnosis, separation, and imaging. The preparation of such multi-specific fusion polypeptides may be performed as generally described above.

In other embodiments of the invention, the second or further moieties may comprise an unrelated, naturally occurring or recombinant protein (or a fragment thereof which retains the binding or other ability of the naturally-occurring or recombinant protein) having a binding affinity for a target. For example, an IGF-1R-binding polypeptide in accordance with the invention may be joined to an albumin-binding domain, such as the albumin binding domain GA3 of protein G from *Streptococcus* strain G148 or a derivative thereof, or any other polypeptide with affinity for a serum protein to prolong the half-life of the IGF-1R-binding polypeptide for use in applications in vivo, such as diagnostic or therapeutic applications.

The IGF-1R-binding polypeptides of the present invention may be provided in the form of other fusion polypeptides. For example the IGF-1R-binding polypeptide, or fragment thereof, may be covalently coupled to a second or further moiety or moieties, which in addition to, or instead of target binding, exhibit other functions. One example would be a fusion between one or more IGF-1R-binding polypeptides and an enzymatically active polypeptide serving as a reporter or effector moiety. Examples of reporter enzymes, which may be coupled to the IGF-1R-binding polypeptide to form a fusion protein, are well-known to the skilled person and include enzymes such as β-galactosidase, alkaline phosphatase, horseradish peroxidase, carboxypeptidase. Other options for the second and further moiety or moieties of a fusion polypeptide according to the invention include fluorescent polypeptides, such as green fluorescent protein, red fluorescent protein, luciferase and variants thereof.

Other options for the second and further moiety or moieties of a fusion polypeptide according to the invention include a moiety or moieties for therapeutic applications. In therapeutic applications, other molecules can also be coupled, covalently or non-covalently, to the IGF-1R-binding polypeptide of the invention by other means. For example, other molecules such as enzymes for "ADEPT" (Antibody-Directed Enzyme Prodrug Therapy) applications using the polypeptide of the invention to direct the effector enzyme (e.g. carboxypeptidase) or RNase or DNase fusions; proteins for recruitment of effector cells and other components of the immune system; cytokines, such as IL-2, IL-12, TNFα, IP-10; pro coagulant factors, such as tissue factor, von Willebrand factor; toxins, such as ricin A, *Pseudomonas* exotoxins, calcheamicin, maytansinoid, toxic small molecules, such as auristatin analogues, doxorubicin.

The above-described additional amino acids (particularly hexahistidine, cysteine) can be used to comprise a chelator to facilitate incorporation of a radionuclide for the purposes of using an inventive IGF-1R-binding polypeptide in imaging in vivo or in vitro. Those, or other amino acid residues on the surface of the polypeptide itself may also be used as an attachment site for indirect labeling with a molecule containing a radionuclide (often used with radio-halogens) or as an attachment site for a chelating moiety which is subsequently used to capture a radio-metal. Non-limiting examples of radionuclides for diagnosis are $^{68}Ga$, $^{76}Br$, $^{111}In$, $^{99m}Tc$ and $^{125}I$, and non-limiting examples of radionuclides for therapy are $^{90}Y$, $^{131}I$, $^{211}At$ and $^{177}Lu$.

The invention also embraces polypeptides in which the IGF-1R-binding polypeptide described above has been provided with a label group, such as at least one fluorophore, biotin or radioactive isotope, for example for the purposes of detection of the polypeptide in vitro and/or in vivo.

With regard to the description above of fusion polypeptides and proteins incorporating an IGF-1R-binding polypeptide of the invention, it should be noted that the designation of first, second and further moieties is made for the purposes of clarity to distinguish between the IGF-1R-binding moiety or moieties on the one hand, and moieties exhibiting other functions on the other hand. These designations are not intended to refer to the actual order of the different domains in the polypeptide chain of the fusion protein or polypeptide. Thus, for example, a first moiety may be appear at the N-terminal end, in the middle, or at the C-terminal end of the fusion protein or polypeptide.

Further preferred aspects and embodiments of the invention are apparent from the appended claims.

BRIEF DESCRIPTION OF THE FIGURES

FIG. 1A-1N is a listing of the amino acid sequences of examples of IGF-1R binding motifs comprised in IGF-1R binding polypeptides of the invention (SEQ ID NO:1-197), examples of IGF-1R binding polypeptides according to the invention (SEQ ID NO:198-394), the protein Z derivative of domain B of *Staphylococcus aureus* protein A (SEQ ID NO:395), entire human IGF-1R (SEQ ID NO:396) and the ectodomain of human IGF-1R (SEQ ID NO:397).

FIG. 2 shows the result of an SDS-PAGE gel electrophoresis of purified Z variants in the following order from left to right: Z01778, Z01779, Z01780, Z01781, Z01997, Z01998, Z01999, Z02001, Z02002, Z02003 and Z02008.

FIGS. 8A-8E are dose response curves from the ELISA experiment described in Example 4 for the nine indicated IGF-1R specific Z variants and for Z00810 (negative control). Concentration of the indicated Z variants ranges from 400 ng/ml to 0.2 ng/ml (X-axis). The Z variant molecule concentration is plotted against the absorbance at 450 nm.

EXAMPLE 1

Figure 3:
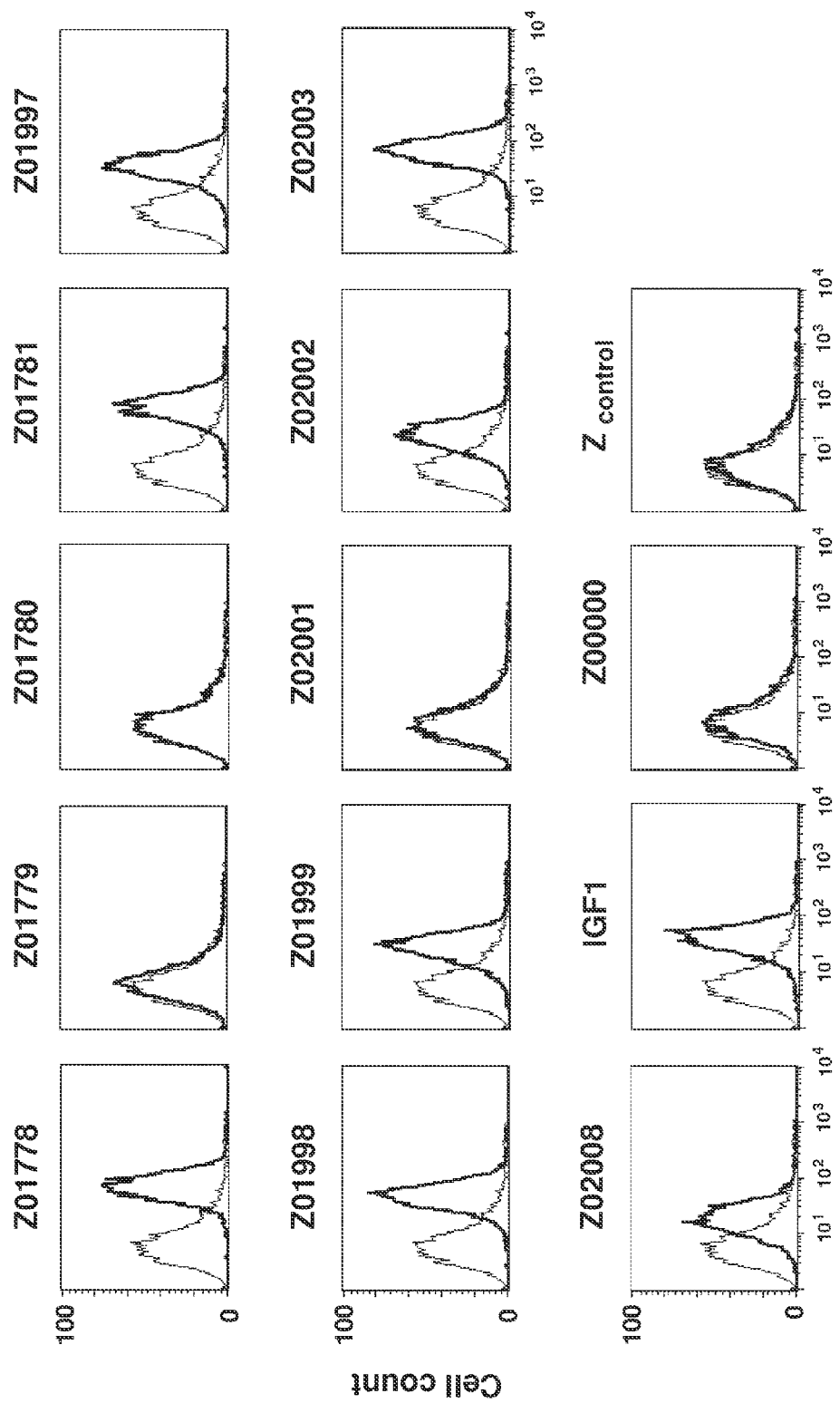
FIG. 3: MCF-7 cells were stained with biotinylated Z variants at a concentration of 1 μg/ml. This was followed by incubation with neutravidin labeled with Alexa Fluor 488 and subsequently with Amplification kit A and B from Molecular Probes. The cells were analyzed in a flow cytometer. Thin lines correspond to non-stained cells. Thick lines correspond to stained cells.

Selection and characterization of IGF-1R binding polypeptides

Materials and Methods

General: *Escherichia coli* strain RR1ΔM15 (Wither, Nucleic Acids Res 10:5765-5772, 1982) was used throughout this work except where otherwise noted. The nucleotide sequence of all DNA constructs was verified by cycle sequencing using an ABI9600 sequencing machine (Applied Biosystems).

Production and purification of IGF-1R: HEK-293 cells expressing the ectodomain of the IGF-1R with a C-terminal His$_6$-tag (IGF-1R) (Jansson et al, J Biol Chem 272:8189-8197 (1997)) were cultivated continuously and the culture medium was collected and stored at −80° C. Upon purification, 675 ml medium was thawed and concentrated by ultracentrifugation to a total volume of 55 ml. The medium was desalted on a 245 ml Sephadex G25 column (GE Healthcare) and then purified on a 1 ml Histrap FF column (GE Healthcare) using the His$_6$ purification tag. Elution from the column was performed using 300 mM imidazole, and eluted material was desalted to 10 mM HEPES, pH 7.4, and stored until use.

Selection of IGF-1R binding polypeptides: A library of random variants of protein Z (Nilsson et al, Prot Eng 1:107-113, 1987) displayed on bacteriophage was used to select IGF-1R binding polypeptides. The library was constructed essentially as described in Nord et al, Prot Eng 8:601-608 (1995). Selection was performed as follows: Four approaches with four cycles each were performed for selection. To avoid non-specific binding, all tubes used for selection were blocked with 0.1% gelatin in PBST (PBS: 10 mM phosphate, 137 mM NaCl, pH 7.2, supplemented with 0.1% Tween 20). For the first two cycles of selection, the phage stock, prepared according to previously described procedures (Nord et al, Nat Biotech 15:772-777 (1997); Hansson et al, Immunotechnology 4:237-252 (1999)) was pre-incubated with Talon™ beads (Clontech). The resulting supernatant was mixed with non-biotinylated IGF-1R at 10 nM (for selection 1) or 100 nM (for selections 2, 3 and 4) and 20 ml (for selection 1) or 200 ml (for selections 2, 3 and 4) of fresh Talon™ beads, followed by incubation under continuous rotation (end over end) at room temperature for 2 h. After wash for increasing times with PBST (1% rather than 0.1% of Tween 20 was supplemented for selection 3), the bound phage were eluted with 500 ml of 200 mM imidazole in PBS, pH 7.2 (imidazole) for selections 1, 2 and 3 and with 76 ml of IGF-1 at 1 mg/ml (10 mM) for selection 4. For cycles 3 and 4 of selection, the phage stocks were pre-incubated with M-280 paramagnetic beads with immobilized streptavidin (Dynabeads®; Invitrogen). The supernatant was mixed with 10 nM (for selection 1) or 20 nM biotinylated IGF-1R supplemented with 75 ml (for selection 1) or 150 ml (for selections 2, 3 and 4) of fresh M-280 beads. Biotinylation of IGF-1R was performed using EZ-Link™ Sulfo-NHS-LC-Biotin (Pierce). A 15-fold molar excess of biotin was added to IGF-1R in PBS and the mixture was incubated on ice for 2 h followed by extensive dialysis against PBS at 4° C. 500 ml of 50 mM glycine hydrochloride, pH 2.2, was used for elution of bound phage for selections 1, 2 and 3, while 15 ml of the above IGF-1 (2 mM) was used for elution in selection 4. The eluted phages were amplified in $E.\ coli$ strain RR1ΔM15 between the cycles. After the fourth cycle of selection, a number of colonies were isolated and grown in 1 ml cultures. Their Z variant-encoding inserts were expressed by addition of IPTG. Expressed Z variants fused to an albumin binding domain (ABD; the albumin binding domain GA3 of protein G from $Streptococcus$ strain G148) were released from cells by the freeze/thaw method. To test if the variants could indeed interact with the IGF-1R, an ELISA was performed. 100 µl of a solution containing 6 µg/ml human serum albumin was added to each well of an 96-well ELISA plate and incubated over night. The HSA solution was poured off and the wells were blocked with 200 µl of 2% non-fat dry milk solution for 1 h. 100 µl of released Z variant solution from each of the cultivations were added to each well and incubated 1.5 h at room temperature with slow shaking. The supernatants were poured off and the wells were washed 5 times with PBST. 100 µl biotinylated IGF-1R (1 µg/ml) were added to each well and incubation was performed for 90 min with slow shaking. The wells were washed with PBST 5 times and a conjugate of streptavidin and horseradish peroxidase was added to the wells followed by development with a TMB substrate (Pierce) according to the manufacturer's recommendations.

Sub-cloning and expression of Z variants: Selected Z variants were sub-cloned in the pAY442 vector (Grönwall et al, J Biotechnol 128:162-183 (2007)) using sticky-end cloning essentially as described previously. The variants were expressed by addition of 1 mM IPTG and purified by immobilized metal affinity chromatography on a Talon™ resin (Clontech). The purified Z variants were subsequently biotinylated using EZ-Link™ Sulfo-NHS-LC-Biotin (Pierce) according to the manufacturer's recommendations.

Flow cytometry: Sub-confluent MCF-7 cells (Deutsche Sammlung von Mikroorganismen and Zellkulturen; no ACC115) were detached with a solution of 0.05% trypsin and 0.53 mM EDTA (Invitrogen). For every sample, 150 000 cells were collected, washed once with PBSB (PBS: 100 mM Na phosphate, pH 7.5, 100 mM NaCl, supplemented with 1% bovine serum albumin). Staining of cells with biotinylated Z variants was performed by incubation with 70 ml of Z variant solution at 1 µg/ml unless otherwise noted for 1 h at room temperature. The cells were washed once with PBSB and incubated with 70 µl of FITC-labeled neutravidin (1 µg/ml) for 30 min on ice. The cells were washed again and treated with the Alexa Fluor® 488 Signal-amplification kit (Molecular Probes) essentially as recommended by the manufacturer. After staining with Z variants, the cells were washed once with PBSB and re-suspended in PBSB and analyzed in a FacsVantage SE flow cytometer (BD Biosciences) fitted with a 100 mm nozzle. 10 000 events were recorded for each sample, and the population corresponding to single cells was gated and analyzed as histogram plots.

Immunofluorescence: MCF-7 cells (supra) were grown over night on multi-well slides (Histolab, Sweden) and subjected to staining the following day after a brief wash in PBS. The cells were stained with the Z variant Z01781 at a concentration of 10 µg/ml. Z01781 was detected with a purified goat IgG against an epitope common for all Z variants (Anti-ZBirk005), followed by Alexa Fluor® 488 labeled anti-goat IgG (Molecular Probes, Invitrogen).

Results

Phage selection from Z variant library: To generate IGF-1R binding Z variant polypeptides, a library displayed on bacteriophage was subjected to selection using the ectodomain of the receptor as target or "bait". Three parallel selections were carried out to evaluate how receptor concentration and the amount of Tween 20 during selection affected the outcome. Two cycles of selection were performed where the receptor was incubated with the phagemid library followed by isolation of receptor/phagemid complexes by a solid support containing $Co^{2+}$ ions that could specifically interact with the hexahistidine tag present in the receptor. The receptor/phagemid complexes were subsequently eluted by imidazole, followed by amplification in $E.\ coli$. In an attempt to minimize the ability of phagemid particles that bound unspecifically to the $Co^{2+}$ containing matrix to co-purify with the receptor/phagemid complexes, the $Co^{2+}$ containing solid support was replaced with a solid support containing streptavidin in cycles 3 and 4. The target receptor used during these cycles was also biotinylated in vitro to allow capture by streptavidin. During these cycles, the phagemids were eluted by lowering the pH to break the bond between the phagemid and the receptor.

To enrich for Z variants that interact with an epitope overlapping the IGF-1 site of interaction, a fourth selection was performed where elution was carried out using an excess of IGF-1. Capturing using a $Co^{2+}$ containing solid support during cycles 1 and 2 and a streptavidin containing solid support during cycles 3 and 4 was performed in an analogous manner as described above.

In all four selections, an increase in the number of eluted phagemids was observed as the rounds progressed, indicating an enrichment for phagemids interacting specifically with the receptor and/or unspecifically with other components in the system. After the fourth round of selection, randomly picked clones were cultivated and their gene fusion of Z variant and ABD was expressed. Cell lysates from these cultures were prepared and analyzed for binding to the receptor in an ELISA experiment. A number of clones showed interaction with the receptor and the DNA sequence of the Z variant-encoding nucleic acid in these clones was determined. Z variants interacting with the ectodomain of IGF-1R were successfully isolated in all four selection experiments. Each individual Z variant was given a unique identification number #####, and individual variants are referred to as Z#####.

Of the sequences determined, a selected number of sequences were grouped together in a cluster of similar sequences. Interestingly, the selected cluster of similar sequences were identified in the experiment using competitive elution with IGF-1, indicating that these IGF-1R binding polypeptides interact with the same or overlapping epitopes on IGF-1R as does IGF-1. The predicted amino acid sequences of the corresponding polypeptides and their IGF-1R binding motifs were deduced, which yielded a number of sequences of IGF-1R binding polypeptides according to the invention. The amino acid sequences of deduced IGF-1R binding motifs are listed in FIG. 1A-1N and in the sequence listing as SEQ ID NO:1-7, whereas the amino acid sequences of the corresponding full-length Z variants are listed in FIG. 1A-1N and in the sequence listing as SEQ ID NO:198-204.

Analysis of interaction with MCF-7 cells: After the selection and initial screening of Z variants with an affinity for the recombinantly produced ectodomain of IGF-1R, it was of importance to determine if they could also bind to the full receptor in its native state, as part of a cellular membrane. Eleven Z variants from the selection were each sub-cloned in an E. coli expression vector, where they were also fitted with a hexahistidine purification tag. They were expressed and subsequently purified by immobilized metal affinity chromatography. Samples of the purified Z variant molecules were separated by SDS-PAGE. A photograph of the gel is displayed in FIG. 2. All variants could be produced and purified to a high level of purity.

To evaluate the ability of the Z variants to bind to endogenous IGF-1R, the breast cancer cell line MCF-7 was used, which has previously been shown to contain a high number of IGF-1R (Yee, Breast Cancer Res Treat. 32:85-95 (1994)). Biotin was covalently attached to the purified Z variants, and they were subsequently used as a primary reagent to stain MCF-7 cells. The bound Z variants were detected by a neutravidin-FITC/anti-FITC antibody sandwich followed by determination of cellular fluorescence by flow cytometry (FIG. 3). The experiment shows that Z variants Z01778, Z01781 (SEQ ID NO:198), Z01997, Z01998, Z01999, Z02002, Z02003 (SEQ ID NO:199) and Z02008 are able to interact with the cells, whereas Z01779, Z01780 and Z02001 are not. Biotinylated IGF-1 was used as a positive control and could interact with the cells. Two negative controls showed no interaction with the cells: Zwt (also designated Z00000 (SEQ ID NO:395)), which specifically interacts with certain classes of IgG:s (Nilsson et al, supra), and $Z_{control}$, which was isolated in a previous selection effort against an unrelated target protein that was not expected to be present on the surface of MCF-7 cells.

Figure 4:
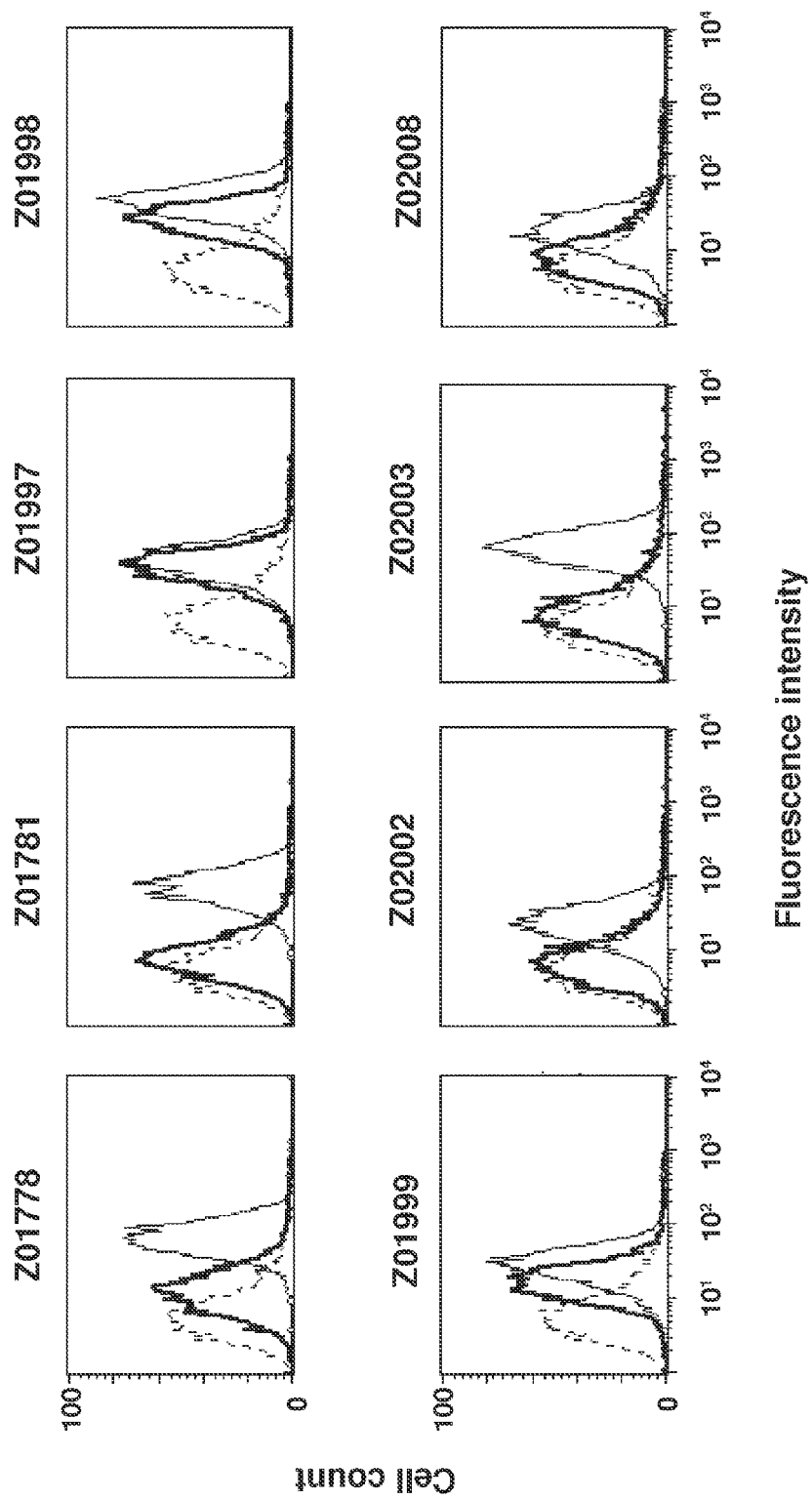
FIG. 4. Non-stained MCF-7 cells (dashed line), and MCF-7 cells stained with Z variants (thin line). Biotinylated and non-biotinylated Z variants at a ratio of 1:10 were mixed and used to stain MCF-7 cells (thick line). Staining was otherwise as in FIG. 3. Variants, for which a 10-fold excess (thick line) is able reduce the fluorescent shift significantly, are characterized as having specific binding, whereas variants where the shift is not reduced stick non-specifically to cells.

Evaluation of the specificity of interaction of Z variants with IGF-1R: To investigate whether the selected Z variants with the ability to bind MCF-7 cells as determined above were specific in their interaction, a competition experiment was performed. Each variant was used as a primary reagent to stain MCF-7 cells in the presence or absence of a 100-fold excess of a non-biotinylated version of the Z variant. If the Z variant was able to bind specifically to the cells, an excess of non-biotinylated Z variant was expected to out-compete the biotinylated Z variant, resulting in a lower amount of bound molecule. Signals from biotinylated Z variants were again detected by a neutravidin-FITC/anti-FITC antibody sandwich followed by determination of cellular fluorescence by flow cytometry (FIG. 4). For Z01781 (SEQ ID NO:198), Z02002, Z02003 (SEQ ID NO:199) and Z02008, a clear quenching of the signal is observed, indicating specific cell binding. For Z01778, Z01997, Z01998 and Z01999 the quenching of the signal is not complete, suggesting that these variants to some extent can interact with cells unspecifically.

Figure 5:
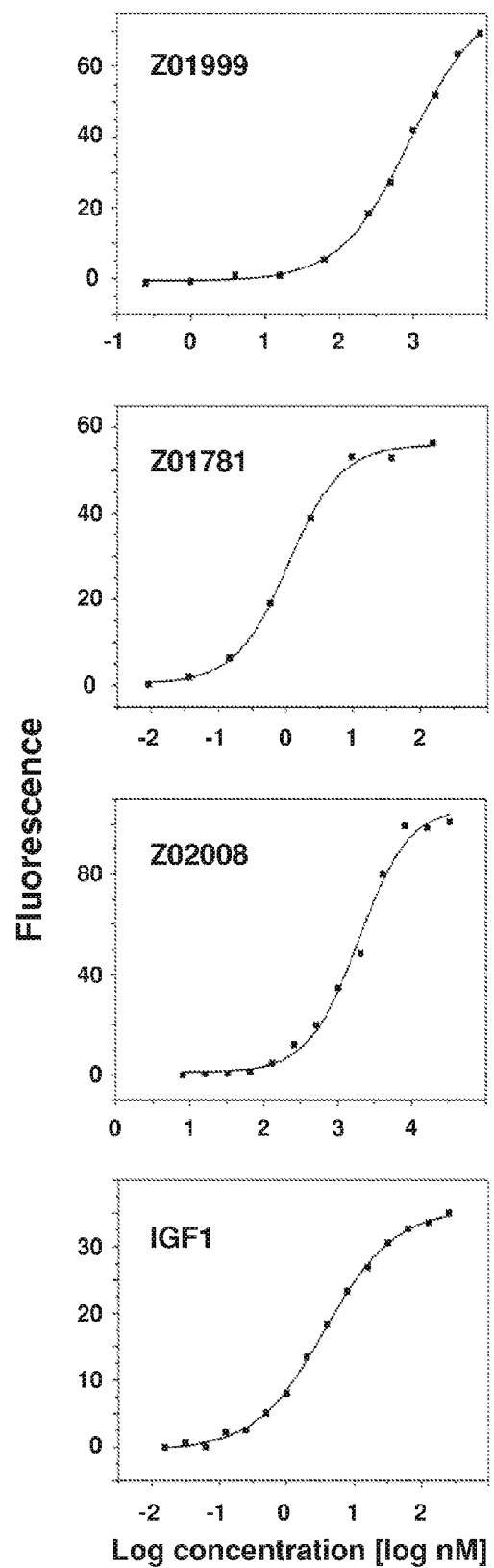
FIG. 5. MCF-7 cells were stained (as in FIG. 3) with different concentrations of selected Z variants as well as with IGF-1. Fluorescent shift was plotted against the logarithmic concentration of the variants. The experiment was repeated three times; the figure shows the result of a representative experiment. The inflection points of the curves correspond to where half the receptors have bound Z variants, i.e. the $K_D$ concentration.

Determination of the affinity constant for selected Z variants to IFG1R over-expressing cells: To quantify the affinity constant of the Z variants for the IGF-1R over-expressing cell line MCF-7, serial dilutions of biotinylated Z variants as well as IGF-1 were used to stain cells, followed by detection with a neutravidin-FITC/anti-FITC antibody sandwich, which in turned was followed by determination of cellular fluorescence by flow cytometry. The measured fluorescence was plotted against the logarithmic concentration of the Z variant or IGF-1 used during the staining (FIG. 5). The measured points were fitted to a sigmoidal curve where the inflection point corresponds to a state where half the number of available receptors in the system are occupied. The concentration of Z variant or IGF-1 at this point corresponds to the dissociation concentration. The values obtained were 1.2 nM for Z01781, 805 nM for Z01999, 1934 nM for Z02008 and 3.6 nM for IGF-1.

Figure 6:
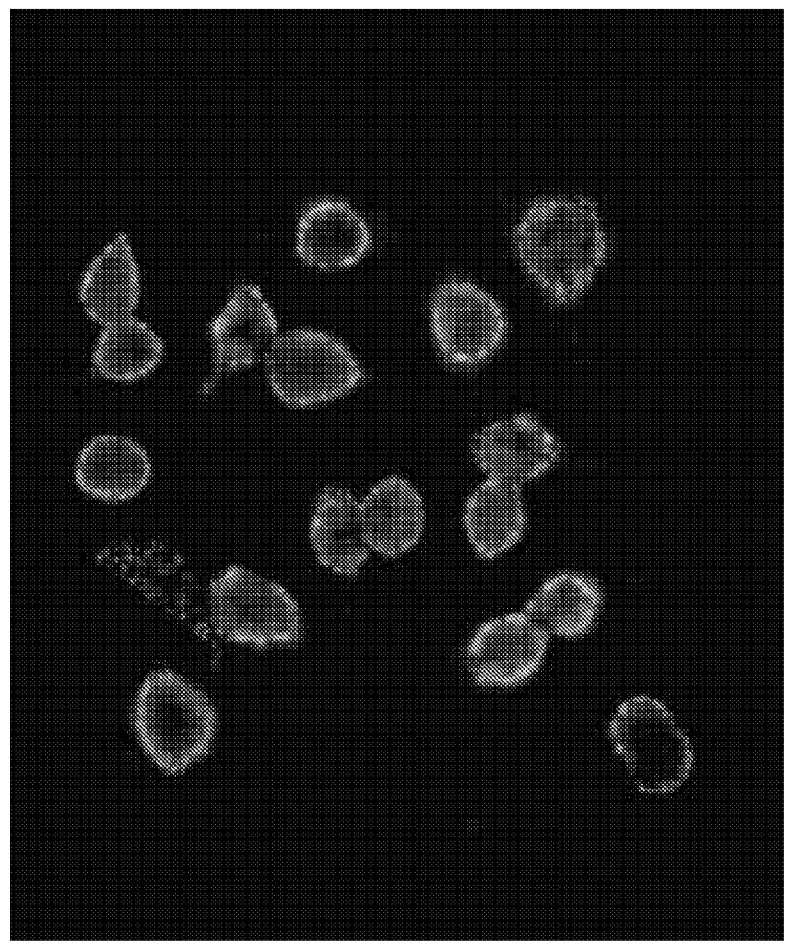
FIG. 6 shows the result of fluorescent microscopic analysis of MCF-7 cells stained with the IGF-1R binding Z variant Z01781.

Immunofluorescence: IGF-1R, expressed on the membrane of the human breast carcinoma cells MCF-7, was detected by immunofluorescence staining using the Z variant Z01781. The results are shown in FIG. 6. The picture shows strong immunofluorescence staining of membrane localized IGF-1R on MCF-7 cells.

EXAMPLE 2

Phage display selection of additional IGF-1R binding polypeptides

Materials and Methods

Library design: Based on the results of the selection experiments described in Example 1, a new phage display library of Z variants was constructed. In the new library, 14 variable positions in the Z molecule scaffold were biased towards certain amino acid residues, according to a strategy based on the Z variant sequences defined by SEQ ID NO:198-204. A degenerated oligonucleotide encoding the possible variants was obtained from Scandinavian Gene Synthesis AB and denoted AFFI-1300. The theoretical frequencies and distributions of amino acid residues in the new library for the 14 variable Z positions are given in Table 1.

TABLE 1

Frequencies and distribution of amino acids in varied positions

| Amino acid | X2 | X3 | X4 | X6 | X7 | X10 | X11 | X16 | X17 | X18 | X20 | X21 | X25 | X28 | Amino acid |
|---|---|---|---|---|---|---|---|---|---|---|---|---|---|---|---|
| Ala (A) | 16 | 0.0 | 0.0 | 49 | 0 | 0 | 20 | 0 | 1 | 1 | 1 | 12 | 12 | 10 | Ala (A) |
| Arg (R) | 6 | 0.0 | 0.0 | 1.25 | 0 | 0 | 6 | 0 | 26 | 26 | 26 | 16 | 16 | 6 | Arg (R) |
| Asn (N) | 2 | 2.4 | 2.4 | 1.75 | 0 | 0 | 4 | 50 | 12.5 | 12.5 | 12.5 | 6 | 6 | 12 | Asn (N) |
| Asp (D) | 8 | 2.4 | 2.4 | 4.9 | 0 | 0 | 3.2 | 0 | 2.5 | 2.5 | 2.5 | 3 | 3 | 15 | Asp (D) |
| Cys (C) | 0 | 0.0 | 0.0 | 0 | 0 | 0 | 0 | 0 | 0 | 0 | 0 | 0 | 0 | 0 | Cys (C) |
| Gln (Q) | 0 | 0.1 | 0.1 | 0.15 | 0 | 0 | 0.2 | 0 | 10 | 10 | 10 | 1 | 1 | 3 | Gln (Q) |
| Glu (E) | 8 | 0.1 | 0.1 | 2.1 | 0 | 0 | 0.8 | 0 | 2.5 | 2.5 | 2.5 | 3 | 3 | 15 | Glu (E) |
| Gly (G) | 48 | 0.0 | 0.0 | 7 | 0 | 0 | 12 | 0 | 4 | 4 | 4 | 12 | 12 | 10 | Gly (G) |
| His (H) | 0 | 2.4 | 2.4 | 0.35 | 0 | 0 | 0.8 | 0 | 10 | 10 | 10 | 1 | 1 | 3 | His (H) |
| Ile (I) | 0 | 2.4 | 2.4 | 1.75 | 20 | 20 | 4 | 0 | 0 | 0 | 0 | 0 | 0 | 0 | Ile (I) |
| Leu (L) | 0 | 4.6 | 4.6 | 0.5 | 20 | 20 | 1 | 0 | 0 | 0 | 0 | 0 | 0 | 0 | Leu (L) |
| Lys (K) | 2 | 0.1 | 0.1 | 0.75 | 0 | 0 | 1 | 0 | 12.5 | 12.5 | 12.5 | 6 | 6 | 12 | Lys (K) |
| Met (M) | 0 | 0.1 | 0.1 | 0.75 | 20 | 20 | 1 | 0 | 0 | 0 | 0 | 0 | 0 | 0 | Met (M) |
| Phe (F) | 0 | 40.4 | 40.4 | 0 | 20 | 20 | 0 | 0 | 0 | 0 | 0 | 0 | 0 | 0 | Phe (F) |
| Pro (P) | 0 | 0.0 | 0.0 | 3.5 | 0 | 0 | 5 | 0 | 4 | 4 | 4 | 4 | 4 | 2 | Pro (P) |
| Ser (S) | 6 | 0.0 | 0.0 | 1.75 | 0 | 0 | 12 | 0 | 10 | 10 | 10 | 12 | 12 | 4 | Ser (S) |
| Thr (T) | 4 | 0.0 | 0.0 | 17.5 | 0 | 0 | 25 | 50 | 5 | 5 | 5 | 24 | 24 | 8 | Thr (T) |

TABLE 1-continued

Frequencies and distribution of amino acids in varied positions

| Amino acid | X2 | X3 | X4 | X6 | X7 | X10 | X11 | X16 | X17 | X18 | X20 | X21 | X25 | X28 | Amino acid |
|---|---|---|---|---|---|---|---|---|---|---|---|---|---|---|---|
| Trp (w) | 0 | 0.0 | 0.0 | 0 | 0 | 0 | 0 | 0 | 0 | 0 | 0 | 0 | 0 | 0 | Trp (w) |
| Try (Y) | 0 | 40.4 | 40.4 | 0 | 0 | 0 | 0 | 0 | 0 | 0 | 0 | 0 | 0 | 0 | Try (Y) |
| Val (V) | 0 | 2.5 | 2.5 | 7 | 20 | 20 | 4 | 0 | 0 | 0 | 0 | 0 | 0 | 0 | Val (V) |
| Stop (.) | 0 | 2.1 | 2.1 | 0 | 0 | 0 | 0 | 0 | 0 | 0 | 0 | 0 | 0 | 0 | Stop (.) |

Library construction: The degenerated oligonucleotide AFFI-1300 (5'-ctcgaggtagacaacaaattcaacaaa-gaannkrrstgggcgctgrbygagatckkgnnkttacctaacttaaa csagyr-scaatggnnkgccttcatcnnkagtttamrwgatgacccaagccaaagc) was amplified by PCR using 0.1 pmol template, 50 pmol AFFI-50 (5'-cccccctgctagcaagttagcgctttgg-cttgggtcatc) and AFFI-976 (5'-cccccccccctcgaggtagacaacaaattcaa) primers, 2 mM dNTP mix, 2.5 U AmpliTaq Gold polymerase (Applied Biosystems #4311816), 1×PCR buffer (Applied Biosystems #N8080006). Primers AFFI-50 and AFFI-976 included restriction sites for NheI and XhoI, respectively. Ninety-six PCR reactions à 50 µl were performed on a Mastercycler epgradient S (Eppendorf), using the program: 10 min @ 95° C., 20 cycles of (20 s @ 95° C., 30 s @ 50° C., 60 s @ 72° C.] and 10 min @ 72° C. The amplified fragments were cleaved by 2 h incubation at 37° C. with 650 U NheI (New England Biolabs #R0131M) and 60 U XhoI (New England Biolabs #R0146), BSA (New England Biolabs #B9001S) and NEB2 buffer (New England Biolabs #B7002S). The cleaved fragments were concentrated and purified using QIAquick PCR Purification Kit (Qiagen) and size exclusion separation on 1% agarose gel followed by purification with QIAquick Gel Extraction Kit (Qiagen).

When ligated to a Z variant fragment, phagemid vector pAY00065 encodes the construct Z-ABD-pIII, comprising the Z variant fused to the albumin binding domain GA3 of protein G from *Streptococcus* strain G148 (ABD), in turn fused to the phage coat protein pIII; with the proviso that the pIII fusion domain is not present unless an amber suppressor host is used for expression, due to the presence of an amber stop codon between the ABD and pIII encoding portions. The vector is also denoted pAffi1 and described in Grönwall et al, J Biotechnol 128:162-183, 2007. Ligation of 20 µg phagemid vector pAY00065 and 3.2 µg fragment was performed in 2 h incubation with T4 DNA ligase (New England Biolabs). The ligation was subjected to a standard DNA extraction using phenol:chloroform:isoamylalcohol (25:24:1, Invitrogen #15593-031) and chloroform:isoamylalcohol (24:1, Sigma C0549-1 PT) followed by ethanol precipitation. The ligation reactions were transformed into electrocompetent *Escherichia coli* RR1ΔM15 cells (Rüther, Nucleic Acids Res 10:5765-5772, 1982) followed by immediate incubation in SOC medium (tryptic soy broth 30 g/l, yeast extract 5 g/l, 1 mM MgCl₂, 1 mM MgSO₄, 1 mM NaCl, 0.25 mM KCl and 1 glucose) at 37° C. for 50 min. The transformed cells were amplified over night in three 5 l cultivation flasks containing 1000 ml tryptic soy broth and yeast extract (TSB-YE), 2% glucose and 100 mg/ml ampicillin, by incubation at 37° C. and 80 rpm. The cells were stored at −80° C. in 40% glycerol as a glycerol stock. The size of the library was determined by titration.

Preparation of phage stock: Cells from the Glycerol Stock Containing the phagemid vector were grown in TSB-YE supplemented with 2% glucose and 100 mg/ml ampicillin at 37° C. and 80 rpm, starting at an optical density (OD) of 0.1.

When the cells reached log phase (at OD 0.5-0.8), the same amount of cells as initially inoculated was infected using a 10× excess of M13K07 helper phage (New England Biolabs) and incubated for 20 min at 37° C. The infected cells were harvested at 2500 g for 10 min at room temperature. The pellet was re-suspended and incubated over night at 30° C. and 90 rpm in TSB-YE containing 100 µg/ml ampicillin, 25 µg/ml kanamycin and 0.1 mM isopropyl-β-D-thiogalactopyranoside (IPTG).

Precipitation of phage particles: In order to separate phage particles from *E. coli* cells, the phage particle cultivation was spun in a centrifuge for 10 min at 3300 g. Phage particles were precipitated by adding ⅕ volume 20% PEG in 2.5 M NaCl and incubating for 1 h on ice. The precipitation was pelleted 30 min at 10700 g at 4° C. The pellet was re-suspended in sterile H₂O and precipitated once more by adding ⅕ volume 20% PEG in 2.5 M NaCl and incubating for 45 min on ice. The precipitation was spun for 30 min at 17500 g at 4° C. and the pellet containing phages was re-suspended in phosphate buffered saline (PBS: 10 mM phosphate, 2.68 mM KCl, 137 mM NaCl, pH 7.4) with 0.1% Tween (PBST 0.1) and 0.1 gelatine. Remaining cells and cell debris were spun down and the supernatant was filtered using a 0.45 µm filter. Phage particles were stored for short term at 4° C. and for long term at −80° C. in 50% glycerol.

Biotinylation of target protein: Recombinant human IGF-1R(R&D Systems #391-GR) in PBS was biotinylated with a 10× molar excess of Sulfo-NHS-LC-Biotin (Pierce #21327) under 30 min incubation at room temperature. In order to remove any excess biotin, a buffer exchange was made on spin columns (Pierce #89849) pre-equilibrated with PBS according to the manufacturer's instructions. The biotinylated IGF-1R was stored at 4° C.

Figure 7:
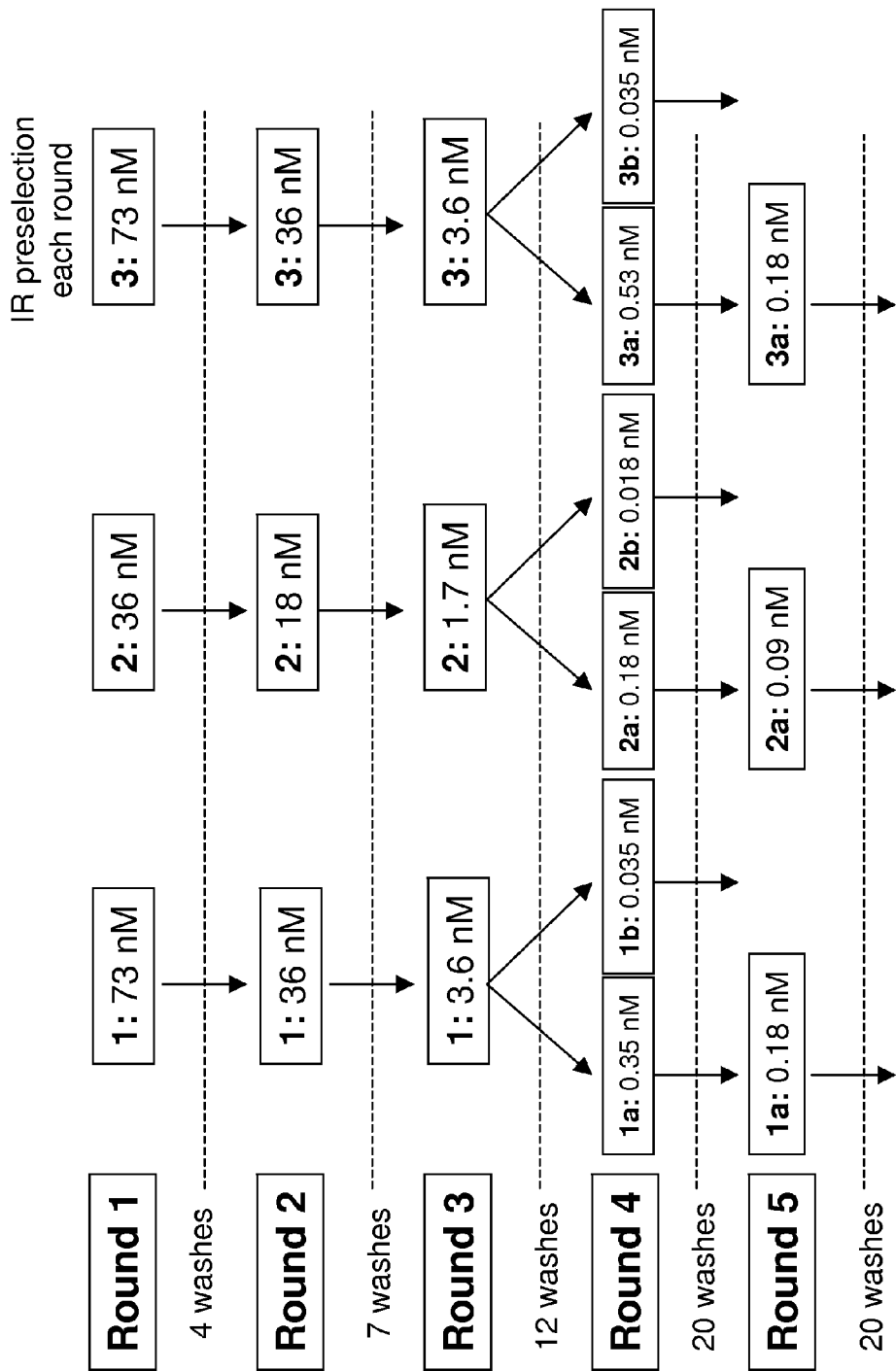
FIG. 7 is an overview of the IGF-1R selection described in Example 2, showing target concentrations and number of washes. Track 1 (divided into tracks 1a and b in round 4): High target protein concentration. Track 2 (divided into tracks 2a and b in round 4): Low target protein concentration. Track 3 (divided into tracks 3a and b in round 4): High target protein concentration, and pre-selection against IR preceding each round.
Figure 9:
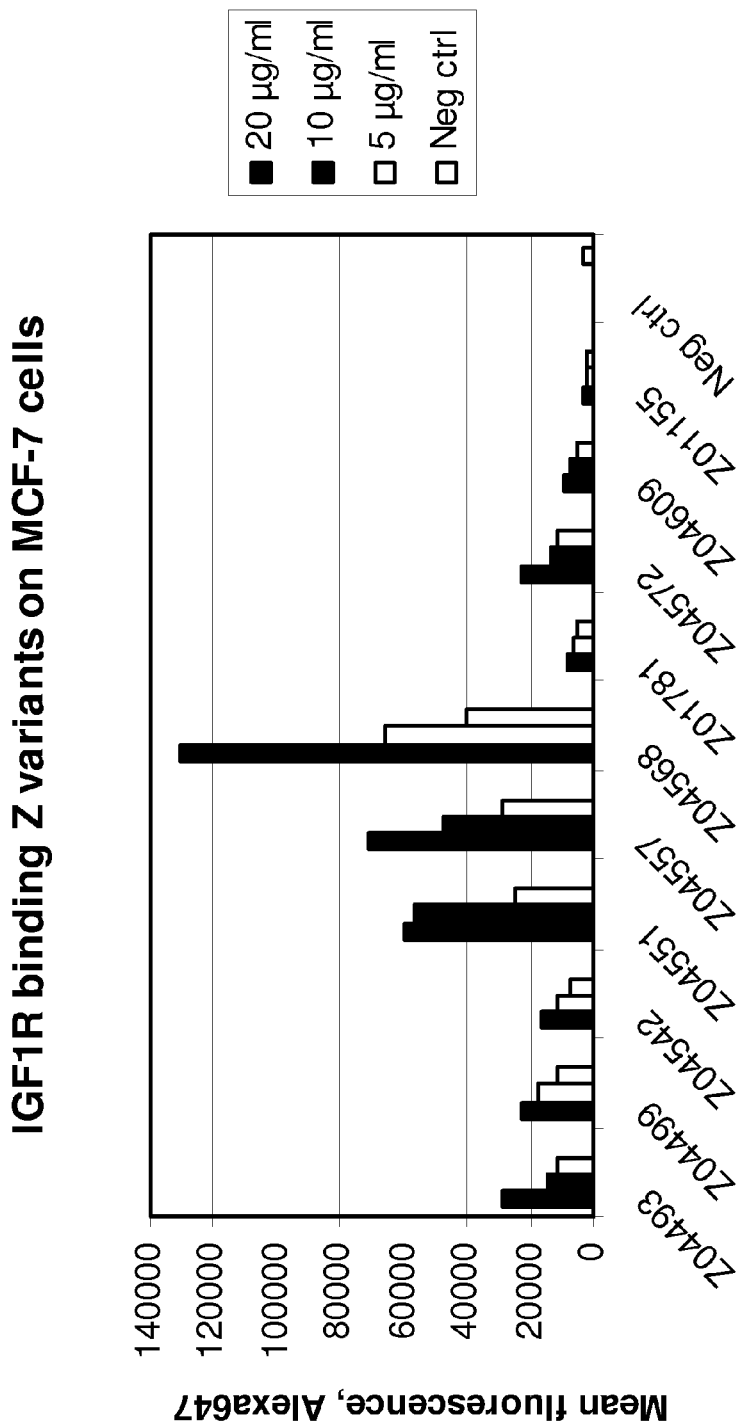
FIG. 9 shows the result of the experiment described in Example 5, i.e. flow cytometry analysis of MCF-7 cells stained with the ten indicated Z variants in 3 different concentrations. Mean fluorescence of 20000 cells is shown. "Neg ctrl" (negative control) corresponds to goat IgG and Alexa647 anti-goat only.

Phage display—General strategy: The selection was performed in 5 rounds initially divided into 3 tracks. In round 4, these were further divided into 6 tracks (see FIG. 7 for an overview). In each round, the target protein concentration was decreased and the number of washes was increased, making the selection more stringent. Preceding the first round, a pre-selection against streptavidin was made on all phages entering the selection. In track 3, which was subdivided into tracks 3a and 3b in round 4, pre-selection was made against the insulin receptor (IR) before each selection round. The selection was performed in liquid phase, and complexes of target bound to phage were captured on streptavidin coated magnetic beads (Dynabeads® M-280, Invitrogen).

Phage display—Selection: All tubes used in the selection were pre-incubated in selection buffer (PBST 0.1 with 0.1% gelatine) to avoid nonspecific binding to plastic. The streptavidin coated beads that were used to capture the target protein-phage complex after selection were also pre-incubated in selection buffer in order to avoid nonspecific binding to the beads.

A volume of phage stock corresponding to 100 copies per Z variant was used in the selection. The phage stock was precipitated with PEG/NaCl as described above to remove glycerol. The pre-selection against streptavidin coated beads was performed by incubating the phages rotating at room temperature for 1 h with 1 mg washed (2× in PBST 0.1) beads in PBST 0.1 in a total volume of 1 ml. The pre-selection against streptavidin was only performed before the first selection round.

Pre-selection against IR done in selection track 3 (divided into tracks 3a and 3b in round 4) was done by incubating a high binding tube (Nunc ImmunoTube) with a coating solution containing 60 pmol IR(R&D Systems #1544-IR) in 50 mM carbonate buffer pH 9.6 at 37° C. for 1 h or at 4° C. over night. The coating solution was discarded and the phages incubated rotating in the IR coated tube for 1 h at room temperature. In round 5, track 3a, 6.25 µg IR was also present during the selection.

Pre-selected phages and biotinylated target protein were diluted in selection buffer to a total volume of 1 ml. Selection took place in a blocked tube incubated in an end-over-end rotator for 1 h 45 min at room temperature. To capture the phage-protein complexes, the selection solution was incubated for an additional 15 min with dry streptavidin beads. Unbound phages were removed by washing with 1 ml PBST 0.1 according to the selection scheme in FIG. 7. Bound phages were eluted using a low pH strategy where 500 µl of 50 mM glycine-HCl pH 2.2 was added to the streptavidin beads. After 10 min incubation at room temperature, the solution was neutralized by addition of 450 µl PBS and 50 µl 1 M Tris-HCl, pH 8.

Phage display—Phage particle titration: The concentrations of phages entering selections as well as phages eluted after selections were determined by titration in each round. *E. coli* RR1ΔM15 cells in log phase were infected by phage particles in serial dilutions. After 5 min incubation, 5 µl cultivation from each dilution step was transferred to Tryptone yeast extract plates (TYE plates: 10 g/l Tryptone (Merck), 5 g/l yeast extract (Merck), 100 µg/ml ampicillin, 3 mg/ml NaCl and 2% glucose) and incubated at 37° C. over night. The titer was calculated from the number of colonies formed. If a subsequent round was started before the results of the titer from previous round was available, the amount of phages was calculated by an estimation that 1 ml over night culture gives rise to 1×10" cfu.

Phage display—Amplification of phage particles: Log phase *E. coli* RR1ΔM15 cells were infected with 950 µl eluted phage particles for 20 min at 37° C. The cells were pelleted for 10 min at 3300 g and the pellet was re-suspended in TSB, distributed on TYE plates and incubated over night at 37° C.

The cells from the TYE plates were re-suspended in TSB-YE medium and the concentration was determined by optical density measurement. In an attempt to make sure that all phage variants were represented, a 1000× excess with respect to phage output titration was inoculated to TSB-YE containing 2% glucose and 100 µg/ml ampicillin. Culture volume was adjusted to a starting $OD_{600}$ of approximately 0.1 and incubated at 37° C. and 90 rpm until log phase was reached. The same amount of cells as inoculated before, using an assumption that OD=1 corresponds to $5×10^8$ cells, was infected with a 10× excess of M13K07 helper phages for 30 min at 37° C. The cells were pelleted in a centrifuge for 10 min at 3300 g and the pellet was re-suspended in TSB-YE medium containing 100 µg/ml ampicillin and 50 µg/ml kanamycin, and 0.1 mM IPTG to induce the production of Z variant molecules. The culture was incubated over night at 37° C. and 90 rpm. The phage particles were harvested by precipitation as described earlier.

Screening of selected Z variants: From rounds 4 and 5, 744 randomly picked colonies were inoculated and grown over night at 37° C. and 200 rpm in deep well plates containing 1 ml TSB-YE supplemented with 100 µg/ml ampicillin and 1 mM IPTG. After the over night incubation, replica plates were made by transferring a fraction of the cells to square well storage plates with 15% glycerol for storage at −20° C. The deep well plates were spun for 10 min at 3000 g, the supernatant was discarded and the pellets were re-suspended in 400 µl PBST 0.1. The plates were frozen over night at −80° C. and thawed to release the Z variant molecules in the periplasmic fraction of the cells. The plates were spun for 15 min at 3700 g, after which the supernatants could be utilized for ELISA screening.

ELISA characterization of selected Z variants: Half area 96 well ELISA plates (Costar #3690) were coated over night at 4° C. with 50 µl, 1 µg/ml IGF-1R in 50 mM carbonate buffer, pH 9.6. The plates were rinsed in tap water and blocked with 0.5% casein in PBST 0.1 for 1 h at room temperature. The blocking solution was discarded and 50 µl of Z variant containing periplasmic solution was added. After incubation with supernatants, the plates were washed in 4×175 µl PBS with 0.05% Tween (PBST 0.05) using a Skan Washer 300 (Skatron) washing system. 50 µl IgG rabbit antibody directed against all Z variants (0.7 mg/ml, produced in-house by Affibody AB) and diluted 1:5000 was added and incubated for 2 h. The plates were washed as described above and 50 µl anti-IgG-rabbit-HRP (Dako #P0448) diluted 1:5000 was added and incubated for 1 h. A commercial IGF-1R antibody (Abcam ab32823-100) detected with a commercial secondary antibody conjugated with HRP (Jackson #703-036-155) was utilized as a positive control. After washing, 50 µl ImmunoPure TMB substrate (Pierce #34021) was added and incubated for 10 min in darkness before the reaction was stopped by addition of 50 ml 2 M sulphuric acid and absorbance measured at 450 nm in an ELISA reader Tecan Ultra 384 (Tecan Group LTD) and evaluated with Magellan v. 5.0 software (Tecan).

Sequencing: From the ELISA screening, individual clones were picked for sequencing based on absorbance values. The Z variant inserts from the pAY00065 vector were amplified by PCR by adding cells from individual clones to 1×PCR buffer with $MgCl_2$ (Applied Biosystems #8080006), 0.4 µM dNTP mix (Applied Biosystems #N8080260) and 0.1 µM AmpliTaq Gold DNA polymerase (Applied Biosystems #4311816) and 5 pmol Affi21 (5'-tgcttccggctcgtatgttgtgtg) and Affi22 (5'-cggaaccagagccaccaccgg) primers. The PCR program, performed on a Mastercycler epgradient S (Eppendorf), was 10 min @ 96° C., 30 cycles of [15 s @ 96° C., 30 s @ 55° C., 90 s @ 72° C.] and 7 min @ 72° C.

A new PCR plate was prepared with 5 pmol Affi72 biotinylated primer (biotin-5'-cggaaccagagccaccaccgg) and Big Dye Terminator v.3.1 Cycle sequencing Kit (Applied Biosystems) to which 1 µl of the amplified inserts was added and 30 cycles of [30 s @ 96° C., 15 s @ 55° C., 60 s @ 60° C.] were run. The biotinylated PCR sequence products were purified on a Magnatrix 8000 workstation using streptavidin Dynabeads® REGEN (Magnetic Biosolution #11103). Sequencing of the purified fragments was performed on an ABI Prism® 3130 xl Genetic Analyzer (Applied Biosystems).

Results

Construction of a new phagemid library: The new library was designed based on a primary set of IGF-1R-binding Z variants with verified cell binding properties. The design of the new library resulted in a theoretical size of $1×10^8$ different Z variant molecules. The actual size of the library, determined by titration after transformation to *E. coli* RR1ΔM15 cells, was 2.6×10⁸ transformants, thus covering the estimated number of unique variants in the new library. From sequencing of 96 of the clones in the obtained maturated library, correspondence with the library design was confirmed.

Phage display selection: Phage display selections were performed against IGF-1R from the new library of Z variant molecules. The selection was performed in 5 rounds where the tracks differed in target concentration and pre-selection as follows; one with high target concentration, one with low target concentration and one with high target concentration and pre-selection against IR. In round 4, the 3 tracks were divided in two tracks respectively, resulting in 6 tracks in total where tracks 1b, 2b and 3b involved rather harsh selection conditions with low target concentrations and several washes, including one over night wash. Phages eluted from these tracks were too few to continue on a fifth selection round. On the other hand, the amounts of phages eluted from tracks 1a, 2a and 3a in round 4 were sufficient to proceed to a fifth selection round.

ELISA: A direct ELISA was utilized to screen for IGF-1R binders among 352 of the clones derived from the selections. Four negative controls for the Z variant ELISA were applied, two where the Z variant was excluded, one where the primary antibody was excluded and one where the secondary antibody was excluded. A commercial IGF-1R antibody detected with a commercial secondary antibody conjugated with HRP was utilized as a positive control for the IGF-1R coating in two wells. Negative controls were also included, one omitting the primary antibody and one omitting the secondary antibody. Nearly all the screened clones demonstrated affinity for IGF-1R with low background signals at this concentration.

Sequencing: Sequencing of clones analyzed by ELISA resulted in 195 unique sequences, one clone of which appeared twice. 190 unique clones were considered positive in the ELISA experiment, defined as for example an absorbance value of above 0.4. The predicted amino acid sequences of the corresponding polypeptides and their IGF-1R binding motifs were deduced, which yielded a number of sequences of IGF-1R binding polypeptides according to the invention. The obtained sequences all corresponded to the design of the library with regard to the amino acid residues allowed in each variable position. As in Example 1, each individual Z variant was given a unique identification number #####, and individual variants are referred to as Z#####. The amino acid sequences of deduced IGF-1R binding motifs are listed in FIG. 1A-1N and in the sequence listing as SEQ ID NO:8-197, whereas the amino acid sequences of the corresponding full-length Z variants are listed in FIG. 1A-1N and in the sequence listing as SEQ ID NO:205-394.

EXAMPLE 3

Sub-cloning and expression of a subset of IGF-1R binding polypeptides

Sub-Cloning

Gene fragments corresponding to eight of the Z variants selected in Example 2 were sub-cloned in a modified pET-T7 expression vector that included sequence encoding an N-terminal $His_6$-tag and a C-terminal Cys-residue. The IGF-1R binding Z variants were sub-cloned as monomers, and the constructs encoded by the expression vectors were

MGSSHHHHHHLQ-[Z#####]-VDC, wherein Z##### was selected from Z04493 (SEQ ID NO:249), Z04499 (SEQ ID NO:255), Z04542 (SEQ ID NO:298), Z04551 (SEQ ID NO:307), Z04557 (SEQ ID NO:312), Z04568 (SEQ ID NO:323), Z04572 (SEQ ID NO:327) and Z04609 (SEQ ID NO:363).

Expression and Purification

The eight IGF-1R-binding Z variants listed in the previous section, as well as the Z variant Z01781 from Example 1 (SEQ ID NO:197), were expressed and purified to homogeneity by IMAC using the $His_6$ tag provided in the construct. In addition, in order to block the C-terminal cystein, an aliquot of NEM conjugated Z variant molecules were produced. The identity of the Z variant molecules were confirmed by LC/MS analyses and the purity was assessed by SDS-PAGE analysis. The melting temperatures (Tm) and reversibility of folding were determined by CD spectropolarity measurements. The melting temperatures ranged from 48 to 62° C. and the molecules in general folded back to the three helical bundle structure when the temperature was lowered from 90° C. to 20° C.

EXAMPLE 4

Elisa Assessment of Expressed IGF-1R Binding Polypeptides

Materials and Methods

Microtiter plate (Costar #3690) wells were coated with 3 μg/ml IGF-1R, 50 μl/well, in 50 mM carbonate buffer, pH 9.6, and incubated at 4° C. over night. The wells were blocked with phosphate buffered saline (PBS: 10 mM phosphate, 2.68 mM KCl, 137 mM NaCl, pH 7.4) supplemented with 0.5% casein (PBSC) during 1 h at room temperature. After removal of blocking, 100 ml of 400 ng/ml of the Z variant molecules Z01781, Z04499, Z04542, Z04551, Z04493, Z04557, Z04568, Z04572, Z04609 (all produced according to Example 3) and Z00810 (a Z variant molecule with affinity for an unrelated target; used as negative control), bearing an N-terminal hexa-histidine tag and a C-terminal cysteine (NEM), were diluted in PBSC and added in triplicates to column 1 of the microplate. Columns 2-12 were filled with 50 μl PBSC. The Z variants were diluted stepwise 1:2 from column 1 to 11, leaving 50 μl of diluted Z variant molecule in each well. The plates were then incubated for 1.5 h at room temperature.

A goat IgG antibody against an epitope common to all Z variants (developed in house by Affibody AB) was diluted to 1.5 μg/ml in PBSC, 50 μl were added to each well, and incubated for 1.5 h. Complexes of Z variants and goat IgG were detected with 50 μl rabbit anti-goat IgG conjugated with HRP (SIGMA P0449) diluted 1:5000 in PBSC and incubated for 1 h at room temperature. The plates were washed four times with PBS with 0.05% Tween (PBST0.05) before incubation with primary and secondary antibody. Developing solution was prepared by mixing an equal volume of ImmunoPure TMB substrate solution (Thermo Scientific #34021) A and B and 50 μl were added to each well. After 20 min incubation, 50 μl 2 M $H_2SO_4$ were added and the plates were read at 450 nm in an ELISA reader (Tecan Ultra 384, Tecan Group Ltd) and evaluated with Magellan v. 5.0 software (Tecan).

As described above, a negative control, the Z variant Z00810, was used in the same set up as the IGF-1R specific Z variants.

Curves were plotted in Microsoft Excel, and EC50 values were calculated using the log(agonist) vs. response (Variable slope) model, setting the bottom value to 0, using GraphPad software (GraphPad Software Inc.).

Results

Dose response curves were created for 9 Z variant molecules using an ELISA assay. IGF-1R was coated in microplate wells and Z variants were allowed to bind to the target. Bound Z variants were detected with specific antibodies. The dose response curves are presented as FIGS. 8A-8E, and clearly show specific binding of all tested IGF-1R binding polypeptides to IGF-1R. As expected, there is no binding by the negative control Z00810.

EC50 values, i.e the concentration of Z variant that provokes a response halfway between the baseline (bottom) and maximum response (top), were calculated for the IGF-1R binding Z variants using the log(agonist) vs. response (variable slope) model with the GraphPad software. The results are shown in Table 2.

TABLE 2

EC50 values for IGF-1R binding Z variants based on dose response curves with the bottom line set to 0

| Molecule | EC50 (ng/ml) |
|---|---|
| Z01781 | 15.0 |
| Z04493 | 16.2 |
| Z04499 | 13.4 |
| Z04542 | 13.1 |
| Z04551 | 23.8 |
| Z04557 | 20.5 |
| Z04568 | 33.6 |
| Z04572 | 21.3 |
| Z04609 | 16.7 |

EXAMPLE 5

Flow Cytometry Analysis of Expressed IGF-1R Binding Polypeptides

Materials and Methods

The Z variant molecules Z01781, Z04499, Z04542, Z04551, Z04493, Z04557, Z04568, Z04572, Z04609 (all produced according to Example 3) and Z01155 (a Z variant molecule with affinity for an unrelated target; used as negative control), bearing an N-terminal hexa-histidine tag and a C-terminal cysteine, were tested.

300000 MCF-7 cells (ATCC HTB-22) per tube were incubated with 100 μl of Z variant diluted to 20, 10 and 5 μg/ml in ice cold PBS+0.1% BSA. After one hour on ice, the cells were washed twice in ice cold PBS and incubated with a goat IgG antibody directed towards an epitope common for all Z variants, 5 μg/ml diluted in ice cold PBS+0.1% BSA, for one hour on ice. The cells were washed again and Alexa647 chicken anti-goat antibody (Molecular Probes A21469) was added, diluted in ice cold PBS+0.1% BSA to 15 μg/ml. After one hour on ice in the dark, the cells were washed twice and analyzed in a FACS apparatus. 20000 cells per tube were analyzed.

An IGF-1R binding antibody was used in another experiment to confirm that the cells indeed do express the IGF-1 receptor. This antibody (chicken anti-human IGF-1R, α subunit; Abcam ab32823) was detected with Alexa488 anti-chicken antibody (Molecular Probes A41658). Incubations and washes were done as described above. Since this detection system differs from that of the IGF-1R binding Z variant molecules, the antibody control was excluded in further experiments.

Results

The results are shown in FIG. 9. All IGF-1R binding Z variants bound to the MCF-7 cells, and the signals from Z variants selected according to Example 2 were stronger than those from Z01781 described in Example 1. Among the Z variants from Example 2, the strongest signals were seen with Z04568, Z04557 and Z04551. Intermediate signals were seen with Z04493, Z04499 and Z04572, and the weakest signals were seen with Z04542 and Z04609. Z01781 rendered the weakest signals of all IGF-1R binding Z variants, and the signals from the unrelated variant Z01155 were similar to that of the negative control (goat anti-Z antibody and Alexa647 anti-goat antibody only).

The invention claimed is:

1. Insulin-like growth factor 1 receptor (IGF-1 R) binding polypeptide, comprising an insulin-like growth factor 1 receptor binding motif, which motif consists of an amino acid sequence selected from:

i) $EX_2X_3X_4AX_6X_7EIX_{10}X_{11}LPNLX_{16}X_{17}X_{18}QX_{20}X_{21}$-$AFIX_{25}SLX_{28}D$ (SEQ ID NO:398), wherein, independently of each other, $X_2$ is selected from G, P and K;
$X_3$ is selected from F and Y;
$X_4$ is selected from Y and F;
$X_6$ is selected from A, L, S and G;
$X_7$ is selected from I, L, M and V;
$X_{10}$ is selected from I, L and V;
$X_{11}$ is selected from T, A, S, G, L, Q, I and V;
$X_{16}$ is selected from N and T;
$X_{17}$ is selected from S, Q, H, R, N, K, P, A, D, E, G and T;
$X_{18}$ is selected from S, Q, H, R, N, K, D, P, T and G;
$X_{20}$ is selected from S, Q, H, R and W;
$X_{21}$ is selected from T, G, R, A, N, D, Q, E, K and S;
$X_{25}$ is selected from T, G, R, A, N, D, Q, E, K, H and S; and
$X_{28}$ is selected from E, N, G, S, A, T, K, P, Q and D;

and ii) an amino acid sequence which has at least 85% identity to the sequence defined in i).

2. IGF-1 R-binding polypeptide according to claim 1, wherein $X_2$ is G.

3. IGF-1 R-binding polypeptide according to claim 1, wherein $X_3$ is F.

4. IGF-1 R-binding polypeptide according to claim 1, wherein $X_4$ is Y.

5. IGF-1 R-binding polypeptide according to claim 1, wherein $X_6$ is A.

6. IGF-1 R-binding polypeptide according to claim 1, wherein $X_3X_4$ is FY and $X_6$ is A.

7. IGF-1 R-binding polypeptide according to claim 1, wherein $X_{10}$ is L.

8. IGF-1 R-binding polypeptide according to claim 7, wherein $X_2X_3X_4$ is GFY, $X_6$ is A and $X_{10}$ is L.

9. IGF-1 R-binding polypeptide according to claim 1, wherein $X_7$ is I.

10. IGF-1 R-binding polypeptide according to claim 9, wherein $X_2X_3X_4$ is GFY, $X_6X_7$ is AI and $X_{10}$ is L.

11. IGF-1 R-binding polypeptide according to claim 1, wherein $X_{16}$ is N.

12. IGF-1 R-binding polypeptide according to claim 1, wherein $X_{17}$ is H.

13. IGF-1 R-binding polypeptide according to claim 1, wherein $X_{18}$ is selected from K and S.

14. IGF-1 R-binding polypeptide according to claim 1 wherein $X_{20}$ is R.

15. IGF-1 R-binding polypeptide according to claim 1, wherein $X_{21}$ is selected from T and G.

16. IGF-1 R-binding polypeptide according to claim 1, wherein $X_{25}$ is T.

17. IGF-1 R-binding polypeptide according to claim 16, wherein $X_{20}X_{21}$ is RG and $X_{25}$ is T.

18. IGF-1 R-binding polypeptide according to claim 17, wherein $X_{11}$ is S, $X_{17}X_{18}$ is HS, $X_{20}X_{21}$ is RG and $X_{25}$ is T.

19. IGF-1 R-binding polypeptide according to claim 1, wherein $X_{28}$ is E.

20. IGF-1 R-binding polypeptide according to claim 1, wherein $X_{11}$ is A, $X_{17}X_{18}$ is RK, $X_{20}X_{21}$ is ST and $X_{28}$ is E.

21. IGF-1 R-binding polypeptide according to claim 1, wherein the amino acid sequence i) is selected from SEQ ID NO:1-197.

22. IGF-1 R-binding polypeptide according to claim 21, wherein the amino acid sequence i) is selected from SEQ ID NO:1-2, 52, 58, 101 , 110, 115, 126, 130 and 166.

23. IGF-1 R-binding polypeptide according to claim 1, in which said IGF-1 R-binding motif forms part of a three-helix bundle protein domain.

24. IGF-1 R-binding polypeptide according to claim 23, in which said IGF-1 R-binding motif essentially forms part of two alpha helices and a loop connecting them, within said three-helix bundle protein domain.

25. IGF-1 R-binding polypeptide according to claim 24, in which said three-helix bundle protein domain is selected from domains of bacterial receptor proteins.

26. IGF-1 R-binding polypeptide according to claim 25, in which said three-helix bundle protein domain is selected from domains of protein A from *Staphylococcus aureus* or derivatives thereof.

27. IGF-1 R-binding polypeptide according to claim 26, which comprises an amino acid sequence selected from:

```
                                       (SEQ ID NO: 399)
ADNNFNK-[IBM]-DPSQSANLLSEAKKLNESQAPK;

(SEQ ID NO: 400)
ADNKFNK-[IBM]-DPSQSANLLAEAKKLNDAQAPK;

(SEQ ID NO: 401)
ADNKFNK-[IBM]-DPSVSKEILAEAKKLNDAQAPK;

(SEQ ID NO: 402)
ADAQQNNFNK-[IBM]-DPSQSTNVLGEAKKLNESQAPK;

(SEQ ID NO: 403)
AQHDE-[IBM]-DPSQSANVLGEAQKLNDSQAPK;
and (SEQ ID NO: 404)
VDNKFNK-[IBM]-DPSQSANLLAEAKKLNDAQAPK;
``` wherein [IBM] is an IGF-1 R-binding motif as defined in claim 1.

28. IGF-1 R-binding polypeptide, whose amino acid sequence comprises a sequence which fulfils one definition selected from the following:
   iii) it is selected from SEQ ID NO:198-394;
   iv) it is an amino acid sequence having 89% or greater identity to a sequence selected from SEQ ID NO: 198-394.

29. IGF-1 R-binding polypeptide according to claim 28, whose amino acid sequence comprises a sequence which fulfils one definition selected from the following:
   v) it is selected from SEQ ID NO:198-199, 249, 255, 298, 307, 312, 323, 327 and 363;
   vi) it is an amino acid sequence having 89% or greater identity to a sequence selected from SEQ ID NO:198-199, 249, 255, 298, 307, 312, 323, 327 and 363.

30. IGF-1 R-binding polypeptide according to claim 1, comprising additional amino acid residues C terminally and/or N terminally with respect to said IGF-1 R-binding polypeptide.

31. IGF-1 R-binding polypeptide according to claim 30 in which the or each amino acid extension enhances binding of IGF-1 R by the polypeptide.

32. IGF-1 R-binding polypeptide according to claim 30 in which the or each amino acid extension improves production, purification, stabilization in vivo or in vitro, coupling, or detection of the polypeptide.

33. IGF-1 R-binding polypeptide according to claim 32 in which the extension comprises an albumin-binding domain, or a derivative thereof, which prolongs the half life of the IGF-1 R-binding polypeptide in applications in vivo.

34. IGF-1 R-binding polypeptide according to claim 33, in which the albumin-binding domain is domain GA3 of protein G from Streptococcus strain G148, or a derivative thereof, which prolongs the half life of the IGF-1 R-binding polypeptide in applications in vivo.

35. IGF-1 R-binding polypeptide according to claim 1, which binds to IGF-1 R such that the $K_D$ value of the interaction is at most $1 \times 10^{-6}$ M.

36. IGF-1 R-binding polypeptide according to claim 35, which binds to IGF-1 R such that the $K_D$ value of the interaction is at most $1 \times 10^{-7}$ M.

37. IGF-1 R-binding polypeptide according to claim 1, which binds to the ectodomain of IGF-1 R.

38. IGF-1 R-binding polypeptide according to claim 37 which binds to a portion of the ectodomain of IGF-1 R corresponding to SEQ ID NO:397.

39. IGF-1 R-binding polypeptide comprising a fragment of an IGF-1 R-binding polypeptide according to claim 1, which fragment retains IGF-1 R binding.

40. IGF-1 R-binding polypeptide according to claim 39 in which the fragment comprises an N terminal reduction of a polypeptide according to claim 1.

41. IGF-1 R-binding polypeptide according to claim 40 in which the N terminal reduction is by up to four amino acid residues.

42. IGF-1 R-binding polypeptide according to claim 1 in multimeric form, comprising at least two IGF-1 R-binding polypeptide monomer units, whose amino acid sequences may be the same or different.

43. IGF-1 R-binding polypeptide according to claim 42, in which the IGF-1 R-binding polypeptide monomer units are covalently coupled together.

44. IGF-1 R-binding polypeptide according to claim 42, in which the IGF-1 R-binding polypeptide monomer units are expressed as a fusion protein.

* * * * *

SEQUENCE LISTING

```
<160> NUMBER OF SEQ ID NOS: 404

<210> SEQ ID NO 1
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 1

Glu Gly Phe Tyr Ala Ala Ile Glu Ile Leu Ala Leu Pro Asn Leu Asn
 1               5                  10                  15

Arg Lys Gln Ser Thr Ala Phe Ile Ser Ser Leu Glu Asp
            20                  25

<210> SEQ ID NO 2
<211> LENGTH: 29
<212> TYPE: PRT
<213> ORGANISM: Artificial Sequence
<220> FEATURE:
<223> OTHER INFORMATION: Engineered IGF-1R binding polypeptide
```

-continued

```
<400> SEQUENCE: 2

Glu Gly Phe Tyr Ala Ala Ile Glu Ile Leu Ser Leu Pro Asn Leu Asn
1               5                   10                  15

His Ser Gln Arg Gly Ala Phe Ile Thr Ser Leu Thr Asp
            20                  25

<210> SEQ ID NO 3
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 3

Glu Lys Phe Tyr Ala Ala Ile Glu Ile Leu Ala Leu Pro Asn Leu Asn
1               5                   10                  15

Arg Lys Gln Ser Thr Ala Phe Ile Arg Ser Leu Glu Asp
            20                  25

<210> SEQ ID NO 4
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 4

Glu Pro Phe Tyr Ala Ala Met Glu Ile Leu Thr Leu Pro Asn Leu Asn
1               5                   10                  15

Asn Gly Gln Arg Arg Ala Phe Ile Thr Ser Leu Asn Asp
            20                  25

<210> SEQ ID NO 5
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 5

Glu Gly Phe Tyr Ala Ala Leu Glu Ile Ile Leu Leu Pro Asn Leu Asn
1               5                   10                  15

Pro Ser Gln Trp Thr Ala Phe Ile Thr Ser Leu Gly Asp
            20                  25

<210> SEQ ID NO 6
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 6

Glu Gly Phe Tyr Ala Ala Leu Glu Ile Leu Val Leu Pro Asn Leu Asn
1               5                   10                  15

Thr Gln Gln Arg Gly Ala Phe Ile Thr Ser Leu Ser Asp
            20                  25

<210> SEQ ID NO 7
<211> LENGTH: 29
<212> TYPE: PRT
<213> ORGANISM: Artificial Sequence
<220> FEATURE:
<223> OTHER INFORMATION: Engineered IGF-1R binding polypeptide
```

-continued

```
<400> SEQUENCE: 7

Glu Gly Phe Tyr Ala Ala Ile Glu Ile Leu Ser Leu Pro Asn Leu Asn
1               5                   10                  15

His Ser Gln Arg Gly Ala Phe Ile Thr Ser Leu Thr Asp
            20                  25

<210> SEQ ID NO 8
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 8

Glu Gly Phe Tyr Ala Ala Met Glu Ile Leu Ala Leu Pro Asn Leu Asn
1               5                   10                  15

Ser Arg Gln Ser Lys Ala Phe Ile Asn Ser Leu Thr Asp
            20                  25

<210> SEQ ID NO 9
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 9

Glu Gly Phe Tyr Ala Ala Val Glu Ile Leu Gly Leu Pro Asn Leu Asn
1               5                   10                  15

Ala Arg Gln Arg Thr Ala Phe Ile Asn Ser Leu Glu Asp
            20                  25

<210> SEQ ID NO 10
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 10

Glu Gly Phe Tyr Ala Ala Met Glu Ile Val Ile Leu Pro Asn Leu Thr
1               5                   10                  15

His Arg Gln Arg Ala Ala Phe Ile Gly Ser Leu Thr Asp
            20                  25

<210> SEQ ID NO 11
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 11

Glu Gly Phe Tyr Ala Ala Ile Glu Ile Leu Ser Leu Pro Asn Leu Thr
1               5                   10                  15

Gln Lys Gln His Thr Ala Phe Ile Gly Ser Leu Thr Asp
            20                  25

<210> SEQ ID NO 12
<211> LENGTH: 29
<212> TYPE: PRT
<213> ORGANISM: Artificial Sequence
<220> FEATURE:
<223> OTHER INFORMATION: Engineered IGF-1R binding polypeptide
```

-continued

```
<400> SEQUENCE: 12

Glu Gly Phe Tyr Ala Ala Met Glu Ile Leu Ala Leu Pro Asn Leu Asn
1               5                   10                  15

Gly Arg Gln Arg Ser Ala Phe Ile Thr Ser Leu Asn Asp
            20                  25

<210> SEQ ID NO 13
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 13

Glu Gly Phe Tyr Ala Ala Ile Glu Ile Leu Thr Leu Pro Asn Leu Asn
1               5                   10                  15

Arg Arg Gln Arg Ser Ala Phe Ile Thr Ser Leu Glu Asp
            20                  25

<210> SEQ ID NO 14
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 14

Glu Gly Phe Tyr Ala Ala Leu Glu Ile Leu Ala Leu Pro Asn Leu Asn
1               5                   10                  15

Arg Lys Gln Arg Thr Ala Phe Ile Ser Ser Leu Asp Asp
            20                  25

<210> SEQ ID NO 15
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 15

Glu Gly Phe Tyr Ala Ala Leu Glu Ile Val Ser Leu Pro Asn Leu Thr
1               5                   10                  15

Glu Arg Gln Arg Ala Ala Phe Ile Gly Ser Leu Asp Asp
            20                  25

<210> SEQ ID NO 16
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 16

Glu Gly Phe Tyr Ala Ala Val Glu Ile Val Thr Leu Pro Asn Leu Thr
1               5                   10                  15

Lys Gly Gln Arg Glu Ala Phe Ile Gly Ser Leu Gly Asp
            20                  25

<210> SEQ ID NO 17
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
-continued

<400> SEQUENCE: 17

Glu Gly Phe Tyr Ala Ala Leu Glu Ile Leu Thr Leu Pro Asn Leu Asn
 1               5                  10                  15

Thr Lys Gln His Arg Ala Phe Ile Thr Ser Leu Gly Asp
            20                  25

<210> SEQ ID NO 18
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 18

Glu Gly Phe Tyr Ala Ala Ile Glu Ile Val Ala Leu Pro Asn Leu Asn
 1               5                  10                  15

Arg Arg Gln Arg Ser Ala Phe Ile Arg Ser Leu Glu Asp
            20                  25

<210> SEQ ID NO 19
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 19

Glu Gly Phe Tyr Ala Ala Leu Glu Ile Val Ala Leu Pro Asn Leu Thr
 1               5                  10                  15

Pro Arg Gln Arg Thr Ala Phe Ile Gly Ser Leu Glu Asp
            20                  25

<210> SEQ ID NO 20
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 20

Glu Gly Phe Tyr Ala Gly Ile Glu Ile Leu Ile Leu Pro Asn Leu Asn
 1               5                  10                  15

Glu Arg Gln Arg Ala Ala Phe Ile Arg Ser Leu Ser Asp
            20                  25

<210> SEQ ID NO 21
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 21

Glu Gly Phe Tyr Ala Ala Leu Glu Ile Val Ala Leu Pro Asn Leu Thr
 1               5                  10                  15

Ser Lys Gln Arg Glu Ala Phe Ile Gly Ser Leu Gly Asp
            20                  25

<210> SEQ ID NO 22
<211> LENGTH: 29
<212> TYPE: PRT
<213> ORGANISM: Artificial Sequence
<220> FEATURE:
<223> OTHER INFORMATION: Engineered IGF-1R binding polypeptide
```

-continued

```
<400> SEQUENCE: 22

Glu Gly Phe Tyr Ala Ala Ile Glu Ile Leu Ile Leu Pro Asn Leu Asn
1               5                   10                  15

Gly Ser Gln Arg Arg Ala Phe Ile Ser Ser Leu Ala Asp
            20                  25

<210> SEQ ID NO 23
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 23

Glu Gly Phe Tyr Ala Ala Leu Glu Ile Leu Ala Leu Pro Asn Leu Asn
1               5                   10                  15

Thr Arg Gln Arg Ser Ala Phe Ile Ser Ser Leu Pro Asp
            20                  25

<210> SEQ ID NO 24
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 24

Glu Gly Phe Tyr Ala Ala Leu Glu Ile Leu Val Leu Pro Asn Leu Thr
1               5                   10                  15

Gln Arg Gln Arg Thr Ala Phe Ile Thr Ser Leu Glu Asp
            20                  25

<210> SEQ ID NO 25
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 25

Glu Gly Phe Tyr Ala Ala Ile Glu Ile Leu Thr Leu Pro Asn Leu Asn
1               5                   10                  15

Asn Arg Gln Arg Thr Ala Phe Ile Thr Ser Leu Pro Asp
            20                  25

<210> SEQ ID NO 26
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 26

Glu Gly Phe Tyr Ala Ala Val Glu Ile Leu Val Leu Pro Asn Leu Thr
1               5                   10                  15

Ser Arg Gln Arg Thr Ala Phe Ile Gly Ser Leu Thr Asp
            20                  25

<210> SEQ ID NO 27
<211> LENGTH: 29
<212> TYPE: PRT
<213> ORGANISM: Artificial Sequence
<220> FEATURE:
<223> OTHER INFORMATION: Engineered IGF-1R binding polypeptide
```

<400> SEQUENCE: 27

Glu Gly Phe Tyr Ala Ala Ile Glu Ile Leu Ala Leu Pro Asn Leu Asn
1               5                   10                  15
His Arg Gln Arg Gly Ala Phe Ile Ser Ser Leu Gly Asp
            20                  25

<210> SEQ ID NO 28
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 28

Glu Gly Phe Tyr Ala Ala Leu Glu Ile Val Ser Leu Pro Asn Leu Asn
1               5                   10                  15
Gln Arg Gln Arg Thr Ala Phe Ile Thr Ser Leu Glu Asp
            20                  25

<210> SEQ ID NO 29
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 29

Glu Gly Phe Tyr Ala Ala Ile Glu Ile Leu Thr Leu Pro Asn Leu Asn
1               5                   10                  15
Glu Arg Gln Arg Gly Ala Phe Ile Gly Ser Leu Ser Asp
            20                  25

<210> SEQ ID NO 30
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 30

Glu Gly Phe Tyr Ala Ala Leu Glu Ile Leu Ile Leu Pro Asn Leu Asn
1               5                   10                  15
Arg Asn Gln Arg Thr Ala Phe Ile Ser Ser Leu Gly Asp
            20                  25

<210> SEQ ID NO 31
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 31

Glu Gly Phe Tyr Ala Ala Ile Glu Ile Leu Thr Leu Pro Asn Leu Asn
1               5                   10                  15
Arg Arg Gln Arg Asp Ala Phe Ile Thr Ser Leu Asn Asp
            20                  25

<210> SEQ ID NO 32
<211> LENGTH: 29
<212> TYPE: PRT
<213> ORGANISM: Artificial Sequence
<220> FEATURE:
<223> OTHER INFORMATION: Engineered IGF-1R binding polypeptide

```
<400> SEQUENCE: 32

Glu Gly Phe Tyr Ala Ala Ile Glu Ile Met Ser Leu Pro Asn Leu Thr
 1               5                  10                  15

Arg Arg Gln Arg Ser Ala Phe Ile Gly Ser Leu Glu Asp
            20                  25

<210> SEQ ID NO 33
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 33

Glu Gly Phe Tyr Ala Ala Leu Glu Ile Leu Val Leu Pro Asn Leu Asn
 1               5                  10                  15

Ser His Gln Arg Ala Ala Phe Ile Ala Ser Leu Glu Asp
            20                  25

<210> SEQ ID NO 34
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 34

Glu Gly Phe Tyr Ala Gly Ile Glu Ile Leu Thr Leu Pro Asn Leu Asn
 1               5                  10                  15

Arg Arg Gln Arg Glu Ala Phe Ile Gly Ser Leu Asn Asp
            20                  25

<210> SEQ ID NO 35
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 35

Glu Gly Phe Tyr Ala Ala Val Glu Ile Leu Thr Leu Pro Asn Leu Thr
 1               5                  10                  15

Arg Arg Gln Arg Ser Ala Phe Ile Gly Ser Leu Gly Asp
            20                  25

<210> SEQ ID NO 36
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 36

Glu Gly Phe Tyr Ala Ala Ile Glu Ile Val Ala Leu Pro Asn Leu Thr
 1               5                  10                  15

Gly Lys Gln Arg Ser Ala Phe Ile Lys Ser Leu Gly Asp
            20                  25

<210> SEQ ID NO 37
<211> LENGTH: 29
<212> TYPE: PRT
<213> ORGANISM: Artificial Sequence
<220> FEATURE:
<223> OTHER INFORMATION: Engineered IGF-1R binding polypeptide
```

-continued

```
<400> SEQUENCE: 37

Glu Gly Phe Tyr Ala Ala Leu Glu Ile Val Thr Leu Pro Asn Leu Asn
1               5                   10                  15

Glu Arg Gln Arg Arg Ala Phe Ile Ala Ser Leu Thr Asp
            20                  25

<210> SEQ ID NO 38
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 38

Glu Gly Phe Tyr Ala Ala Met Glu Ile Val Ala Leu Pro Asn Leu Asn
1               5                   10                  15

Ala Arg Gln Arg Thr Ala Phe Ile Gly Ser Leu Thr Asp
            20                  25

<210> SEQ ID NO 39
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 39

Glu Gly Phe Tyr Ala Ala Leu Glu Ile Ile Thr Leu Pro Asn Leu Thr
1               5                   10                  15

His Arg Gln Gln Arg Ala Phe Ile Thr Ser Leu Glu Asp
            20                  25

<210> SEQ ID NO 40
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 40

Glu Gly Phe Tyr Ala Ala Ile Glu Ile Val Ala Leu Pro Asn Leu Thr
1               5                   10                  15

Arg His Gln Gln Arg Ala Phe Ile Asn Ser Leu Gly Asp
            20                  25

<210> SEQ ID NO 41
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 41

Glu Gly Phe Tyr Ala Ala Val Glu Ile Ile Ile Leu Pro Asn Leu Thr
1               5                   10                  15

Glu Lys Gln Arg Ser Ala Phe Ile Gly Ser Leu Gly Asp
            20                  25

<210> SEQ ID NO 42
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 42

Glu Gly Phe Tyr Ala Ala Leu Glu Ile Leu Thr Leu Pro Asn Leu Asn
1               5                   10                  15

Gln Arg Gln His Arg Ala Phe Ile Ser Ser Leu Gly Asp
            20                  25

<210> SEQ ID NO 43
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 43

Glu Gly Phe Tyr Ala Ala Leu Glu Ile Val Thr Leu Pro Asn Leu Asn
1               5                   10                  15

Arg Gln Gln Arg Asp Ala Phe Ile Ser Ser Leu Asn Asp
            20                  25

<210> SEQ ID NO 44
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 44

Glu Gly Phe Tyr Ala Ala Leu Glu Ile Ile Thr Leu Pro Asn Leu Asn
1               5                   10                  15

Ala Gln Gln Arg Arg Ala Phe Ile Gly Ser Leu His Asp
            20                  25

<210> SEQ ID NO 45
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 45

Glu Gly Phe Tyr Ala Ala Val Glu Ile Leu Val Leu Pro Asn Leu Asn
1               5                   10                  15

Lys Ser Gln Arg Asp Ala Phe Ile Gly Ser Leu Asn Asp
            20                  25

<210> SEQ ID NO 46
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 46

Glu Gly Phe Tyr Ala Ala Met Glu Ile Val Ala Leu Pro Asn Leu Asn
1               5                   10                  15

Asn Asn Gln Arg Thr Ala Phe Ile Arg Ser Leu Gly Asp
            20                  25

<210> SEQ ID NO 47
<211> LENGTH: 29
<212> TYPE: PRT
<213> ORGANISM: Artificial Sequence
<220> FEATURE:
<223> OTHER INFORMATION: Engineered IGF-1R binding polypeptide
```

-continued

```
<400> SEQUENCE: 47

Glu Gly Phe Tyr Ala Ala Met Glu Ile Leu Val Leu Pro Asn Leu Asn
1               5                   10                  15

Arg Arg Gln Arg Thr Ala Phe Ile Gly Ser Leu Gln Asp
            20                  25

<210> SEQ ID NO 48
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 48

Glu Gly Phe Tyr Ala Ala Leu Glu Ile Leu Gly Leu Pro Asn Leu Asn
1               5                   10                  15

Arg Arg Gln Arg Ser Ala Phe Ile Ser Ser Leu Glu Asp
            20                  25

<210> SEQ ID NO 49
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 49

Glu Gly Phe Tyr Ala Ala Ile Glu Ile Leu Ser Leu Pro Asn Leu Asn
1               5                   10                  15

Pro Gly Gln Arg Thr Ala Phe Ile Asn Ser Leu Glu Asp
            20                  25

<210> SEQ ID NO 50
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 50

Glu Gly Phe Tyr Ala Ala Met Glu Ile Leu Thr Leu Pro Asn Leu Asn
1               5                   10                  15

Ser Gly Gln Arg Ser Ala Phe Ile Arg Ser Leu Thr Asp
            20                  25

<210> SEQ ID NO 51
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 51

Glu Gly Phe Tyr Ala Ala Ile Glu Ile Leu Thr Leu Pro Asn Leu Thr
1               5                   10                  15

Arg Asn Gln Arg Ser Ala Phe Ile Gly Ser Leu Gly Asp
            20                  25

<210> SEQ ID NO 52
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 52

Glu Gly Phe Tyr Ala Ala Leu Glu Ile Val Ala Leu Pro Asn Leu Asn
1               5                   10                  15

Arg Arg Gln Arg Thr Ala Phe Ile Thr Ser Leu Thr Asp
            20                  25

<210> SEQ ID NO 53
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 53

Glu Gly Phe Tyr Ala Ala Ile Glu Ile Val Ala Leu Pro Asn Leu Asn
1               5                   10                  15

Arg Lys Gln Arg Ser Ala Phe Ile Arg Ser Leu Gly Asp
            20                  25

<210> SEQ ID NO 54
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 54

Glu Gly Phe Tyr Ala Ala Ile Glu Ile Val Ser Leu Pro Asn Leu Asn
1               5                   10                  15

Gly Arg Gln Arg Arg Ala Phe Ile Ser Ser Leu Gly Asp
            20                  25

<210> SEQ ID NO 55
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 55

Glu Gly Phe Tyr Ala Ala Ile Glu Ile Leu Thr Leu Pro Asn Leu Asn
1               5                   10                  15

Asn Thr Gln Arg Lys Ala Phe Ile Thr Ser Leu Gly Asp
            20                  25

<210> SEQ ID NO 56
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 56

Glu Gly Phe Tyr Ala Ala Leu Glu Ile Val Ala Leu Pro Asn Leu Asn
1               5                   10                  15

Arg Lys Gln Arg Gly Ala Phe Ile Asp Ser Leu Asn Asp
            20                  25

<210> SEQ ID NO 57
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 57

Glu Gly Phe Tyr Ala Ala Ile Glu Ile Leu Ser Leu Pro Asn Leu Asn
1               5                   10                  15

Ser Lys Gln His Arg Ala Phe Ile Asn Ser Leu Thr Asp
            20                  25

<210> SEQ ID NO 58
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 58

Glu Gly Phe Tyr Ala Ala Ile Glu Ile Leu Thr Leu Pro Asn Leu Asn
1               5                   10                  15

Ala Asn Gln Arg Thr Ala Phe Ile Gly Ser Leu Gly Asp
            20                  25

<210> SEQ ID NO 59
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 59

Glu Gly Phe Tyr Ala Ala Leu Glu Ile Val Ala Leu Pro Asn Leu Thr
1               5                   10                  15

Asn Arg Gln Arg Ser Ala Phe Ile Thr Ser Leu Glu Asp
            20                  25

<210> SEQ ID NO 60
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 60

Glu Gly Phe Tyr Ala Ala Ile Glu Ile Leu Thr Leu Pro Asn Leu Asn
1               5                   10                  15

Arg Arg Gln His Glu Ala Phe Ile Ala Ser Leu Gly Asp
            20                  25

<210> SEQ ID NO 61
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 61

Glu Gly Phe Tyr Ala Ala Met Glu Ile Leu Val Leu Pro Asn Leu Thr
1               5                   10                  15

Gln Arg Gln Arg Glu Ala Phe Ile Thr Ser Leu Asn Asp
            20                  25

<210> SEQ ID NO 62
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 62

Glu Gly Phe Tyr Ala Ala Ile Glu Ile Val Ala Leu Pro Asn Leu Asn
1               5                   10                  15

Ser Asn Gln Arg Thr Ala Phe Ile Arg Ser Leu Thr Asp
            20                  25

<210> SEQ ID NO 63
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 63

Glu Gly Phe Tyr Ala Ala Ile Glu Ile Val Ala Leu Pro Asn Leu Thr
1               5                   10                  15

Pro Arg Gln Arg Ala Ala Phe Ile Arg Ser Leu Ala Asp
            20                  25

<210> SEQ ID NO 64
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 64

Glu Gly Phe Tyr Ala Ala Leu Glu Ile Leu Ser Leu Pro Asn Leu Asn
1               5                   10                  15

Lys His Gln Arg Lys Ala Phe Ile Ser Ser Leu Glu Asp
            20                  25

<210> SEQ ID NO 65
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 65

Glu Gly Phe Tyr Ala Ala Leu Glu Ile Val Ala Leu Pro Asn Leu Asn
1               5                   10                  15

Gln Gln Gln Arg Arg Ala Phe Ile Gln Ser Leu Gly Asp
            20                  25

<210> SEQ ID NO 66
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 66

Glu Gly Phe Tyr Ala Ala Val Glu Ile Leu Ala Leu Pro Asn Leu Asn
1               5                   10                  15

Gln Arg Gln Arg Thr Ala Phe Ile Thr Ser Leu Ser Asp
            20                  25

<210> SEQ ID NO 67
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 67

Glu Gly Phe Tyr Ala Ala Ile Glu Ile Ile Ser Leu Pro Asn Leu Asn
1               5                   10                  15

Arg Arg Gln Arg Gly Ala Phe Ile Ala Ser Leu Thr Asp
            20                  25

<210> SEQ ID NO 68
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 68

Glu Gly Phe Tyr Ala Ala Leu Glu Ile Val Ala Leu Pro Asn Leu Asn
1               5                   10                  15

Ser Lys Gln Arg Arg Ala Phe Ile Thr Ser Leu Glu Asp
            20                  25

<210> SEQ ID NO 69
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 69

Glu Gly Phe Tyr Ala Ala Met Glu Ile Ile Ala Leu Pro Asn Leu Thr
1               5                   10                  15

Gln Arg Gln Arg Thr Ala Phe Ile Arg Ser Leu Glu Asp
            20                  25

<210> SEQ ID NO 70
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 70

Glu Gly Phe Tyr Ala Ala Ile Glu Ile Leu Val Leu Pro Asn Leu Asn
1               5                   10                  15

Glu Ser Gln Arg Ser Ala Phe Ile Lys Ser Leu Gly Asp
            20                  25

<210> SEQ ID NO 71
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 71

Glu Gly Phe Tyr Ala Ala Ile Glu Ile Leu Val Leu Pro Asn Leu Thr
1               5                   10                  15

Gln Ser Gln Arg Arg Ala Phe Ile Thr Ser Leu Glu Asp
            20                  25

<210> SEQ ID NO 72
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 72

Glu Gly Phe Tyr Ala Ala Leu Glu Ile Leu Thr Leu Pro Asn Leu Asn
 1               5                  10                  15

Lys Lys Gln His Arg Ala Phe Ile Asn Ser Leu Glu Asp
            20                  25

<210> SEQ ID NO 73
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 73

Glu Gly Phe Tyr Ala Ala Ile Glu Ile Leu Thr Leu Pro Asn Leu Asn
 1               5                  10                  15

Gln Arg Gln Arg Thr Ala Phe Ile Thr Ser Leu Gly Asp
            20                  25

<210> SEQ ID NO 74
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 74

Glu Gly Phe Tyr Ala Ala Met Glu Ile Leu Val Leu Pro Asn Leu Asn
 1               5                  10                  15

Ser Arg Gln Arg Asn Ala Phe Ile His Ser Leu Ser Asp
            20                  25

<210> SEQ ID NO 75
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 75

Glu Gly Phe Tyr Ala Ala Ile Glu Ile Leu Ala Leu Pro Asn Leu Asn
 1               5                  10                  15

Thr Lys Gln Arg Thr Ala Phe Ile Asn Ser Leu Glu Asp
            20                  25

<210> SEQ ID NO 76
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 76

Glu Gly Phe Tyr Ala Ala Met Glu Ile Leu Thr Leu Pro Asn Leu Asn
 1               5                  10                  15

Pro Arg Gln Arg Thr Ala Phe Ile Glu Ser Leu Thr Asp
            20                  25

<210> SEQ ID NO 77
<211> LENGTH: 29
<212> TYPE: PRT
<213> ORGANISM: Artificial Sequence
<220> FEATURE:
<223> OTHER INFORMATION: Engineered IGF-1R binding polypeptide
```

-continued

```
<400> SEQUENCE: 77

Glu Gly Phe Tyr Ala Ala Leu Glu Ile Leu Thr Leu Pro Asn Leu Asn
1               5                   10                  15

Pro Arg Gln Arg Arg Ala Phe Ile Thr Ser Leu Asp Asp
            20                  25

<210> SEQ ID NO 78
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 78

Glu Gly Phe Tyr Ala Ala Ile Glu Ile Ile Thr Leu Pro Asn Leu Asn
1               5                   10                  15

Thr Arg Gln Arg Thr Ala Phe Ile Arg Ser Leu Gly Asp
            20                  25

<210> SEQ ID NO 79
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 79

Glu Gly Phe Tyr Ala Ala Ile Glu Ile Leu Ser Leu Pro Asn Leu Asn
1               5                   10                  15

Gln Arg Gln Arg Gly Ala Phe Ile Ala Ser Leu Gly Asp
            20                  25

<210> SEQ ID NO 80
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 80

Glu Gly Phe Tyr Ala Ala Ile Glu Ile Val Thr Leu Pro Asn Leu Asn
1               5                   10                  15

Arg Arg Gln Arg Asp Ala Phe Ile Ala Ser Leu Gly Asp
            20                  25

<210> SEQ ID NO 81
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 81

Glu Gly Phe Tyr Ala Ala Met Glu Ile Leu Ile Leu Pro Asn Leu Asn
1               5                   10                  15

Gly His Gln Arg Ser Ala Phe Ile Gly Ser Leu Thr Asp
            20                  25

<210> SEQ ID NO 82
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 82

Glu Gly Phe Tyr Ala Ala Leu Glu Ile Ile Thr Leu Pro Asn Leu Thr
1               5                   10                  15

His Arg Gln His Ala Ala Phe Ile Asn Ser Leu Glu Asp
            20                  25

<210> SEQ ID NO 83
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 83

Glu Gly Phe Tyr Ala Ala Leu Glu Ile Leu Ile Leu Pro Asn Leu Asn
1               5                   10                  15

Arg Gly Gln His Ala Ala Phe Ile Arg Ser Leu Thr Asp
            20                  25

<210> SEQ ID NO 84
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 84

Glu Gly Phe Tyr Ala Ala Met Glu Ile Ile Ala Leu Pro Asn Leu Thr
1               5                   10                  15

Lys Arg Gln Arg Thr Ala Phe Ile Ser Ser Leu Ala Asp
            20                  25

<210> SEQ ID NO 85
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 85

Glu Gly Phe Tyr Ala Ala Leu Glu Ile Leu Ala Leu Pro Asn Leu Thr
1               5                   10                  15

Ser Lys Gln Arg Glu Ala Phe Ile Gly Ser Leu Gly Asp
            20                  25

<210> SEQ ID NO 86
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 86

Glu Gly Phe Tyr Ala Ser Ile Glu Ile Leu Val Leu Pro Asn Leu Asn
1               5                   10                  15

Ser Arg Gln Arg Ser Ala Phe Ile Ser Ser Leu Gly Asp
            20                  25

<210> SEQ ID NO 87
<211> LENGTH: 29
<212> TYPE: PRT
<213> ORGANISM: Artificial Sequence
<220> FEATURE:
<223> OTHER INFORMATION: Engineered IGF-1R binding polypeptide
```

-continued

```
<400> SEQUENCE: 87

Glu Gly Phe Tyr Ala Ala Ile Glu Ile Val Ala Leu Pro Asn Leu Thr
1               5                   10                  15

Arg Arg Gln Arg Ala Ala Phe Ile Ala Ser Leu Asp Asp
            20                  25

<210> SEQ ID NO 88
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 88

Glu Gly Phe Tyr Ala Ala Ile Glu Ile Leu Thr Leu Pro Asn Leu Asn
1               5                   10                  15

Gln Arg Gln Arg Gly Ala Phe Ile Asn Ser Leu Glu Asp
            20                  25

<210> SEQ ID NO 89
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 89

Glu Gly Phe Tyr Ala Ala Ile Glu Ile Ile Ala Leu Pro Asn Leu Thr
1               5                   10                  15

Gln Arg Gln His Arg Ala Phe Ile Thr Ser Leu Asn Asp
            20                  25

<210> SEQ ID NO 90
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 90

Glu Gly Phe Tyr Ala Ala Ile Glu Ile Ile Thr Leu Pro Asn Leu Thr
1               5                   10                  15

Lys Arg Gln Arg Ala Ala Phe Ile Gly Ser Leu Ser Asp
            20                  25

<210> SEQ ID NO 91
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 91

Glu Gly Phe Tyr Ala Ala Ile Glu Ile Leu Val Leu Pro Asn Leu Thr
1               5                   10                  15

Thr Arg Gln His Lys Ala Phe Ile Asn Ser Leu Gly Asp
            20                  25

<210> SEQ ID NO 92
<211> LENGTH: 29
<212> TYPE: PRT
<213> ORGANISM: Artificial Sequence
<220> FEATURE:
<223> OTHER INFORMATION: Engineered IGF-1R binding polypeptide
```

-continued

```
<400> SEQUENCE: 92

Glu Gly Phe Tyr Ala Ala Ile Glu Ile Val Ser Leu Pro Asn Leu Thr
1               5                   10                  15

Ser Arg Gln Arg Thr Ala Phe Ile His Ser Leu Gln Asp
            20                  25

<210> SEQ ID NO 93
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 93

Glu Gly Phe Tyr Ala Ala Ile Glu Ile Val Ala Leu Pro Asn Leu Asn
1               5                   10                  15

Arg Asn Gln Arg Thr Ala Phe Ile Arg Ser Leu Thr Asp
            20                  25

<210> SEQ ID NO 94
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 94

Glu Gly Phe Tyr Ala Ala Ile Glu Ile Ile Ser Leu Pro Asn Leu Asn
1               5                   10                  15

Arg Lys Gln Arg Gly Ala Phe Ile Ala Ser Leu Thr Asp
            20                  25

<210> SEQ ID NO 95
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 95

Glu Gly Phe Tyr Ala Ala Ile Glu Ile Leu Ile Leu Pro Asn Leu Asn
1               5                   10                  15

Arg Lys Gln Ser Arg Ala Phe Ile Ala Ser Leu Glu Asp
            20                  25

<210> SEQ ID NO 96
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 96

Glu Gly Phe Tyr Ala Ala Met Glu Ile Leu Ser Leu Pro Asn Leu Asn
1               5                   10                  15

Lys Arg Gln Arg Thr Ala Phe Ile Thr Ser Leu Glu Asp
            20                  25

<210> SEQ ID NO 97
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 97

Glu Gly Phe Tyr Ala Ala Ile Glu Ile Leu Val Leu Pro Asn Leu Asn
1               5                   10                  15

Gln His Gln Arg Gly Ala Phe Ile Ser Ser Leu Ser Asp
            20                  25

<210> SEQ ID NO 98
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 98

Glu Gly Phe Tyr Ala Ala Leu Glu Ile Val Ser Leu Pro Asn Leu Asn
1               5                   10                  15

Arg Asn Gln Arg Gly Ala Phe Ile Gln Ser Leu Thr Asp
            20                  25

<210> SEQ ID NO 99
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 99

Glu Gly Phe Tyr Ala Ala Met Glu Ile Ile Ser Leu Pro Asn Leu Thr
1               5                   10                  15

Lys Arg Gln Arg Arg Ala Phe Ile Thr Ser Leu Gly Asp
            20                  25

<210> SEQ ID NO 100
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 100

Glu Gly Phe Tyr Ala Ala Ile Glu Ile Val Ala Leu Pro Asn Leu Thr
1               5                   10                  15

His Lys Gln Arg Arg Ala Phe Ile Glu Ser Leu Gly Asp
            20                  25

<210> SEQ ID NO 101
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 101

Glu Gly Phe Tyr Ala Ala Leu Glu Ile Leu Ala Leu Pro Asn Leu Asn
1               5                   10                  15

His Arg Gln Arg Thr Ala Phe Ile Gly Ser Leu Glu Asp
            20                  25

<210> SEQ ID NO 102
<211> LENGTH: 29
<212> TYPE: PRT
<213> ORGANISM: Artificial Sequence
<220> FEATURE:
<223> OTHER INFORMATION: Engineered IGF-1R binding polypeptide
```

<400> SEQUENCE: 102

Glu Gly Phe Tyr Ala Ala Ile Glu Ile Leu Ser Leu Pro Asn Leu Asn
1               5                   10                  15

Arg Arg Gln Arg Thr Ala Phe Ile Gly Ser Leu Gly Asp
            20                  25

<210> SEQ ID NO 103
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 103

Glu Gly Phe Tyr Ala Ala Ile Glu Ile Leu Thr Leu Pro Asn Leu Asn
1               5                   10                  15

Ser Arg Gln Arg Asp Ala Phe Ile Gly Ser Leu Gly Asp
            20                  25

<210> SEQ ID NO 104
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 104

Glu Gly Phe Tyr Ala Ala Leu Glu Ile Val Ser Leu Pro Asn Leu Thr
1               5                   10                  15

Pro Arg Gln Arg Gly Ala Phe Ile Ser Ser Leu Gly Asp
            20                  25

<210> SEQ ID NO 105
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 105

Glu Gly Phe Tyr Ala Ala Ile Glu Ile Val Ser Leu Pro Asn Leu Asn
1               5                   10                  15

Arg Arg Gln Arg Glu Ala Phe Ile Thr Ser Leu Glu Asp
            20                  25

<210> SEQ ID NO 106
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 106

Glu Gly Phe Tyr Ala Ala Leu Glu Ile Leu Thr Leu Pro Asn Leu Thr
1               5                   10                  15

Gly Arg Gln Arg Thr Ala Phe Ile Arg Ser Leu Gly Asp
            20                  25

<210> SEQ ID NO 107
<211> LENGTH: 29
<212> TYPE: PRT
<213> ORGANISM: Artificial Sequence
<220> FEATURE:
<223> OTHER INFORMATION: Engineered IGF-1R binding polypeptide

```
<400> SEQUENCE: 107

Glu Gly Phe Tyr Ala Ala Ile Glu Ile Leu Val Leu Pro Asn Leu Asn
 1               5                  10                  15

Asn Lys Gln Arg Ser Ala Phe Ile Lys Ser Leu Asp Asp
            20                  25

<210> SEQ ID NO 108
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 108

Glu Gly Phe Tyr Ala Ala Ile Glu Ile Leu Thr Leu Pro Asn Leu Thr
 1               5                  10                  15

Ser Arg Gln His Arg Ala Phe Ile Ala Ser Leu Glu Asp
            20                  25

<210> SEQ ID NO 109
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 109

Glu Gly Phe Tyr Ala Ala Leu Glu Ile Ile Thr Leu Pro Asn Leu Asn
 1               5                  10                  15

Gln Arg Gln Arg Gln Ala Phe Ile Ala Ser Leu Gly Asp
            20                  25

<210> SEQ ID NO 110
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 110

Glu Gly Phe Tyr Ala Ala Leu Glu Ile Leu Ile Leu Pro Asn Leu Thr
 1               5                  10                  15

Gln Lys Gln Arg Gly Ala Phe Ile Ser Ser Leu Ser Asp
            20                  25

<210> SEQ ID NO 111
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 111

Glu Gly Phe Tyr Ala Ala Met Glu Ile Ile Ile Leu Pro Asn Leu Thr
 1               5                  10                  15

Pro Arg Gln Arg Ala Ala Phe Ile Thr Ser Leu Glu Asp
            20                  25

<210> SEQ ID NO 112
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 112

Glu Gly Phe Tyr Ala Ala Ile Glu Ile Leu Val Leu Pro Asn Leu Asn
1               5                   10                  15

Ser Lys Gln Arg Thr Ala Phe Ile Ala Ser Leu Ser Asp
            20                  25

<210> SEQ ID NO 113
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 113

Glu Gly Phe Tyr Ala Ala Val Glu Ile Leu Gly Leu Pro Asn Leu Asn
1               5                   10                  15

Arg Lys Gln Arg Ser Ala Phe Ile Ala Ser Leu Asp Asp
            20                  25

<210> SEQ ID NO 114
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 114

Glu Gly Phe Tyr Ala Ala Ile Glu Ile Leu Ala Leu Pro Asn Leu Asn
1               5                   10                  15

Gly Gly Gln Arg Ser Ala Phe Ile Arg Ser Leu Glu Asp
            20                  25

<210> SEQ ID NO 115
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 115

Glu Gly Phe Tyr Ala Ala Ile Glu Ile Leu Thr Leu Pro Asn Leu Thr
1               5                   10                  15

Asn Lys Gln Arg Arg Ala Phe Ile Gly Ser Leu Glu Asp
            20                  25

<210> SEQ ID NO 116
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 116

Glu Gly Phe Tyr Ala Ala Leu Glu Ile Leu Ile Leu Pro Asn Leu Asn
1               5                   10                  15

Asp Arg Gln Arg Arg Ala Phe Ile Gly Ser Leu Asn Asp
            20                  25

<210> SEQ ID NO 117
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 117

Glu Gly Phe Tyr Ala Ala Leu Glu Ile Val Thr Leu Pro Asn Leu Asn
1               5                   10                  15

Pro Lys Gln Arg Ser Ala Phe Ile Ser Ser Leu Ser Asp
            20                  25

<210> SEQ ID NO 118
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 118

Glu Gly Phe Tyr Ala Ala Ile Glu Ile Leu Ser Leu Pro Asn Leu Asn
1               5                   10                  15

Ser Arg Gln Arg Gln Ala Phe Ile Gly Ser Leu Glu Asp
            20                  25

<210> SEQ ID NO 119
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 119

Glu Gly Phe Tyr Ala Ala Leu Glu Ile Val Ile Leu Pro Asn Leu Asn
1               5                   10                  15

Thr Arg Gln Arg Asp Ala Phe Ile Arg Ser Leu Ala Asp
            20                  25

<210> SEQ ID NO 120
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 120

Glu Gly Phe Tyr Ala Ala Ile Glu Ile Val Ser Leu Pro Asn Leu Asn
1               5                   10                  15

Gln Arg Gln Arg Thr Ala Phe Ile Ser Ser Leu Ala Asp
            20                  25

<210> SEQ ID NO 121
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 121

Glu Gly Phe Tyr Ala Gly Ile Glu Ile Ile Ala Leu Pro Asn Leu Asn
1               5                   10                  15

Gln His Gln Arg Glu Ala Phe Ile Lys Ser Leu Asn Asp
            20                  25

<210> SEQ ID NO 122
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 122

Glu Gly Phe Tyr Ala Ala Ile Glu Ile Leu Ser Leu Pro Asn Leu Asn
 1               5                  10                  15

Ser Arg Gln His Arg Ala Phe Ile Thr Ser Leu Ala Asp
            20                  25

<210> SEQ ID NO 123
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 123

Glu Gly Phe Tyr Ala Ala Leu Glu Ile Val Ser Leu Pro Asn Leu Asn
 1               5                  10                  15

Ser Arg Gln Arg Thr Ala Phe Ile Thr Ser Leu Ser Asp
            20                  25

<210> SEQ ID NO 124
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 124

Glu Gly Phe Tyr Ala Leu Ile Glu Ile Val Ser Leu Pro Asn Leu Asn
 1               5                  10                  15

His Lys Gln Arg Asn Ala Phe Ile Arg Ser Leu Asn Asp
            20                  25

<210> SEQ ID NO 125
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 125

Glu Gly Phe Tyr Ala Ala Leu Glu Ile Val Ala Leu Pro Asn Leu Asn
 1               5                  10                  15

Pro Arg Gln Arg Thr Ala Phe Ile Arg Ser Leu Glu Asp
            20                  25

<210> SEQ ID NO 126
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 126

Glu Gly Phe Tyr Ala Ala Ile Glu Ile Leu Thr Leu Pro Asn Leu Asn
 1               5                  10                  15

Arg Arg Gln Arg Ser Ala Phe Ile Ala Ser Leu Gly Asp
            20                  25

<210> SEQ ID NO 127
<211> LENGTH: 29
<212> TYPE: PRT
<213> ORGANISM: Artificial Sequence
<220> FEATURE:
<223> OTHER INFORMATION: Engineered IGF-1R binding polypeptide
```

<400> SEQUENCE: 127

Glu Gly Phe Tyr Ala Ala Leu Glu Ile Val Gly Leu Pro Asn Leu Thr
1               5                   10                  15

Gly Arg Gln Arg Thr Ala Phe Ile Gln Ser Leu Gly Asp
            20                  25

<210> SEQ ID NO 128
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 128

Glu Gly Phe Tyr Ala Ala Met Glu Ile Val Ala Leu Pro Asn Leu Asn
1               5                   10                  15

Gly Arg Gln Arg Arg Ala Phe Ile Arg Ser Leu Glu Asp
            20                  25

<210> SEQ ID NO 129
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 129

Glu Gly Phe Tyr Ala Ala Ile Glu Ile Val Thr Leu Pro Asn Leu Thr
1               5                   10                  15

Gly Asn Gln Arg Thr Ala Phe Ile Arg Ser Leu Gly Asp
            20                  25

<210> SEQ ID NO 130
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 130

Glu Gly Phe Tyr Ala Ala Leu Glu Ile Leu Thr Leu Pro Asn Leu Thr
1               5                   10                  15

Arg His Gln Arg Thr Ala Phe Ile Asp Ser Leu Gly Asp
            20                  25

<210> SEQ ID NO 131
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 131

Glu Gly Phe Tyr Ala Ser Met Glu Ile Leu Ser Leu Pro Asn Leu Asn
1               5                   10                  15

Gly Lys Gln Arg Thr Ala Phe Ile Thr Ser Leu Glu Asp
            20                  25

<210> SEQ ID NO 132
<211> LENGTH: 29
<212> TYPE: PRT
<213> ORGANISM: Artificial Sequence
<220> FEATURE:
<223> OTHER INFORMATION: Engineered IGF-1R binding polypeptide

```
<400> SEQUENCE: 132

Glu Gly Phe Tyr Ala Ala Leu Glu Ile Leu Thr Leu Pro Asn Leu Asn
1               5                   10                  15

Thr Lys Gln Arg Thr Ala Phe Ile Gly Ser Leu Gly Asp
            20                  25

<210> SEQ ID NO 133
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 133

Glu Gly Phe Tyr Ala Ala Met Glu Ile Val Ala Leu Pro Asn Leu Asn
1               5                   10                  15

Arg Gln Gln Arg Thr Ala Phe Ile Asn Ser Leu Thr Asp
            20                  25

<210> SEQ ID NO 134
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 134

Glu Gly Phe Tyr Ala Ala Ile Glu Ile Ile Ile Leu Pro Asn Leu Thr
1               5                   10                  15

Pro Arg Gln Arg Ser Ala Phe Ile Asp Ser Leu Glu Asp
            20                  25

<210> SEQ ID NO 135
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 135

Glu Gly Phe Tyr Ala Ala Met Glu Ile Leu Gln Leu Pro Asn Leu Thr
1               5                   10                  15

Asn Arg Gln Arg Ala Ala Phe Ile Ser Ser Leu Pro Asp
            20                  25

<210> SEQ ID NO 136
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 136

Glu Gly Phe Tyr Ala Ala Ile Glu Ile Leu Val Leu Pro Asn Leu Asn
1               5                   10                  15

Gln Asp Gln Arg Thr Ala Phe Ile Thr Ser Leu Thr Asp
            20                  25

<210> SEQ ID NO 137
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 137

Glu Gly Phe Tyr Ala Ala Leu Glu Ile Leu Ile Leu Pro Asn Leu Asn
1               5                   10                  15

Ser Ser Gln Arg Thr Ala Phe Ile Gly Ser Leu Glu Asp
            20                  25

<210> SEQ ID NO 138
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 138

Glu Gly Phe Tyr Ala Ala Ile Glu Ile Leu Ala Leu Pro Asn Leu Asn
1               5                   10                  15

Thr Arg Gln His Arg Ala Phe Ile Arg Ser Leu Thr Asp
            20                  25

<210> SEQ ID NO 139
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 139

Glu Gly Phe Tyr Ala Ala Leu Glu Ile Leu Val Leu Pro Asn Leu Asn
1               5                   10                  15

His Lys Gln Arg Thr Ala Phe Ile Gly Ser Leu Glu Asp
            20                  25

<210> SEQ ID NO 140
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 140

Glu Gly Phe Tyr Ala Ala Ile Glu Ile Leu Ser Leu Pro Asn Leu Thr
1               5                   10                  15

Arg Arg Gln Arg Gly Ala Phe Ile Thr Ser Leu Glu Asp
            20                  25

<210> SEQ ID NO 141
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 141

Glu Gly Phe Tyr Ala Ala Ile Glu Ile Ile Ser Leu Pro Asn Leu Asn
1               5                   10                  15

Ala Arg Gln Arg Thr Ala Phe Ile Ala Ser Leu Gly Asp
            20                  25

<210> SEQ ID NO 142
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 142

Glu Gly Phe Tyr Ala Ala Ile Glu Ile Leu Ala Leu Pro Asn Leu Asn
 1               5                  10                  15

Arg Thr Gln Arg Ser Ala Phe Ile Gly Ser Leu Ala Asp
            20                  25

<210> SEQ ID NO 143
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 143

Glu Gly Phe Tyr Ala Ala Ile Glu Ile Ile Ser Leu Pro Asn Leu Asn
 1               5                  10                  15

Pro Arg Gln Arg Thr Ala Phe Ile Thr Ser Leu Thr Asp
            20                  25

<210> SEQ ID NO 144
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 144

Glu Gly Phe Tyr Ala Ala Ile Glu Ile Leu Val Leu Pro Asn Leu Asn
 1               5                  10                  15

Lys Arg Gln Arg Ala Ala Phe Ile Gly Ser Leu Glu Asp
            20                  25

<210> SEQ ID NO 145
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 145

Glu Gly Phe Tyr Ala Ala Ile Glu Ile Leu Ala Leu Pro Asn Leu Asn
 1               5                  10                  15

Arg Lys Gln Arg Thr Ala Phe Ile Gln Ser Leu Asp Asp
            20                  25

<210> SEQ ID NO 146
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 146

Glu Gly Phe Tyr Ala Ala Leu Glu Ile Ile Ser Leu Pro Asn Leu Thr
 1               5                  10                  15

Gln Arg Gln His Glu Ala Phe Ile Arg Ser Leu Gly Asp
            20                  25

<210> SEQ ID NO 147
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 147

Glu Gly Phe Tyr Ala Ala Ile Glu Ile Leu Thr Leu Pro Asn Leu Thr
1               5                   10                  15

Gln Asn Gln His Thr Ala Phe Ile Arg Ser Leu Gly Asp
            20                  25

<210> SEQ ID NO 148
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 148

Glu Gly Phe Tyr Ala Ala Ile Glu Ile Leu Thr Leu Pro Asn Leu Asn
1               5                   10                  15

Gln Lys Gln His Arg Ala Phe Ile Ala Ser Leu Gly Asp
            20                  25

<210> SEQ ID NO 149
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 149

Glu Gly Phe Tyr Ala Ala Met Glu Ile Val Ala Leu Pro Asn Leu Thr
1               5                   10                  15

Ser Lys Gln Arg Thr Ala Phe Ile Arg Ser Leu Glu Asp
            20                  25

<210> SEQ ID NO 150
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 150

Glu Gly Phe Tyr Ala Ala Ile Glu Ile Leu Ile Leu Pro Asn Leu Asn
1               5                   10                  15

Thr Arg Gln Arg Gly Ala Phe Ile Gly Ser Leu Asn Asp
            20                  25

<210> SEQ ID NO 151
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 151

Glu Gly Phe Tyr Ala Ala Ile Glu Ile Leu Ser Leu Pro Asn Leu Asn
1               5                   10                  15

Arg Arg Gln Arg Ser Ala Phe Ile Ser Ser Leu Gly Asp
            20                  25

<210> SEQ ID NO 152
<211> LENGTH: 29
<212> TYPE: PRT
<213> ORGANISM: Artificial Sequence
<220> FEATURE:
<223> OTHER INFORMATION: Engineered IGF-1R binding polypeptide
```

-continued

```
<400> SEQUENCE: 152

Glu Gly Phe Tyr Ala Ala Leu Glu Ile Leu Ser Leu Pro Asn Leu Thr
1               5                   10                  15

Lys Lys Gln Arg Thr Ala Phe Ile Arg Ser Leu Gly Asp
            20                  25

<210> SEQ ID NO 153
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 153

Glu Gly Phe Tyr Ala Ala Leu Glu Ile Leu Thr Leu Pro Asn Leu Asn
1               5                   10                  15

Gln Asn Gln Arg Ser Ala Phe Ile Arg Ser Leu Gly Asp
            20                  25

<210> SEQ ID NO 154
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 154

Glu Gly Phe Tyr Ala Ala Ile Glu Ile Leu Thr Leu Pro Asn Leu Asn
1               5                   10                  15

Ser Pro Gln Arg Asp Ala Phe Ile Ser Ser Leu Gly Asp
            20                  25

<210> SEQ ID NO 155
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 155

Glu Gly Phe Tyr Ala Ala Ile Glu Ile Ile Thr Leu Pro Asn Leu Thr
1               5                   10                  15

Gln Gly Gln Arg Thr Ala Phe Ile Arg Ser Leu Ser Asp
            20                  25

<210> SEQ ID NO 156
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 156

Glu Gly Phe Tyr Ala Ala Met Glu Ile Leu Ile Leu Pro Asn Leu Thr
1               5                   10                  15

Arg Gly Gln Arg Arg Ala Phe Ile Ala Ser Leu Gly Asp
            20                  25

<210> SEQ ID NO 157
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 157

Glu Gly Phe Tyr Ala Ala Met Glu Ile Leu Thr Leu Pro Asn Leu Asn
 1               5                  10                  15

Gln Lys Gln Arg Asp Ala Phe Ile Thr Ser Leu Gly Asp
            20                  25

<210> SEQ ID NO 158
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 158

Glu Gly Phe Tyr Ala Ala Met Glu Ile Leu Thr Leu Pro Asn Leu Asn
 1               5                  10                  15

Lys Arg Gln Arg Thr Ala Phe Ile Glu Ser Leu Thr Asp
            20                  25

<210> SEQ ID NO 159
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 159

Glu Gly Phe Tyr Ala Ala Ile Glu Ile Ile Ala Leu Pro Asn Leu Thr
 1               5                  10                  15

Arg Arg Gln Arg Thr Ala Phe Ile Thr Ser Leu Glu Asp
            20                  25

<210> SEQ ID NO 160
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 160

Glu Gly Phe Tyr Ala Ala Ile Glu Ile Val Thr Leu Pro Asn Leu Thr
 1               5                  10                  15

His Arg Gln Arg Ser Ala Phe Ile Gly Ser Leu Gly Asp
            20                  25

<210> SEQ ID NO 161
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 161

Glu Gly Phe Tyr Ala Ala Met Glu Ile Leu Thr Leu Pro Asn Leu Asn
 1               5                  10                  15

Gln Arg Gln Arg Thr Ala Phe Ile Thr Ser Leu Gly Asp
            20                  25

<210> SEQ ID NO 162
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 162

Glu Gly Phe Tyr Ala Ala Leu Glu Ile Ile Thr Leu Pro Asn Leu Thr
1               5                   10                  15

Gln Arg Gln Arg Ser Ala Phe Ile Asn Ser Leu Pro Asp
            20                  25

<210> SEQ ID NO 163
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 163

Glu Gly Phe Tyr Ala Ala Ile Glu Ile Leu Thr Leu Pro Asn Leu Thr
1               5                   10                  15

Gly Arg Gln Arg Thr Ala Phe Ile Arg Ser Leu Glu Asp
            20                  25

<210> SEQ ID NO 164
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 164

Glu Gly Phe Tyr Ala Ala Ile Glu Ile Ile Ser Leu Pro Asn Leu Thr
1               5                   10                  15

Arg Arg Gln Arg Ala Ala Phe Ile Arg Ser Leu Glu Asp
            20                  25

<210> SEQ ID NO 165
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 165

Glu Gly Phe Tyr Ala Ala Ile Glu Ile Val Ser Leu Pro Asn Leu Thr
1               5                   10                  15

Ser Lys Gln Arg Gly Ala Phe Ile Thr Ser Leu Thr Asp
            20                  25

<210> SEQ ID NO 166
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 166

Glu Gly Phe Tyr Ala Ala Ile Glu Ile Val Ser Leu Pro Asn Leu Thr
1               5                   10                  15

Gln Arg Gln Arg Thr Ala Phe Ile Thr Ser Leu Glu Asp
            20                  25

<210> SEQ ID NO 167
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 167

Glu Gly Phe Tyr Ala Ala Leu Glu Ile Leu Ile Leu Pro Asn Leu Thr
1               5                   10                  15

Gln His Gln Arg Thr Ala Phe Ile Thr Ser Leu Gly Asp
            20                  25

<210> SEQ ID NO 168
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 168

Glu Gly Phe Tyr Ala Ala Ile Glu Ile Leu Thr Leu Pro Asn Leu Thr
1               5                   10                  15

Ser Gln Gln Arg Arg Ala Phe Ile Thr Ser Leu Gly Asp
            20                  25

<210> SEQ ID NO 169
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 169

Glu Gly Phe Tyr Ala Ala Leu Glu Ile Ile Thr Leu Pro Asn Leu Asn
1               5                   10                  15

Pro Arg Gln Arg Thr Ala Phe Ile Asn Ser Leu Thr Asp
            20                  25

<210> SEQ ID NO 170
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 170

Glu Gly Phe Tyr Ala Ala Met Glu Ile Leu Thr Leu Pro Asn Leu Asn
1               5                   10                  15

Lys Arg Gln Arg Ser Ala Phe Ile Arg Ser Leu Glu Asp
            20                  25

<210> SEQ ID NO 171
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 171

Glu Gly Phe Tyr Ala Ala Ile Glu Ile Leu Val Leu Pro Asn Leu Asn
1               5                   10                  15

Thr Gln Gln Arg Arg Ala Phe Ile Lys Ser Leu Glu Asp
            20                  25

<210> SEQ ID NO 172
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 172

Glu Gly Phe Tyr Ala Ala Leu Glu Ile Val Ser Leu Pro Asn Leu Asn
 1               5                  10                  15

Thr Arg Gln Arg Ser Ala Phe Ile Thr Ser Leu Gly Asp
            20                  25

<210> SEQ ID NO 173
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 173

Glu Gly Phe Tyr Ala Ala Ile Glu Ile Leu Val Leu Pro Asn Leu Asn
 1               5                  10                  15

Lys Arg Gln Arg Glu Ala Phe Ile Gly Ser Leu Thr Asp
            20                  25

<210> SEQ ID NO 174
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 174

Glu Gly Phe Tyr Ala Ala Met Glu Ile Leu Val Leu Pro Asn Leu Asn
 1               5                  10                  15

Gln Lys Gln Arg Arg Ala Phe Ile Asn Ser Leu Gly Asp
            20                  25

<210> SEQ ID NO 175
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 175

Glu Gly Phe Tyr Ala Ala Ile Glu Ile Leu Thr Leu Pro Asn Leu Thr
 1               5                  10                  15

Arg Arg Gln Arg Ser Ala Phe Ile Thr Ser Leu Gln Asp
            20                  25

<210> SEQ ID NO 176
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 176

Glu Gly Phe Tyr Ala Ala Ile Glu Ile Leu Ser Leu Pro Asn Leu Thr
 1               5                  10                  15

Gly Arg Gln His Arg Ala Phe Ile Thr Ser Leu Glu Asp
            20                  25

<210> SEQ ID NO 177
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 177

Glu Gly Phe Tyr Ala Ala Ile Glu Ile Ile Ala Leu Pro Asn Leu Asn
 1               5                  10                  15

Arg Arg Gln Arg Ser Ala Phe Ile Arg Ser Leu Gln Asp
            20                  25

<210> SEQ ID NO 178
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 178

Glu Gly Phe Tyr Ala Ala Leu Glu Ile Leu Val Leu Pro Asn Leu Thr
 1               5                  10                  15

Gly Arg Gln Arg Lys Ala Phe Ile Glu Ser Leu Pro Asp
            20                  25

<210> SEQ ID NO 179
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 179

Glu Gly Phe Tyr Ala Ala Ile Glu Ile Leu Thr Leu Pro Asn Leu Asn
 1               5                  10                  15

Ser Arg Gln Arg Thr Ala Phe Ile Gly Ser Leu Gly Asp
            20                  25

<210> SEQ ID NO 180
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 180

Glu Gly Phe Tyr Ala Ala Leu Glu Ile Leu Val Leu Pro Asn Leu Asn
 1               5                  10                  15

Pro Lys Gln Arg Thr Ala Phe Ile Asp Ser Leu Ser Asp
            20                  25

<210> SEQ ID NO 181
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 181

Glu Gly Phe Tyr Ala Ser Ile Glu Ile Leu Val Leu Pro Asn Leu Asn
 1               5                  10                  15

Gly Arg Gln Arg Thr Ala Phe Ile Thr Ser Leu Ala Asp
            20                  25

<210> SEQ ID NO 182
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 182

Glu Gly Phe Tyr Ala Ala Ile Glu Ile Leu Thr Leu Pro Asn Leu Asn
1               5                   10                  15

Ser Arg Gln Arg Arg Ala Phe Ile Gly Ser Leu Gln Asp
            20                  25

<210> SEQ ID NO 183
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 183

Glu Gly Phe Tyr Ala Ala Met Glu Ile Leu Thr Leu Pro Asn Leu Asn
1               5                   10                  15

Arg Lys Gln Arg Ser Ala Phe Ile Gly Ser Leu Thr Asp
            20                  25

<210> SEQ ID NO 184
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 184

Glu Gly Phe Tyr Ala Ala Ile Glu Ile Leu Ile Leu Pro Asn Leu Asn
1               5                   10                  15

Gln Arg Gln Arg Ser Ala Phe Ile Gly Ser Leu Glu Asp
            20                  25

<210> SEQ ID NO 185
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 185

Glu Gly Phe Tyr Ala Ala Ile Glu Ile Leu Ala Leu Pro Asn Leu Asn
1               5                   10                  15

Arg Arg Gln Arg Ser Ala Phe Ile Asn Ser Leu Gly Asp
            20                  25

<210> SEQ ID NO 186
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 186

Glu Gly Phe Tyr Ala Ala Leu Glu Ile Val Ala Leu Pro Asn Leu Asn
1               5                   10                  15

Arg Lys Gln Arg Thr Ala Phe Ile Ser Ser Leu Thr Asp
            20                  25

<210> SEQ ID NO 187
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 187

Glu Gly Phe Tyr Ala Ala Met Glu Ile Leu Gly Leu Pro Asn Leu Asn
1               5                   10                  15

Asn Arg Gln Arg Arg Ala Phe Ile Thr Ser Leu Thr Asp
            20                  25

<210> SEQ ID NO 188
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 188

Glu Gly Phe Tyr Ala Ala Val Glu Ile Leu Thr Leu Pro Asn Leu Thr
1               5                   10                  15

Arg Arg Gln His Arg Ala Phe Ile Thr Ser Leu Gly Asp
            20                  25

<210> SEQ ID NO 189
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 189

Glu Gly Phe Tyr Ala Ala Ile Glu Ile Val Ala Leu Pro Asn Leu Thr
1               5                   10                  15

Thr Lys Gln Arg Ser Ala Phe Ile Arg Ser Leu Gly Asp
            20                  25

<210> SEQ ID NO 190
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 190

Glu Gly Phe Tyr Ala Ala Leu Glu Ile Leu Val Leu Pro Asn Leu Thr
1               5                   10                  15

Gly Asn Gln Arg Thr Ala Phe Ile Thr Ser Leu Thr Asp
            20                  25

<210> SEQ ID NO 191
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 191

Glu Gly Phe Tyr Ala Ala Leu Glu Ile Ile Ala Leu Pro Asn Leu Asn
1               5                   10                  15

Gln Lys Gln Arg Ser Ala Phe Ile Gln Ser Leu Gly Asp
            20                  25

<210> SEQ ID NO 192
<211> LENGTH: 29
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 192

Glu Gly Phe Tyr Ala Ala Ile Glu Ile Leu Val Leu Pro Asn Leu Asn
1               5                   10                  15

Ser Arg Gln Arg Asp Ala Phe Ile Arg Ser Leu Ser Asp
            20                  25

<210> SEQ ID NO 193
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 193

Glu Gly Phe Tyr Ala Ala Leu Glu Ile Leu Ile Leu Pro Asn Leu Asn
1               5                   10                  15

Gln Gly Gln Arg Asp Ala Phe Ile Thr Ser Leu Gly Asp
            20                  25

<210> SEQ ID NO 194
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 194

Glu Gly Phe Tyr Ala Ala Met Glu Ile Leu Ile Leu Pro Asn Leu Thr
1               5                   10                  15

Arg Arg Gln His Arg Ala Phe Ile Thr Ser Leu Glu Asp
            20                  25

<210> SEQ ID NO 195
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 195

Glu Gly Phe Tyr Ala Ala Leu Glu Ile Leu Ser Leu Pro Asn Leu Thr
1               5                   10                  15

Pro Lys Gln Arg Ser Ala Phe Ile Thr Ser Leu Thr Asp
            20                  25

<210> SEQ ID NO 196
<211> LENGTH: 29
<212> TYPE: PRT
<213> ORGANISM: Artificial Sequence
<220> FEATURE:
<223> OTHER INFORMATION: Engineered IGF-1R binding polypeptide

<400> SEQUENCE: 196

Glu Gly Phe Tyr Ala Ala Ile Glu Ile Val Val Leu Pro Asn Leu Thr
1               5                   10                  15

Pro Arg Gln Arg Ser Ala Phe Ile Lys Ser Leu Asp Asp
            20                  25

<210> SEQ ID NO 197
<211> LENGTH: 29
<212> TYPE: PRT
<213> ORGANISM: Artificial Sequence
<220> FEATURE:
<223> OTHER INFORMATION: Engineered IGF-1R binding polypeptide
```

-continued

```
<400> SEQUENCE: 197

Glu Gly Phe Tyr Ala Ala Ile Glu Ile Leu Thr Leu Pro Asn Leu Asn
1               5                   10                  15

Pro Gln Gln Arg Thr Ala Phe Ile Lys Ser Leu Glu Asp
            20                  25

<210> SEQ ID NO 198
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 198

Val Asp Asn Lys Phe Asn Lys Glu Gly Phe Tyr Ala Ala Ile Glu Ile
1               5                   10                  15

Leu Ala Leu Pro Asn Leu Asn Arg Lys Gln Ser Thr Ala Phe Ile Ser
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 199
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 199

Val Asp Asn Lys Phe Asn Lys Glu Gly Phe Tyr Ala Ala Ile Glu Ile
1               5                   10                  15

Leu Ser Leu Pro Asn Leu Asn His Ser Gln Arg Gly Ala Phe Ile Thr
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 200
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 200

Val Asp Asn Lys Phe Asn Lys Glu Lys Phe Tyr Ala Ala Ile Glu Ile
1               5                   10                  15

Leu Ala Leu Pro Asn Leu Asn Arg Lys Gln Ser Thr Ala Phe Ile Arg
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 201
<211> LENGTH: 58
<212> TYPE: PRT
<213> ORGANISM: Artificial Sequence
<220> FEATURE:
```

-continued

<223> OTHER INFORMATION: Engineered IGF-1R binding polypeptide

<400> SEQUENCE: 201

Val Asp Asn Lys Phe Asn Lys Glu Pro Phe Tyr Ala Ala Met Glu Ile
1               5                   10                  15

Leu Thr Leu Pro Asn Leu Asn Asn Gly Gln Arg Arg Ala Phe Ile Thr
            20                  25                  30

Ser Leu Asn Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 202
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 202

Val Asp Asn Lys Phe Asn Lys Glu Gly Phe Tyr Ala Ala Leu Glu Ile
1               5                   10                  15

Ile Leu Leu Pro Asn Leu Asn Pro Ser Gln Trp Thr Ala Phe Ile Thr
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 203
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 203

Val Asp Asn Lys Phe Asn Lys Glu Gly Phe Tyr Ala Ala Leu Glu Ile
1               5                   10                  15

Leu Val Leu Pro Asn Leu Asn Thr Gln Gln Arg Gly Ala Phe Ile Thr
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 204
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 204

Val Asp Asn Lys Phe Asn Lys Glu Gly Phe Tyr Ala Ala Ile Glu Ile
1               5                   10                  15

Leu Ser Leu Pro Asn Leu Asn His Ser Gln Arg Gly Ala Phe Ile Thr
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys

-continued

```
<210> SEQ ID NO 205
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 205

Val Asp Asn Lys Phe Asn Lys Glu Gly Phe Tyr Ala Ala Met Glu Ile
1               5                   10                  15

Leu Ala Leu Pro Asn Leu Asn Ser Arg Gln Ser Lys Ala Phe Ile Asn
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 206
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 206

Val Asp Asn Lys Phe Asn Lys Glu Gly Phe Tyr Ala Ala Val Glu Ile
1               5                   10                  15

Leu Gly Leu Pro Asn Leu Asn Ala Arg Gln Arg Thr Ala Phe Ile Asn
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 207
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 207

Val Asp Asn Lys Phe Asn Lys Glu Gly Phe Tyr Ala Ala Met Glu Ile
1               5                   10                  15

Val Ile Leu Pro Asn Leu Thr His Arg Gln Arg Ala Ala Phe Ile Gly
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 208
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 208

Val Asp Asn Lys Phe Asn Lys Glu Gly Phe Tyr Ala Ala Ile Glu Ile
1               5                   10                  15
```

```
Leu Ser Leu Pro Asn Leu Thr Gln Lys Gln His Thr Ala Phe Ile Gly
        20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 209
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 209

Val Asp Asn Lys Phe Asn Lys Glu Gly Phe Tyr Ala Ala Met Glu Ile
1               5                   10                  15

Leu Ala Leu Pro Asn Leu Asn Gly Arg Gln Arg Ser Ala Phe Ile Thr
        20                  25                  30

Ser Leu Asn Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 210
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 210

Val Asp Asn Lys Phe Asn Lys Glu Gly Phe Tyr Ala Ala Ile Glu Ile
1               5                   10                  15

Leu Thr Leu Pro Asn Leu Asn Arg Arg Gln Arg Ser Ala Phe Ile Thr
        20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 211
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 211

Val Asp Asn Lys Phe Asn Lys Glu Gly Phe Tyr Ala Ala Leu Glu Ile
1               5                   10                  15

Leu Ala Leu Pro Asn Leu Asn Arg Lys Gln Arg Thr Ala Phe Ile Ser
        20                  25                  30

Ser Leu Asp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 212
<211> LENGTH: 58
<212> TYPE: PRT
```

<213> ORGANISM: Artificial Sequence
<220> FEATURE:
<223> OTHER INFORMATION: Engineered IGF-1R binding polypeptide

<400> SEQUENCE: 212

Val Asp Asn Lys Phe Asn Lys Glu Gly Phe Tyr Ala Ala Leu Glu Ile
1               5                   10                  15

Val Ser Leu Pro Asn Leu Thr Glu Arg Gln Arg Ala Ala Phe Ile Gly
            20                  25                  30

Ser Leu Asp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 213
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 213

Val Asp Asn Lys Phe Asn Lys Glu Gly Phe Tyr Ala Ala Val Glu Ile
1               5                   10                  15

Val Thr Leu Pro Asn Leu Thr Lys Gly Gln Arg Glu Ala Phe Ile Gly
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 214
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 214

Val Asp Asn Lys Phe Asn Lys Glu Gly Phe Tyr Ala Ala Leu Glu Ile
1               5                   10                  15

Leu Thr Leu Pro Asn Leu Asn Thr Lys Gln His Arg Ala Phe Ile Thr
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 215
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 215

Val Asp Asn Lys Phe Asn Lys Glu Gly Phe Tyr Ala Ala Ile Glu Ile
1               5                   10                  15

Val Ala Leu Pro Asn Leu Asn Arg Arg Gln Arg Ser Ala Phe Ile Arg
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 216
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 216

Val Asp Asn Lys Phe Asn Lys Glu Gly Phe Tyr Ala Ala Leu Glu Ile
1               5                   10                  15

Val Ala Leu Pro Asn Leu Thr Pro Arg Gln Arg Thr Ala Phe Ile Gly
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 217
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 217

Val Asp Asn Lys Phe Asn Lys Glu Gly Phe Tyr Ala Gly Ile Glu Ile
1               5                   10                  15

Leu Ile Leu Pro Asn Leu Asn Glu Arg Gln Arg Ala Ala Phe Ile Arg
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 218
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 218

Val Asp Asn Lys Phe Asn Lys Glu Gly Phe Tyr Ala Ala Leu Glu Ile
1               5                   10                  15

Val Ala Leu Pro Asn Leu Thr Ser Lys Gln Arg Glu Ala Phe Ile Gly
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 219
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 219

Val Asp Asn Lys Phe Asn Lys Glu Gly Phe Tyr Ala Ala Ile Glu Ile
1               5                   10                  15

Leu Ile Leu Pro Asn Leu Asn Gly Ser Gln Arg Arg Ala Phe Ile Ser
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 220
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 220

Val Asp Asn Lys Phe Asn Lys Glu Gly Phe Tyr Ala Ala Leu Glu Ile
1               5                   10                  15

Leu Ala Leu Pro Asn Leu Asn Thr Arg Gln Arg Ser Ala Phe Ile Ser
            20                  25                  30

Ser Leu Pro Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 221
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 221

Val Asp Asn Lys Phe Asn Lys Glu Gly Phe Tyr Ala Ala Leu Glu Ile
1               5                   10                  15

Leu Val Leu Pro Asn Leu Thr Gln Arg Gln Arg Thr Ala Phe Ile Thr
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 222
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 222

Val Asp Asn Lys Phe Asn Lys Glu Gly Phe Tyr Ala Ala Ile Glu Ile
1               5                   10                  15

Leu Thr Leu Pro Asn Leu Asn Asn Arg Gln Arg Thr Ala Phe Ile Thr
            20                  25                  30

Ser Leu Pro Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 223

-continued

```
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 223

Val Asp Asn Lys Phe Asn Lys Glu Gly Phe Tyr Ala Ala Val Glu Ile
 1               5                   10                  15

Leu Val Leu Pro Asn Leu Thr Ser Arg Gln Arg Thr Ala Phe Ile Gly
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 224
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 224

Val Asp Asn Lys Phe Asn Lys Glu Gly Phe Tyr Ala Ala Ile Glu Ile
 1               5                   10                  15

Leu Ala Leu Pro Asn Leu Asn His Arg Gln Arg Gly Ala Phe Ile Ser
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 225
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 225

Val Asp Asn Lys Phe Asn Lys Glu Gly Phe Tyr Ala Ala Leu Glu Ile
 1               5                   10                  15

Val Ser Leu Pro Asn Leu Asn Gln Arg Gln Arg Thr Ala Phe Ile Thr
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 226
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 226

Val Asp Asn Lys Phe Asn Lys Glu Gly Phe Tyr Ala Ala Ile Glu Ile
 1               5                   10                  15

Leu Thr Leu Pro Asn Leu Asn Glu Arg Gln Arg Gly Ala Phe Ile Gly
            20                  25                  30
```

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 227
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 227

Val Asp Asn Lys Phe Asn Lys Glu Gly Phe Tyr Ala Ala Leu Glu Ile
1               5                   10                  15

Leu Ile Leu Pro Asn Leu Asn Arg Asn Gln Arg Thr Ala Phe Ile Ser
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 228
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 228

Val Asp Asn Lys Phe Asn Lys Glu Gly Phe Tyr Ala Ala Ile Glu Ile
1               5                   10                  15

Leu Thr Leu Pro Asn Leu Asn Arg Arg Gln Arg Asp Ala Phe Ile Thr
            20                  25                  30

Ser Leu Asn Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 229
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 229

Val Asp Asn Lys Phe Asn Lys Glu Gly Phe Tyr Ala Ala Ile Glu Ile
1               5                   10                  15

Met Ser Leu Pro Asn Leu Thr Arg Arg Gln Arg Ser Ala Phe Ile Gly
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 230
<211> LENGTH: 58
<212> TYPE: PRT
<213> ORGANISM: Artificial Sequence
<220> FEATURE:
<223> OTHER INFORMATION: Engineered IGF-1R binding polypeptide -continued

```
<400> SEQUENCE: 230

Val Asp Asn Lys Phe Asn Lys Glu Gly Phe Tyr Ala Ala Leu Glu Ile
1               5                   10                  15

Leu Val Leu Pro Asn Leu Asn Ser His Gln Arg Ala Ala Phe Ile Ala
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 231
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 231

Val Asp Asn Lys Phe Asn Lys Glu Gly Phe Tyr Ala Gly Ile Glu Ile
1               5                   10                  15

Leu Thr Leu Pro Asn Leu Asn Arg Arg Gln Arg Glu Ala Phe Ile Gly
            20                  25                  30

Ser Leu Asn Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 232
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 232

Val Asp Asn Lys Phe Asn Lys Glu Gly Phe Tyr Ala Ala Val Glu Ile
1               5                   10                  15

Leu Thr Leu Pro Asn Leu Thr Arg Arg Gln Arg Ser Ala Phe Ile Gly
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 233
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 233

Val Asp Asn Lys Phe Asn Lys Glu Gly Phe Tyr Ala Ala Ile Glu Ile
1               5                   10                  15

Val Ala Leu Pro Asn Leu Thr Gly Lys Gln Arg Ser Ala Phe Ile Lys
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 234
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 234

Val Asp Asn Lys Phe Asn Lys Glu Gly Phe Tyr Ala Ala Leu Glu Ile
1               5                   10                  15

Val Thr Leu Pro Asn Leu Asn Glu Arg Gln Arg Arg Ala Phe Ile Ala
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 235
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 235

Val Asp Asn Lys Phe Asn Lys Glu Gly Phe Tyr Ala Ala Met Glu Ile
1               5                   10                  15

Val Ala Leu Pro Asn Leu Asn Ala Arg Gln Arg Thr Ala Phe Ile Gly
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 236
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 236

Val Asp Asn Lys Phe Asn Lys Glu Gly Phe Tyr Ala Ala Leu Glu Ile
1               5                   10                  15

Ile Thr Leu Pro Asn Leu Thr His Arg Gln Gln Arg Ala Phe Ile Thr
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 237
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 237

Val Asp Asn Lys Phe Asn Lys Glu Gly Phe Tyr Ala Ala Ile Glu Ile
1               5                   10                  15

Val Ala Leu Pro Asn Leu Thr Arg His Gln Gln Arg Ala Phe Ile Asn

```
                    20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 238
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 238

Val Asp Asn Lys Phe Asn Lys Glu Gly Phe Tyr Ala Ala Val Glu Ile
1               5                  10                  15

Ile Ile Leu Pro Asn Leu Thr Glu Lys Gln Arg Ser Ala Phe Ile Gly
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 239
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 239

Val Asp Asn Lys Phe Asn Lys Glu Gly Phe Tyr Ala Ala Leu Glu Ile
1               5                  10                  15

Leu Thr Leu Pro Asn Leu Asn Gln Arg Gln His Arg Ala Phe Ile Ser
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 240
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 240

Val Asp Asn Lys Phe Asn Lys Glu Gly Phe Tyr Ala Ala Leu Glu Ile
1               5                  10                  15

Val Thr Leu Pro Asn Leu Asn Arg Gln Gln Arg Asp Ala Phe Ile Ser
            20                  25                  30

Ser Leu Asn Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 241
<211> LENGTH: 58
<212> TYPE: PRT
<213> ORGANISM: Artificial Sequence
<220> FEATURE:
```

<223> OTHER INFORMATION: Engineered IGF-1R binding polypeptide

<400> SEQUENCE: 241

Val Asp Asn Lys Phe Asn Lys Glu

<210> SEQ ID NO 245
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 245

Val Asp Asn Lys Phe Asn Lys Glu Gly Phe Tyr Ala Ala Leu Glu Ile
1               5                   10                  15

Leu Gly Leu Pro Asn Leu Asn Arg Arg Gln Arg Ser Ala Phe Ile Ser
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 246
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 246

Val Asp Asn Lys Phe Asn Lys Glu Gly Phe Tyr Ala Ala Ile Glu Ile
1               5                   10                  15

Leu Ser Leu Pro Asn Leu Asn Pro Gly Gln Arg Thr Ala Phe Ile Asn
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 247
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 247

Val Asp Asn Lys Phe Asn Lys Glu Gly Phe Tyr Ala Ala Met Glu Ile
1               5                   10                  15

Leu Thr Leu Pro Asn Leu Asn Ser Gly Gln Arg Ser Ala Phe Ile Arg
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 248
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 248

Val Asp Asn Lys Phe Asn Lys Glu Gly Phe Tyr Ala Ala Ile Glu Ile
1               5                   10                  15

```
Leu Thr Leu Pro Asn Leu Thr Arg Asn Gln Arg Ser Ala Phe Ile Gly
        20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 249
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 249

Val Asp Asn Lys Phe Asn Lys Glu Gly Phe Tyr Ala Ala Leu Glu Ile
1               5                   10                  15

Val Ala Leu Pro Asn Leu Asn Arg Arg Gln Arg Thr Ala Phe Ile Thr
        20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 250
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 250

Val Asp Asn Lys Phe Asn Lys Glu Gly Phe Tyr Ala Ala Ile Glu Ile
1               5                   10                  15

Val Ala Leu Pro Asn Leu Asn Arg Lys Gln Arg Ser Ala Phe Ile Arg
        20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 251
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 251

Val Asp Asn Lys Phe Asn Lys Glu Gly Phe Tyr Ala Ala Ile Glu Ile
1               5                   10                  15

Val Ser Leu Pro Asn Leu Asn Gly Arg Gln Arg Arg Ala Phe Ile Ser
        20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 252
<211> LENGTH: 58
<212> TYPE: PRT
```

<213> ORGANISM: Artificial Sequence
<220> FEATURE:
<223> OTHER INFORMATION: Engineered IGF-1R binding polypeptide

<400> SEQUENCE: 252

Val Asp Asn Lys Phe Asn Lys Glu Gly Phe Tyr Ala Ala Ile Glu Ile
1               5                   10                  15

Leu Thr Leu Pro Asn Leu Asn Asn Thr Gln Arg Lys Ala Phe Ile Thr
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 253
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 253

Val Asp Asn Lys Phe Asn Lys Glu Gly Phe Tyr Ala Ala Leu Glu Ile
1               5                   10                  15

Val Ala Leu Pro Asn Leu Asn Arg Lys Gln Arg Gly Ala Phe Ile Asp
            20                  25                  30

Ser Leu Asn Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 254
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 254

Val Asp Asn Lys Phe Asn Lys Glu Gly Phe Tyr Ala Ala Ile Glu Ile
1               5                   10                  15

Leu Ser Leu Pro Asn Leu Asn Ser Lys Gln His Arg Ala Phe Ile Asn
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 255
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 255

Val Asp Asn Lys Phe Asn Lys Glu Gly Phe Tyr Ala Ala Ile Glu Ile
1               5                   10                  15

Leu Thr Leu Pro Asn Leu Asn Ala Asn Gln Arg Thr Ala Phe Ile Gly
            20                  25                  30

Ser Leu Gly Asp Asp Pro Ser Gln Ser Ala Asn Leu Leu Ala Glu Ala
        35                  40                  45

```
Lys Lys Leu Asn Asp Ala Gln Ala Pro Lys
    50                  55
```

<210> SEQ ID NO 256
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 256

```
Val Asp Asn Lys Phe Asn Lys Glu Gly Phe Tyr Ala Ala Leu Glu Ile
1               5                   10                  15

Val Ala Leu Pro Asn Leu Thr Asn Arg Gln Arg Ser Ala Phe Ile Thr
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 257
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 257

```
Val Asp Asn Lys Phe Asn Lys Glu Gly Phe Tyr Ala Ala Ile Glu Ile
1               5                   10                  15

Leu Thr Leu Pro Asn Leu Asn Arg Arg Gln His Glu Ala Phe Ile Ala
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 258
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 258

```
Val Asp Asn Lys Phe Asn Lys Glu Gly Phe Tyr Ala Ala Met Glu Ile
1               5                   10                  15

Leu Val Leu Pro Asn Leu Thr Gln Arg Gln Arg Glu Ala Phe Ile Thr
            20                  25                  30

Ser Leu Asn Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 259
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 259

```
Val Asp Asn Lys Phe Asn Lys Glu Gly Phe Tyr Ala Ala Ile Glu Ile
  1               5                  10                  15

Val Ala Leu Pro Asn Leu Asn Ser Gln Arg Thr Ala Phe Ile Arg
             20                  25                  30

Ser Leu Thr Asp Asp Pro Ser Gln Ser Ala Asn Leu Leu Ala Glu Ala
             35                  40                  45

Lys Lys Leu Asn Asp Ala Gln Ala Pro Lys
     50                  55

<210> SEQ ID NO 260
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 260

Val Asp Asn Lys Phe Asn Lys Glu Gly Phe Tyr Ala Ala Ile Glu Ile
  1               5                  10                  15

Val Ala Leu Pro Asn Leu Thr Pro Arg Gln Arg Ala Ala Phe Ile Arg
             20                  25                  30

Ser Leu Ala Asp Asp Pro Ser Gln Ser Ala Asn Leu Leu Ala Glu Ala
             35                  40                  45

Lys Lys Leu Asn Asp Ala Gln Ala Pro Lys
     50                  55

<210> SEQ ID NO 261
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 261

Val Asp Asn Lys Phe Asn Lys Glu Gly Phe Tyr Ala Ala Leu Glu Ile
  1               5                  10                  15

Leu Ser Leu Pro Asn Leu Asn Lys His Gln Arg Lys Ala Phe Ile Ser
             20                  25                  30

Ser Leu Glu Asp Asp Pro Ser Gln Ser Ala Asn Leu Leu Ala Glu Ala
             35                  40                  45

Lys Lys Leu Asn Asp Ala Gln Ala Pro Lys
     50                  55

<210> SEQ ID NO 262
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 262

Val Asp Asn Lys Phe Asn Lys Glu Gly Phe Tyr Ala Ala Leu Glu Ile
  1               5                  10                  15

Val Ala Leu Pro Asn Leu Asn Gln Gln Gln Arg Arg Ala Phe Ile Gln
             20                  25                  30

Ser Leu Gly Asp Asp Pro Ser Gln Ser Ala Asn Leu Leu Ala Glu Ala
             35                  40                  45

Lys Lys Leu Asn Asp Ala Gln Ala Pro Lys
     50                  55

<210> SEQ ID NO 263
```

```
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 263

Val Asp Asn Lys Phe Asn Lys Glu Gly Phe Tyr Ala Ala Val Glu Ile
1               5                   10                  15

Leu Ala Leu Pro Asn Leu Asn Gln Arg Gln Arg Thr Ala Phe Ile Thr
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 264
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 264

Val Asp Asn Lys Phe Asn Lys Glu Gly Phe Tyr Ala Ala Ile Glu Ile
1               5                   10                  15

Ile Ser Leu Pro Asn Leu Asn Arg Arg Gln Arg Gly Ala Phe Ile Ala
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 265
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 265

Val Asp Asn Lys Phe Asn Lys Glu Gly Phe Tyr Ala Ala Leu Glu Ile
1               5                   10                  15

Val Ala Leu Pro Asn Leu Asn Ser Lys Gln Arg Arg Ala Phe Ile Thr
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 266
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 266

Val Asp Asn Lys Phe Asn Lys Glu Gly Phe Tyr Ala Ala Met Glu Ile
1               5                   10                  15

Ile Ala Leu Pro Asn Leu Thr Gln Arg Gln Arg Thr Ala Phe Ile Arg
            20                  25                  30
```

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 267
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 267

Val Asp Asn Lys Phe Asn Lys Glu Gly Phe Tyr Ala Ala Ile Glu Ile
1               5                   10                  15

Leu Val Leu Pro Asn Leu Asn Glu Ser Gln Arg Ser Ala Phe Ile Lys
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 268
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 268

Val Asp Asn Lys Phe Asn Lys Glu Gly Phe Tyr Ala Ala Ile Glu Ile
1               5                   10                  15

Leu Val Leu Pro Asn Leu Thr Gln Ser Gln Arg Arg Ala Phe Ile Thr
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 269
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 269

Val Asp Asn Lys Phe Asn Lys Glu Gly Phe Tyr Ala Ala Leu Glu Ile
1               5                   10                  15

Leu Thr Leu Pro Asn Leu Asn Lys Gln His Arg Ala Phe Ile Asn
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 270
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 270

Val Asp Asn Lys Phe Asn Lys Glu Gly Phe Tyr Ala Ala Ile Glu Ile
1               5                   10                  15

Leu Thr Leu Pro Asn Leu Asn Gln Arg Gln Arg Thr Ala Phe Ile Thr
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 271
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 271

Val Asp Asn Lys Phe Asn Lys Glu Gly Phe Tyr Ala Ala Met Glu Ile
1               5                   10                  15

Leu Val Leu Pro Asn Leu Asn Ser Arg Gln Arg Asn Ala Phe Ile His
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 272
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 272

Val Asp Asn Lys Phe Asn Lys Glu Gly Phe Tyr Ala Ala Ile Glu Ile
1               5                   10                  15

Leu Ala Leu Pro Asn Leu Asn Thr Lys Gln Arg Thr Ala Phe Ile Asn
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 273
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 273

Val Asp Asn Lys Phe Asn Lys Glu Gly Phe Tyr Ala Ala Met Glu Ile
1               5                   10                  15

Leu Thr Leu Pro Asn Leu Asn Pro Arg Gln Arg Thr Ala Phe Ile Glu
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 274
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 274

Val Asp Asn Lys Phe Asn Lys Glu Gly Phe Tyr Ala Ala Leu Glu Ile
1               5                   10                  15

Leu Thr Leu Pro Asn Leu Asn Pro Arg Gln Arg Arg Ala Phe Ile Thr
            20                  25                  30

Ser Leu Asp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 275
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 275

Val Asp Asn Lys Phe Asn Lys Glu Gly Phe Tyr Ala Ala Ile Glu Ile
1               5                   10                  15

Ile Thr Leu Pro Asn Leu Asn Thr Arg Gln Arg Thr Ala Phe Ile Arg
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 276
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 276

Val Asp Asn Lys Phe Asn Lys Glu Gly Phe Tyr Ala Ala Ile Glu Ile
1               5                   10                  15

Leu Ser Leu Pro Asn Leu Asn Gln Arg Gln Arg Gly Ala Phe Ile Ala
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 277
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 277

Val Asp Asn Lys Phe Asn Lys Glu Gly Phe Tyr Ala Ala Ile Glu Ile
1               5                   10                  15

Val Thr Leu Pro Asn Leu Asn Arg Arg Gln Arg Asp Ala Phe Ile Ala

-continued

```
                20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 278
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 278

Val Asp Asn Lys Phe Asn Lys Glu Gly Phe Tyr Ala Ala Met Glu Ile
 1               5                  10                  15

Leu Ile Leu Pro Asn Leu Asn Gly His Gln Arg Ser Ala Phe Ile Gly
                20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 279
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 279

Val Asp Asn Lys Phe Asn Lys Glu Gly Phe Tyr Ala Ala Leu Glu Ile
 1               5                  10                  15

Ile Thr Leu Pro Asn Leu Thr His Arg Gln His Ala Ala Phe Ile Asn
                20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 280
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 280

Val Asp Asn Lys Phe Asn Lys Glu Gly Phe Tyr Ala Ala Leu Glu Ile
 1               5                  10                  15

Leu Ile Leu Pro Asn Leu Asn Arg Gly Gln His Ala Ala Phe Ile Arg
                20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 281
<211> LENGTH: 58
<212> TYPE: PRT
<213> ORGANISM: Artificial Sequence
<220> FEATURE:
```

-continued

<223> OTHER INFORMATION: Engineered IGF-1R binding polypeptide

<400> SEQUENCE: 281

Val Asp Asn Lys Phe Asn Lys Glu Gly Phe Tyr Ala Ala Met Glu Ile
1               5                   10                  15

Ile Ala Leu Pro Asn Leu Thr Lys Arg Gln Arg Thr Ala Phe Ile Ser
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 282
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 282

Val Asp Asn Lys Phe Asn Lys Glu Gly Phe Tyr Ala Ala Leu Glu Ile
1               5                   10                  15

Leu Ala Leu Pro Asn Leu Thr Ser Lys Gln Arg Glu Ala Phe Ile Gly
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 283
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 283

Val Asp Asn Lys Phe Asn Lys Glu Gly Phe Tyr Ala Ser Ile Glu Ile
1               5                   10                  15

Leu Val Leu Pro Asn Leu Asn Ser Arg Gln Arg Ser Ala Phe Ile Ser
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 284
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 284

Val Asp Asn Lys Phe Asn Lys Glu Gly Phe Tyr Ala Ala Ile Glu Ile
1               5                   10                  15

Val Ala Leu Pro Asn Leu Thr Arg Arg Gln Arg Ala Ala Phe Ile Ala
            20                  25                  30

Ser Leu Asp Asp Asp Pro Ser Gln Ser Ala Asn Leu Leu Ala Glu Ala
        35                  40                  45

Lys Lys Leu Asn Asp Ala Gln Ala Pro Lys

<210> SEQ ID NO 285
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 285

Val Asp Asn Lys Phe Asn Lys Glu Gly Phe Tyr Ala Ala Ile Glu Ile
1               5                   10                  15

Leu Thr Leu Pro Asn Leu Asn Gln Arg Gln Arg Gly Ala Phe Ile Asn
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 286
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 286

Val Asp Asn Lys Phe Asn Lys Glu Gly Phe Tyr Ala Ala Ile Glu Ile
1               5                   10                  15

Ile Ala Leu Pro Asn Leu Thr Gln Arg Gln His Arg Ala Phe Ile Thr
            20                  25                  30

Ser Leu Asn Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 287
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 287

Val Asp Asn Lys Phe Asn Lys Glu Gly Phe Tyr Ala Ala Ile Glu Ile
1               5                   10                  15

Ile Thr Leu Pro Asn Leu Thr Lys Arg Gln Arg Ala Ala Phe Ile Gly
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 288
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 288

Val Asp Asn Lys Phe Asn Lys Glu Gly Phe Tyr Ala Ala Ile Glu Ile
1               5                   10                  15

```
Leu Val Leu Pro Asn Leu Thr Thr Arg Gln His Lys Ala Phe Ile Asn
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 289
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 289

```
Val Asp Asn Lys Phe Asn Lys Glu Gly Phe Tyr Ala Ala Ile Glu Ile
1               5                   10                  15

Val Ser Leu Pro Asn Leu Thr Ser Arg Gln Arg Thr Ala Phe Ile His
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 290
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 290

```
Val Asp Asn Lys Phe Asn Lys Glu Gly Phe Tyr Ala Ala Ile Glu Ile
1               5                   10                  15

Val Ala Leu Pro Asn Leu Asn Arg Asn Gln Arg Thr Ala Phe Ile Arg
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 291
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 291

```
Val Asp Asn Lys Phe Asn Lys Glu Gly Phe Tyr Ala Ala Ile Glu Ile
1               5                   10                  15

Ile Ser Leu Pro Asn Leu Asn Arg Lys Gln Arg Gly Ala Phe Ile Ala
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 292
<211> LENGTH: 58
<212> TYPE: PRT

```
<213> ORGANISM: Artificial Sequence
<220> FEATURE:
<223> OTHER INFORMATION: Engineered IGF-1R binding polypeptide

<400> SEQUENCE: 292

Val Asp Asn Lys Phe Asn Lys Glu Gly Phe Tyr Ala Ala Ile Glu Ile
 1               5                  10                  15

Leu Ile Leu Pro Asn Leu Asn Arg Lys Gln Ser Arg Ala Phe Ile Ala
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 293
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 293

Val Asp Asn Lys Phe Asn Lys Glu Gly Phe Tyr Ala Ala Met Glu Ile
 1               5                  10                  15

Leu Ser Leu Pro Asn Leu Asn Lys Arg Gln Arg Thr Ala Phe Ile Thr
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 294
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 294

Val Asp Asn Lys Phe Asn Lys Glu Gly Phe Tyr Ala Ala Ile Glu Ile
 1               5                  10                  15

Leu Val Leu Pro Asn Leu Asn Gln His Gln Arg Gly Ala Phe Ile Ser
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 295
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 295

Val Asp Asn Lys Phe Asn Lys Glu Gly Phe Tyr Ala Ala Leu Glu Ile
 1               5                  10                  15

Val Ser Leu Pro Asn Leu Asn Arg Asn Gln Arg Gly Ala Phe Ile Gln
            20                  25                  30

Ser Leu Thr Asp Asp Pro Ser Gln Ser Ala Asn Leu Leu Ala Glu Ala
        35                  40                  45
```

-continued

Lys Lys Leu Asn Asp Ala Gln Ala Pro Lys
    50                  55

<210> SEQ ID NO 296
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 296

Val Asp Asn Lys Phe Asn Lys Glu Gly Phe Tyr Ala Ala Met Glu Ile
1               5                   10                  15

Ile Ser Leu Pro Asn Leu Thr Lys Arg Gln Arg Arg Ala Phe Ile Thr
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 297
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 297

Val Asp Asn Lys Phe Asn Lys Glu Gly Phe Tyr Ala Ala Ile Glu Ile
1               5                   10                  15

Val Ala Leu Pro Asn Leu Thr His Lys Gln Arg Arg Ala Phe Ile Glu
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 298
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 298

Val Asp Asn Lys Phe Asn Lys Glu Gly Phe Tyr Ala Ala Leu Glu Ile
1               5                   10                  15

Leu Ala Leu Pro Asn Leu Asn His Arg Gln Arg Thr Ala Phe Ile Gly
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 299
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 299

Val Asp Asn Lys Phe Asn Lys Glu Gly Phe Tyr Ala Ala Ile Glu Ile
1               5                   10                  15

Leu Ser Leu Pro Asn Leu Asn Arg Arg Gln Arg Thr Ala Phe Ile Gly
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 300
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 300

Val Asp Asn Lys Phe Asn Lys Glu Gly Phe Tyr Ala Ala Ile Glu Ile
1               5                   10                  15

Leu Thr Leu Pro Asn Leu Asn Ser Arg Gln Arg Asp Ala Phe Ile Gly
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 301
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 301

Val Asp Asn Lys Phe Asn Lys Glu Gly Phe Tyr Ala Ala Leu Glu Ile
1               5                   10                  15

Val Ser Leu Pro Asn Leu Thr Pro Arg Gln Arg Gly Ala Phe Ile Ser
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 302
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 302

Val Asp Asn Lys Phe Asn Lys Glu Gly Phe Tyr Ala Ala Ile Glu Ile
1               5                   10                  15

Val Ser Leu Pro Asn Leu Asn Arg Arg Gln Arg Glu Ala Phe Ile Thr
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 303

```
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 303

Val Asp Asn Lys Phe Asn Lys Glu Gly Phe Tyr Ala Ala Leu Glu Ile
1               5                   10                  15

Leu Thr Leu Pro Asn Leu Thr Gly Arg Gln Arg Thr Ala Phe Ile Arg
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 304
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 304

Val Asp Asn Lys Phe Asn Lys Glu Gly Phe Tyr Ala Ala Ile Glu Ile
1               5                   10                  15

Leu Val Leu Pro Asn Leu Asn Asn Lys Gln Arg Ser Ala Phe Ile Lys
            20                  25                  30

Ser Leu Asp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 305
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 305

Val Asp Asn Lys Phe Asn Lys Glu Gly Phe Tyr Ala Ala Ile Glu Ile
1               5                   10                  15

Leu Thr Leu Pro Asn Leu Thr Ser Arg Gln His Arg Ala Phe Ile Ala
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 306
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 306

Val Asp Asn Lys Phe Asn Lys Glu Gly Phe Tyr Ala Ala Leu Glu Ile
1               5                   10                  15

Ile Thr Leu Pro Asn Leu Asn Gln Arg Gln Arg Gln Ala Phe Ile Ala
            20                  25                  30
```

-continued

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 307
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 307

Val Asp Asn Lys Phe Asn Lys Glu Gly Phe Tyr Ala Ala Leu Glu Ile
1               5                   10                  15

Leu Ile Leu Pro Asn Leu Thr Gln Lys Gln Arg Gly Ala Phe Ile Ser
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 308
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 308

Val Asp Asn Lys Phe Asn Lys Glu Gly Phe Tyr Ala Ala Met Glu Ile
1               5                   10                  15

Ile Ile Leu Pro Asn Leu Thr Pro Arg Gln Arg Ala Ala Phe Ile Thr
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 309
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 309

Val Asp Asn Lys Phe Asn Lys Glu Gly Phe Tyr Ala Ala Ile Glu Ile
1               5                   10                  15

Leu Val Leu Pro Asn Leu Asn Ser Lys Gln Arg Thr Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 310
<211> LENGTH: 58
<212> TYPE: PRT
<213> ORGANISM: Artificial Sequence
<220> FEATURE:
<223> OTHER INFORMATION: Engineered IGF-1R binding polypeptide -continued

```
<400> SEQUENCE: 310

Val Asp Asn Lys Phe Asn Lys Glu Gly Phe Tyr Ala Ala Val Glu Ile
1               5                   10                  15

Leu Gly Leu Pro Asn Leu Asn Arg Lys Gln Arg Ser Ala Phe Ile Ala
            20                  25                  30

Ser Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 311
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 311

Val Asp Asn Lys Phe Asn Lys Glu Gly Phe Tyr Ala Ala Ile Glu Ile
1               5                   10                  15

Leu Ala Leu Pro Asn Leu Asn Gly Gly Gln Arg Ser Ala Phe Ile Arg
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 312
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 312

Val Asp Asn Lys Phe Asn Lys Glu Gly Phe Tyr Ala Ala Ile Glu Ile
1               5                   10                  15

Leu Thr Leu Pro Asn Leu Thr Asn Lys Gln Arg Arg Ala Phe Ile Gly
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 313
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 313

Val Asp Asn Lys Phe Asn Lys Glu Gly Phe Tyr Ala Ala Leu Glu Ile
1               5                   10                  15

Leu Ile Leu Pro Asn Leu Asn Asp Arg Gln Arg Arg Ala Phe Ile Gly
            20                  25                  30

Ser Leu Asn Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 314
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 314

Val Asp Asn Lys Phe Asn Lys Glu Gly Phe Tyr Ala Ala Leu Glu Ile
1               5                   10                  15

Val Thr Leu Pro Asn Leu Asn Pro Lys Gln Arg Ser Ala Phe Ile Ser
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 315
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 315

Val Asp Asn Lys Phe Asn Lys Glu Gly Phe Tyr Ala Ala Ile Glu Ile
1               5                   10                  15

Leu Ser Leu Pro Asn Leu Asn Ser Arg Gln Arg Gln Ala Phe Ile Gly
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 316
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 316

Val Asp Asn Lys Phe Asn Lys Glu Gly Phe Tyr Ala Ala Leu Glu Ile
1               5                   10                  15

Val Ile Leu Pro Asn Leu Asn Thr Arg Gln Arg Asp Ala Phe Ile Arg
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 317
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 317

Val Asp Asn Lys Phe Asn Lys Glu Gly Phe Tyr Ala Ala Ile Glu Ile
1               5                   10                  15

Val Ser Leu Pro Asn Leu Asn Gln Arg Gln Arg Thr Ala Phe Ile Ser

```
                    20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 318
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 318

Val Asp Asn Lys Phe Asn Lys Glu Gly Phe Tyr Ala Gly Ile Glu Ile
1               5                   10                  15

Ile Ala Leu Pro Asn Leu Asn Gln His Gln Arg Glu Ala Phe Ile Lys
            20                  25                  30

Ser Leu Asn Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 319
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 319

Val Asp Asn Lys Phe Asn Lys Glu Gly Phe Tyr Ala Ala Ile Glu Ile
1               5                   10                  15

Leu Ser Leu Pro Asn Leu Asn Ser Arg Gln His Arg Ala Phe Ile Thr
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 320
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 320

Val Asp Asn Lys Phe Asn Lys Glu Gly Phe Tyr Ala Ala Leu Glu Ile
1               5                   10                  15

Val Ser Leu Pro Asn Leu Asn Ser Arg Gln Arg Thr Ala Phe Ile Thr
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 321
<211> LENGTH: 58
<212> TYPE: PRT
<213> ORGANISM: Artificial Sequence
<220> FEATURE:
```

<223> OTHER INFORMATION: Engineered IGF-1R binding polypeptide

<400> SEQUENCE: 321

Val Asp Asn Lys Phe Asn Lys Glu Gly Phe Tyr Ala Leu Ile Glu Ile
1               5                   10                  15

Val Ser Leu Pro Asn Leu Asn His Lys Gln Arg Asn Ala Phe Ile Arg
            20                  25                  30

Ser Leu Asn Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 322
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 322

Val Asp Asn Lys Phe Asn Lys Glu Gly Phe Tyr Ala Ala Leu Glu Ile
1               5                   10                  15

Val Ala Leu Pro Asn Leu Asn Pro Arg Gln Arg Thr Ala Phe Ile Arg
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 323
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 323

Val Asp Asn Lys Phe Asn Lys Glu Gly Phe Tyr Ala Ala Ile Glu Ile
1               5                   10                  15

Leu Thr Leu Pro Asn Leu Asn Arg Arg Gln Arg Ser Ala Phe Ile Ala
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 324
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 324

Val Asp Asn Lys Phe Asn Lys Glu Gly Phe Tyr Ala Ala Leu Glu Ile
1               5                   10                  15

Val Gly Leu Pro Asn Leu Thr Gly Arg Gln Arg Thr Ala Phe Ile Gln
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys

-continued 50                  55

<210> SEQ ID NO 325
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 325

Val Asp Asn Lys Phe Asn Lys Glu Gly Phe Tyr Ala Ala Met Glu Ile
 1               5                  10                  15

Val Ala Leu Pro Asn Leu Asn Gly Arg Gln Arg Arg Ala Phe Ile Arg
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 326
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 326

Val Asp Asn Lys Phe Asn Lys Glu Gly Phe Tyr Ala Ala Ile Glu Ile
 1               5                  10                  15

Val Thr Leu Pro Asn Leu Thr Gly Asn Gln Arg Thr Ala Phe Ile Arg
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 327
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 327

Val Asp Asn Lys Phe Asn Lys Glu Gly Phe Tyr Ala Ala Leu Glu Ile
 1               5                  10                  15

Leu Thr Leu Pro Asn Leu Thr Arg His Gln Arg Thr Ala Phe Ile Asp
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 328
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 328

Val Asp Asn Lys Phe Asn Lys Glu Gly Phe Tyr Ala Ser Met Glu Ile
 1               5                  10                  15

```
Leu Ser Leu Pro Asn Leu Asn Gly Lys Gln Arg Thr Ala Phe Ile Thr
        20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 329
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 329

Val Asp Asn Lys Phe Asn Lys Glu Gly Phe Tyr Ala Ala Leu Glu Ile
1               5                   10                  15

Leu Thr Leu Pro Asn Leu Asn Thr Lys Gln Arg Thr Ala Phe Ile Gly
        20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 330
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 330

Val Asp Asn Lys Phe Asn Lys Glu Gly Phe Tyr Ala Ala Met Glu Ile
1               5                   10                  15

Val Ala Leu Pro Asn Leu Asn Arg Gln Gln Arg Thr Ala Phe Ile Asn
        20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 331
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 331

Val Asp Asn Lys Phe Asn Lys Glu Gly Phe Tyr Ala Ala Ile Glu Ile
1               5                   10                  15

Ile Ile Leu Pro Asn Leu Thr Pro Arg Gln Arg Ser Ala Phe Ile Asp
        20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 332
<211> LENGTH: 58
<212> TYPE: PRT
```

```
<213> ORGANISM: Artificial Sequence
<220> FEATURE:
<223> OTHER INFORMATION: Engineered IGF-1R binding polypeptide

<400> SEQUENCE: 332

Val Asp Asn Lys Phe Asn Lys Glu Gly Phe Tyr Ala Ala Met Glu Ile
1               5                   10                  15

Leu Gln Leu Pro Asn Leu Thr Asn Arg Gln Arg Ala Ala Phe Ile Ser
            20                  25                  30

Ser Leu Pro Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 333
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 333

Val Asp Asn Lys Phe Asn Lys Glu Gly Phe Tyr Ala Ala Ile Glu Ile
1               5                   10                  15

Leu Val Leu Pro Asn Leu Asn Gln Asp Gln Arg Thr Ala Phe Ile Thr
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 334
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 334

Val Asp Asn Lys Phe Asn Lys Glu Gly Phe Tyr Ala Ala Leu Glu Ile
1               5                   10                  15

Leu Ile Leu Pro Asn Leu Asn Ser Ser Gln Arg Thr Ala Phe Ile Gly
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 335
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 335

Val Asp Asn Lys Phe Asn Lys Glu Gly Phe Tyr Ala Ala Ile Glu Ile
1               5                   10                  15

Leu Ala Leu Pro Asn Leu Asn Thr Arg Gln His Arg Ala Phe Ile Arg
            20                  25                  30

Ser Leu Thr Asp Asp Pro Ser Gln Ser Ala Asn Leu Leu Ala Glu Ala
        35                  40                  45
```

```
Lys Lys Leu Asn Asp Ala Gln Ala Pro Lys
    50                  55
```

<210> SEQ ID NO 336
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 336

```
Val Asp Asn Lys Phe Asn Lys Glu Gly Phe Tyr Ala Ala Leu Glu Ile
1               5                   10                  15

Leu Val Leu Pro Asn Leu Asn His Lys Gln Arg Thr Ala Phe Ile Gly
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 337
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 337

```
Val Asp Asn Lys Phe Asn Lys Glu Gly Phe Tyr Ala Ala Ile Glu Ile
1               5                   10                  15

Leu Ser Leu Pro Asn Leu Thr Arg Arg Gln Arg Gly Ala Phe Ile Thr
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 338
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 338

```
Val Asp Asn Lys Phe Asn Lys Glu Gly Phe Tyr Ala Ala Ile Glu Ile
1               5                   10                  15

Ile Ser Leu Pro Asn Leu Asn Ala Arg Gln Arg Thr Ala Phe Ile Ala
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 339
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 339

Val Asp Asn Lys Phe Asn Lys Glu Gly Phe Tyr Ala Ala Ile Glu Ile
1               5                   10                  15

Leu Ala Leu Pro Asn Leu Asn Arg Thr Gln Arg Ser Ala Phe Ile Gly
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 340
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 340

Val Asp Asn Lys Phe Asn Lys Glu Gly Phe Tyr Ala Ala Ile Glu Ile
1               5                   10                  15

Ile Ser Leu Pro Asn Leu Asn Pro Arg Gln Arg Thr Ala Phe Ile Thr
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 341
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 341

Val Asp Asn Lys Phe Asn Lys Glu Gly Phe Tyr Ala Ala Ile Glu Ile
1               5                   10                  15

Leu Val Leu Pro Asn Leu Asn Lys Arg Gln Arg Ala Ala Phe Ile Gly
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 342
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 342

Val Asp Asn Lys Phe Asn Lys Glu Gly Phe Tyr Ala Ala Ile Glu Ile
1               5                   10                  15

Leu Ala Leu Pro Asn Leu Asn Arg Lys Gln Arg Thr Ala Phe Ile Gln
            20                  25                  30

Ser Leu Asp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 343

-continued

```
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 343

Val Asp Asn Lys Phe Asn Lys Glu Gly Phe Tyr Ala Ala Leu Glu Ile
 1               5                  10                  15

Ile Ser Leu Pro Asn Leu Thr Gln Arg Gln His Glu Ala Phe Ile Arg
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 344
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 344

Val Asp Asn Lys Phe Asn Lys Glu Gly Phe Tyr Ala Ala Ile Glu Ile
 1               5                  10                  15

Leu Thr Leu Pro Asn Leu Thr Gln Asn Gln His Thr Ala Phe Ile Arg
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 345
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 345

Val Asp Asn Lys Phe Asn Lys Glu Gly Phe Tyr Ala Ala Ile Glu Ile
 1               5                  10                  15

Leu Thr Leu Pro Asn Leu Asn Gln Lys Gln His Arg Ala Phe Ile Ala
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 346
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 346

Val Asp Asn Lys Phe Asn Lys Glu Gly Phe Tyr Ala Ala Met Glu Ile
 1               5                  10                  15

Val Ala Leu Pro Asn Leu Thr Ser Lys Gln Arg Thr Ala Phe Ile Arg
            20                  25                  30
```

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 347
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 347

Val Asp Asn Lys Phe Asn Lys Glu Gly Phe Tyr Ala Ala Ile Glu Ile
1               5                   10                  15

Leu Ile Leu Pro Asn Leu Asn Thr Arg Gln Arg Gly Ala Phe Ile Gly
            20                  25                  30

Ser Leu Asn Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 348
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 348

Val Asp Asn Lys Phe Asn Lys Glu Gly Phe Tyr Ala Ala Ile Glu Ile
1               5                   10                  15

Leu Ser Leu Pro Asn Leu Asn Arg Arg Gln Arg Ser Ala Phe Ile Ser
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 349
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 349

Val Asp Asn Lys Phe Asn Lys Glu Gly Phe Tyr Ala Ala Leu Glu Ile
1               5                   10                  15

Leu Ser Leu Pro Asn Leu Thr Lys Lys Gln Arg Thr Ala Phe Ile Arg
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 350
<211> LENGTH: 58
<212> TYPE: PRT
<213> ORGANISM: Artificial Sequence
<220> FEATURE:
<223> OTHER INFORMATION: Engineered IGF-1R binding polypeptide

```
<400> SEQUENCE: 350

Val Asp Asn Lys Phe Asn Lys Glu Gly Phe Tyr Ala Ala Leu Glu Ile
1               5                   10                  15

Leu Thr Leu Pro Asn Leu Asn Gln Asn Gln Arg Ser Ala Phe Ile Arg
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 351
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 351

Val Asp Asn Lys Phe Asn Lys Glu Gly Phe Tyr Ala Ala Ile Glu Ile
1               5                   10                  15

Leu Thr Leu Pro Asn Leu Asn Ser Pro Gln Arg Asp Ala Phe Ile Ser
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 352
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 352

Val Asp Asn Lys Phe Asn Lys Glu Gly Phe Tyr Ala Ala Ile Glu Ile
1               5                   10                  15

Ile Thr Leu Pro Asn Leu Thr Gln Gly Gln Arg Thr Ala Phe Ile Arg
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 353
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 353

Val Asp Asn Lys Phe Asn Lys Glu Gly Phe Tyr Ala Ala Met Glu Ile
1               5                   10                  15

Leu Ile Leu Pro Asn Leu Thr Arg Gly Gln Arg Arg Ala Phe Ile Ala
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 354
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 354

Val Asp Asn Lys Phe Asn Lys Glu Gly Phe Tyr Ala Ala Met Glu Ile
1               5                   10                  15

Leu Thr Leu Pro Asn Leu Asn Gln Lys Gln Arg Asp Ala Phe Ile Thr
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 355
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 355

Val Asp Asn Lys Phe Asn Lys Glu Gly Phe Tyr Ala Ala Met Glu Ile
1               5                   10                  15

Leu Thr Leu Pro Asn Leu Asn Lys Arg Gln Arg Thr Ala Phe Ile Glu
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 356
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 356

Val Asp Asn Lys Phe Asn Lys Glu Gly Phe Tyr Ala Ala Ile Glu Ile
1               5                   10                  15

Ile Ala Leu Pro Asn Leu Thr Arg Arg Gln Arg Thr Ala Phe Ile Thr
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 357
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 357

Val Asp Asn Lys Phe Asn Lys Glu Gly Phe Tyr Ala Ala Ile Glu Ile
1               5                   10                  15

Val Thr Leu Pro Asn Leu Thr His Arg Gln Arg Ser Ala Phe Ile Gly

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
 50                  55

<210> SEQ ID NO 358
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 358

Val Asp Asn Lys Phe Asn Lys Glu Gly Phe Tyr Ala Ala Met Glu Ile
 1               5                  10                  15

Leu Thr Leu Pro Asn Leu Asn Gln Arg Gln Arg Thr Ala Phe Ile Thr
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
 50                  55

<210> SEQ ID NO 359
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 359

Val Asp Asn Lys Phe Asn Lys Glu Gly Phe Tyr Ala Ala Leu Glu Ile
 1               5                  10                  15

Ile Thr Leu Pro Asn Leu Thr Gln Arg Gln Arg Ser Ala Phe Ile Asn
            20                  25                  30

Ser Leu Pro Asp Asp Pro Ser Gln Ser Ala Asn Leu Leu Ala Glu Ala
        35                  40                  45

Lys Lys Leu Asn Asp Ala Gln Ala Pro Lys
 50                  55

<210> SEQ ID NO 360
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 360

Val Asp Asn Lys Phe Asn Lys Glu Gly Phe Tyr Ala Ala Ile Glu Ile
 1               5                  10                  15

Leu Thr Leu Pro Asn Leu Thr Gly Arg Gln Arg Thr Ala Phe Ile Arg
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
 50                  55

<210> SEQ ID NO 361
<211> LENGTH: 58
<212> TYPE: PRT
<213> ORGANISM: Artificial Sequence
<220> FEATURE:

<223> OTHER INFORMATION: Engineered IGF-1R binding polypeptide

<400> SEQUENCE: 361

Val Asp Asn Lys Phe Asn Lys Glu Gly Phe Tyr Ala Ala Ile Glu Ile
1               5                   10                  15

Ile Ser Leu Pro Asn Leu Thr Arg Arg Gln Arg Ala Ala Phe Ile Arg
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 362
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 362

Val Asp Asn Lys Phe Asn Lys Glu Gly Phe Tyr Ala Ala Ile Glu Ile
1               5                   10                  15

Val Ser Leu Pro Asn Leu Thr Ser Lys Gln Arg Gly Ala Phe Ile Thr
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 363
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 363

Val Asp Asn Lys Phe Asn Lys Glu Gly Phe Tyr Ala Ala Ile Glu Ile
1               5                   10                  15

Val Ser Leu Pro Asn Leu Thr Gln Arg Gln Arg Thr Ala Phe Ile Thr
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 364
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 364

Val Asp Asn Lys Phe Asn Lys Glu Gly Phe Tyr Ala Ala Leu Glu Ile
1               5                   10                  15

Leu Ile Leu Pro Asn Leu Thr Gln His Gln Arg Thr Ala Phe Ile Thr
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys

<210> SEQ ID NO 365
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 365

```
Val Asp Asn Lys Phe Asn Lys Glu Gly Phe Tyr Ala Ala Ile Glu Ile
 1               5                  10                  15

Leu Thr Leu Pro Asn Leu Thr Ser Gln Gln Arg Arg Ala Phe Ile Thr
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 366
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 366

```
Val Asp Asn Lys Phe Asn Lys Glu Gly Phe Tyr Ala Ala Leu Glu Ile
 1               5                  10                  15

Ile Thr Leu Pro Asn Leu Asn Pro Arg Gln Arg Thr Ala Phe Ile Asn
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 367
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 367

```
Val Asp Asn Lys Phe Asn Lys Glu Gly Phe Tyr Ala Ala Met Glu Ile
 1               5                  10                  15

Leu Thr Leu Pro Asn Leu Asn Lys Arg Gln Arg Ser Ala Phe Ile Arg
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 368
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 368

```
Val Asp Asn Lys Phe Asn Lys Glu Gly Phe Tyr Ala Ala Ile Glu Ile
 1               5                  10                  15
```

Leu Val Leu Pro Asn Leu Asn Thr Gln Gln Arg Arg Ala Phe Ile Lys
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 369
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 369

Val Asp Asn Lys Phe Asn Lys Glu Gly Phe Tyr Ala Ala Leu Glu Ile
1               5                   10                  15

Val Ser Leu Pro Asn Leu Asn Thr Arg Gln Arg Ser Ala Phe Ile Thr
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 370
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 370

Val Asp Asn Lys Phe Asn Lys Glu Gly Phe Tyr Ala Ala Ile Glu Ile
1               5                   10                  15

Leu Val Leu Pro Asn Leu Asn Lys Arg Gln Arg Glu Ala Phe Ile Gly
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 371
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 371

Val Asp Asn Lys Phe Asn Lys Glu Gly Phe Tyr Ala Ala Met Glu Ile
1               5                   10                  15

Leu Val Leu Pro Asn Leu Asn Gln Lys Gln Arg Arg Ala Phe Ile Asn
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 372
<211> LENGTH: 58
<212> TYPE: PRT

<213> ORGANISM: Artificial Sequence
<220> FEATURE:
<223> OTHER INFORMATION: Engineered IGF-1R binding polypeptide

<400> SEQUENCE: 372

Val Asp Asn Lys Phe Asn Lys Glu Gly Phe Tyr Ala Ala Ile Glu Ile
1               5                   10                  15

Leu Thr Leu Pro Asn Leu Thr Arg Arg Gln Arg Ser Ala Phe Ile Thr
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 373
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 373

Val Asp Asn Lys Phe Asn Lys Glu Gly Phe Tyr Ala Ala Ile Glu Ile
1               5                   10                  15

Leu Ser Leu Pro Asn Leu Thr Gly Arg Gln His Arg Ala Phe Ile Thr
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 374
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 374

Val Asp Asn Lys Phe Asn Lys Glu Gly Phe Tyr Ala Ala Ile Glu Ile
1               5                   10                  15

Ile Ala Leu Pro Asn Leu Asn Arg Arg Gln Arg Ser Ala Phe Ile Arg
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 375
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 375

Val Asp Asn Lys Phe Asn Lys Glu Gly Phe Tyr Ala Ala Leu Glu Ile
1               5                   10                  15

Leu Val Leu Pro Asn Leu Thr Gly Arg Gln Arg Lys Ala Phe Ile Glu
            20                  25                  30

Ser Leu Pro Asp Asp Pro Ser Gln Ser Ala Asn Leu Leu Ala Glu Ala
        35                  40                  45

```
Lys Lys Leu Asn Asp Ala Gln Ala Pro Lys
     50                  55
```

<210> SEQ ID NO 376
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 376

```
Val Asp Asn Lys Phe Asn Lys Glu Gly Phe Tyr Ala Ala Ile Glu Ile
 1               5                  10                  15

Leu Thr Leu Pro Asn Leu Asn Ser Arg Gln Arg Thr Ala Phe Ile Gly
             20                  25                  30

Ser Leu Gly Asp Asp Pro Ser Gln Ser Ala Asn Leu Leu Ala Glu Ala
         35                  40                  45

Lys Lys Leu Asn Asp Ala Gln Ala Pro Lys
     50                  55
```

<210> SEQ ID NO 377
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 377

```
Val Asp Asn Lys Phe Asn Lys Glu Gly Phe Tyr Ala Ala Leu Glu Ile
 1               5                  10                  15

Leu Val Leu Pro Asn Leu Asn Pro Lys Gln Arg Thr Ala Phe Ile Asp
             20                  25                  30

Ser Leu Ser Asp Asp Pro Ser Gln Ser Ala Asn Leu Leu Ala Glu Ala
         35                  40                  45

Lys Lys Leu Asn Asp Ala Gln Ala Pro Lys
     50                  55
```

<210> SEQ ID NO 378
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 378

```
Val Asp Asn Lys Phe Asn Lys Glu Gly Phe Tyr Ala Ser Ile Glu Ile
 1               5                  10                  15

Leu Val Leu Pro Asn Leu Asn Gly Arg Gln Arg Thr Ala Phe Ile Thr
             20                  25                  30

Ser Leu Ala Asp Asp Pro Ser Gln Ser Ala Asn Leu Leu Ala Glu Ala
         35                  40                  45

Lys Lys Leu Asn Asp Ala Gln Ala Pro Lys
     50                  55
```

<210> SEQ ID NO 379
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 379

```
Val Asp Asn Lys Phe Asn Lys Glu Gly Phe Tyr Ala Ala Ile Glu Ile
 1               5                  10                  15

Leu Thr Leu Pro Asn Leu Asn Ser Arg Gln Arg Ala Phe Ile Gly
            20                  25                  30

Ser Leu Gln Asp Asp Pro Ser Gln Ser Ala Asn Leu Leu Ala Glu Ala
            35                  40                  45

Lys Lys Leu Asn Asp Ala Gln Ala Pro Lys
        50                  55
```

<210> SEQ ID NO 380
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 380

```
Val Asp Asn Lys Phe Asn Lys Glu Gly Phe Tyr Ala Ala Met Glu Ile
 1               5                  10                  15

Leu Thr Leu Pro Asn Leu Asn Arg Lys Gln Arg Ser Ala Phe Ile Gly
            20                  25                  30

Ser Leu Thr Asp Asp Pro Ser Gln Ser Ala Asn Leu Leu Ala Glu Ala
            35                  40                  45

Lys Lys Leu Asn Asp Ala Gln Ala Pro Lys
        50                  55
```

<210> SEQ ID NO 381
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 381

```
Val Asp Asn Lys Phe Asn Lys Glu Gly Phe Tyr Ala Ala Ile Glu Ile
 1               5                  10                  15

Leu Ile Leu Pro Asn Leu Asn Gln Arg Gln Arg Ser Ala Phe Ile Gly
            20                  25                  30

Ser Leu Glu Asp Asp Pro Ser Gln Ser Ala Asn Leu Leu Ala Glu Ala
            35                  40                  45

Lys Lys Leu Asn Asp Ala Gln Ala Pro Lys
        50                  55
```

<210> SEQ ID NO 382
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 382

```
Val Asp Asn Lys Phe Asn Lys Glu Gly Phe Tyr Ala Ala Ile Glu Ile
 1               5                  10                  15

Leu Ala Leu Pro Asn Leu Asn Arg Arg Gln Arg Ser Ala Phe Ile Asn
            20                  25                  30

Ser Leu Gly Asp Asp Pro Ser Gln Ser Ala Asn Leu Leu Ala Glu Ala
            35                  40                  45

Lys Lys Leu Asn Asp Ala Gln Ala Pro Lys
        50                  55
```

<210> SEQ ID NO 383

```
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 383

Val Asp Asn Lys Phe Asn Lys Glu Gly Phe Tyr Ala Ala Leu Glu Ile
 1               5                  10                  15

Val Ala Leu Pro Asn Leu Asn Arg Lys Gln Arg Thr Ala Phe Ile Ser
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 384
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 384

Val Asp Asn Lys Phe Asn Lys Glu Gly Phe Tyr Ala Ala Met Glu Ile

```
Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 387
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 387

Val Asp Asn Lys Phe Asn Lys Glu Gly Phe Tyr Ala Ala Leu Glu Ile
1               5                   10                  15

Leu Val Leu Pro Asn Leu Thr Gly Asn Gln Arg Thr Ala Phe Ile Thr
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 388
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 388

Val Asp Asn Lys Phe Asn Lys Glu Gly Phe Tyr Ala Ala Leu Glu Ile
1               5                   10                  15

Ile Ala Leu Pro Asn Leu Asn Gln Lys Gln Arg Ser Ala Phe Ile Gln
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 389
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 389

Val Asp Asn Lys Phe Asn Lys Glu Gly Phe Tyr Ala Ala Ile Glu Ile
1               5                   10                  15

Leu Val Leu Pro Asn Leu Asn Ser Arg Gln Arg Asp Ala Phe Ile Arg
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 390
<211> LENGTH: 58
<212> TYPE: PRT
<213> ORGANISM: Artificial Sequence
<220> FEATURE:
<223> OTHER INFORMATION: Engineered IGF-1R binding polypeptide
```

```
<400> SEQUENCE: 390

Val Asp Asn Lys Phe Asn Lys Glu Gly Phe Tyr Ala Ala Leu Glu Ile
1               5                   10                  15

Leu Ile Leu Pro Asn Leu Asn Gln Gly Gln Arg Asp Ala Phe Ile Thr
            20                  25                  30

Ser Leu Gly Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 391
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 391

Val Asp Asn Lys Phe Asn Lys Glu Gly Phe Tyr Ala Ala Met Glu Ile
1               5                   10                  15

Leu Ile Leu Pro Asn Leu Thr Arg Arg Gln His Arg Ala Phe Ile Thr
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 392
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 392

Val Asp Asn Lys Phe Asn Lys Glu Gly Phe Tyr Ala Ala Leu Glu Ile
1               5                   10                  15

Leu Ser Leu Pro Asn Leu Thr Pro Lys Gln Arg Ser Ala Phe Ile Thr
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 393
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 393

Val Asp Asn Lys Phe Asn Lys Glu Gly Phe Tyr Ala Ala Ile Glu Ile
1               5                   10                  15

Val Val Leu Pro Asn Leu Thr Pro Arg Gln Arg Ser Ala Phe Ile Lys
            20                  25                  30

Ser Leu Asp Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 394
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 394

Val Asp Asn Lys Phe Asn Lys Glu Gly Phe Tyr Ala Ala Ile Glu Ile
1               5                   10                  15

Leu Thr Leu Pro Asn Leu Asn Pro Gln Gln Arg Thr Ala Phe Ile Lys
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 395
<211> LENGTH: 58
<212> TYPE: PRT
<213> ORGANISM: Artificial Sequence
<220> FEATURE:
<223> OTHER INFORMATION: Engineered IGF-1R binding polypeptide

<400> SEQUENCE: 395

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 396
<211> LENGTH: 1367
<212> TYPE: PRT
<213> ORGANISM: Homo Sapiens

<400> SEQUENCE: 396

Met Lys Ser Gly Ser Gly Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile

```
                145                 150                 155                 160
Leu Asp Ala Val Ser Asn Asn Tyr Ile Val Gly Asn Lys Pro Pro Lys
                    165                 170                 175
Glu Cys Gly Asp Leu Cys Pro Gly Thr Met Glu Lys Pro Met Cys
                180                 185                 190
Glu Lys Thr Thr Ile Asn Asn Glu Tyr Asn Tyr Arg Cys Trp Thr Thr
                195                 200                 205
Asn Arg Cys Gln Lys Met Cys Pro Ser Thr Cys Gly Arg Ala Cys
                210                 215                 220
Thr Glu Asn Asn Glu Cys Cys His Pro Glu Cys Leu Gly Ser Cys Ser
225                 230                 235                 240
Ala Pro Asp Asn Asp Thr Ala Cys Val Ala Cys Arg His Tyr Tyr Tyr
                    245                 250                 255
Ala Gly Val Cys Val Pro Ala Cys Pro Pro Asn Thr Tyr Arg Phe Glu
                260                 265                 270
Gly Trp Arg Cys Val Asp Arg Asp Phe Cys Ala Asn Ile Leu Ser Ala
                275                 280                 285
Glu Ser Ser Asp Ser Glu Gly Phe Val Ile His Asp Gly Glu Cys Met
                290                 295                 300
Gln Glu Cys Pro Ser Gly Phe Ile Arg Asn Gly Ser Gln Ser Met Tyr
305                 310                 315                 320
Cys Ile Pro Cys Glu Gly Pro Cys Pro Lys Val Cys Glu Glu Lys
                    325                 330                 335
Lys Thr Lys Thr Ile Asp Ser Val Thr Ser Ala Gln Met Leu Gln Gly
                340                 345                 350
Cys Thr Ile Phe Lys Gly Asn Leu Leu Ile Asn Ile Arg Arg Gly Asn
                355                 360                 365
Asn Ile Ala Ser Glu Leu Glu Asn Phe Met Gly Leu Ile Glu Val Val
                370                 375                 380
Thr Gly Tyr Val Lys Ile Arg His Ser His Ala Leu Val Ser Leu Ser
385                 390                 395                 400
Phe Leu Lys Asn Leu Arg Leu Ile Leu Gly Glu Glu Gln Leu Glu Gly
                    405                 410                 415
Asn Tyr Ser Phe Tyr Val Leu Asp Asn Gln Asn Leu Gln Gln Leu Trp
                420                 425                 430
Asp Trp Asp His Arg Asn Leu Thr Ile Lys Ala Gly Lys Met Tyr Phe
                435                 440                 445
Ala Phe Asn Pro Lys Leu Cys Val Ser Glu Ile Tyr Arg Met Glu Glu
                450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Asp Val Leu His Phe Thr
                    485                 490                 495
Ser Thr Thr Thr Ser Lys Asn Arg Ile Ile Ile Thr Trp His Arg Tyr
                500                 505                 510
Arg Pro Pro Asp Tyr Arg Asp Leu Ile Ser Phe Thr Val Tyr Tyr Lys
                515                 520                 525
Glu Ala Pro Phe Lys Asn Val Thr Glu Tyr Asp Gly Gln Asp Ala Cys
                530                 535                 540
Gly Ser Asn Ser Trp Asn Met Val Asp Val Asp Leu Pro Pro Asn Lys
545                 550                 555                 560
Asp Val Glu Pro Gly Ile Leu Leu His Gly Leu Lys Pro Trp Thr Gln
                    565                 570                 575
```

-continued

```
Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
        595                 600                 605

Ser Val Pro Ser Ile Pro Leu Asp Val Leu Ser Ala Ser Asn Ser Ser
610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
        675                 680                 685

Thr Glu Val Cys Gly Gly Glu Lys Gly Pro Cys Cys Ala Cys Pro Lys
    690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
        755                 760                 765

Glu Glu Leu Glu Thr Glu Tyr Pro Phe Phe Glu Ser Arg Val Asp Asn
    770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
    850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
        915                 920                 925

Gly Tyr Glu Asn Phe Ile His Leu Ile Ile Ala Leu Pro Val Ala Val
    930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
            980                 985                 990

Glu Val Ala Arg Glu Lys Ile Thr Met Ser Arg Glu Leu Gly Gln Gly
        995                 1000                1005
```

Ser Phe Gly Met Val Tyr Glu Gly Val Ala Lys Gly Val Lys Asp
    1010                1015                1020

Glu Pro Glu Thr Arg Val Ala Ile Lys Thr Val Asn Glu Ala Ser
1025                1030                1035                1040

Met Arg Glu Arg Ile Glu Phe Leu Asn Glu Ala Ser Val Met Lys Glu
                1045                1050                1055

Phe Asn Cys His His Val Val Arg Leu Leu Gly Val Val Ser Gln Gly
            1060                1065                1070

Gln Pro Thr Leu Val Ile Met Glu Leu Met Thr Arg Gly Asp Leu Lys
            1075                1080                1085

Ser Tyr Leu Arg Ser Leu Arg Pro Glu Met Glu Asn Asn Pro Val Leu
    1090                1095                1100

Ala Pro Pro Ser Leu Ser Lys Met Ile Gln Met Ala Gly Glu Ile Ala
1105                1110                1115                1120

Asp Gly Met Ala Tyr Leu Asn Ala Asn Lys Phe Val His Arg Asp Leu
            1125                1130                1135

Ala Ala Arg Asn Cys Met Val Ala Glu Asp Phe Thr Val Lys Ile Gly
            1140                1145                1150

Asp Phe Gly Met Thr Arg Asp Ile Tyr Glu Thr Asp Tyr Tyr Arg Lys
    1155                1160                1165

Gly Gly Lys Gly Leu Leu Pro Val Arg Trp Met Ser Pro Glu Ser Leu
1170                1175                1180

Lys Asp Gly Val Phe Thr Thr Tyr Ser Asp Val Trp Ser Phe Gly Val
1185                1190                1195                1200

Val Leu Trp Glu Ile Ala Thr Leu Ala Glu Gln Pro Tyr Gln Gly Leu
            1205                1210                1215

Ser Asn Glu Gln Val Leu Arg Phe Val Met Glu Gly Gly Leu Leu Asp
            1220                1225                1230

Lys Pro Asp Asn Cys Pro Asp Met Leu Phe Glu Leu Met Arg Met Cys
1235                1240                1245

Trp Gln Tyr Asn Pro Lys Met Arg Pro Ser Phe Leu Glu Ile Ile Ser
    1250                1255                1260

Ser Ile Lys Glu Glu Met Glu Pro Gly Phe Arg Glu Val Ser Phe Tyr
1265                1270                1275                1280

Tyr Ser Glu Glu Asn Lys Leu Pro Glu Pro Glu Glu Leu Asp Leu Glu
            1285                1290                1295

Pro Glu Asn Met Glu Ser Val Pro Leu Asp Pro Ser Ala Ser Ser Ser
            1300                1305                1310

Ser Leu Pro Leu Pro Asp Arg His Ser Gly His Lys Ala Glu Asn Gly
    1315                1320                1325

Pro Gly Pro Gly Val Leu Val Leu Arg Ala Ser Phe Asp Glu Arg Gln
    1330                1335                1340

Pro Tyr Ala His Met Asn Gly Gly Arg Lys Asn Glu Arg Ala Leu Pro
1345                1350                1355                1360

Leu Pro Gln Ser Ser Thr Cys
                1365

<210> SEQ ID NO 397
<211> LENGTH: 901
<212> TYPE: PRT
<213> ORGANISM: Homo sapiens

<400> SEQUENCE: 397

Glu Ile Cys Gly Pro Gly Ile Asp Ile Arg Asn Asp Tyr Gln Gln Leu
1               5                   10                  15

Lys Arg Leu Glu Asn Cys Thr Val Ile Glu Gly Tyr Leu His Ile Leu
            20                  25                  30

Leu Ile Ser Lys Ala Glu Asp Tyr Arg Ser Tyr Arg Phe Pro Lys Leu
            35                  40                  45

Thr Val Ile Thr Glu Tyr Leu Leu Phe Arg Val Ala Gly Leu Glu
50                      55                  60

Ser Leu Gly Asp Leu Phe Pro Asn Leu Thr Val Ile Arg Gly Trp Lys
65                  70                  75                  80

Leu Phe Tyr Asn Tyr Ala Leu Val Ile Phe Glu Met Thr Asn Leu Lys
                85                  90                  95

Asp Ile Gly Leu Tyr Asn Leu Arg Asn Ile Thr Arg Gly Ala Ile Arg
            100                 105                 110

Ile Glu Lys Asn Ala Asp Leu Cys Tyr Leu Ser Thr Val Asp Trp Ser
            115                 120                 125

Leu Ile Leu Asp Ala Val Ser Asn Asn Tyr Ile Val Gly Asn Lys Pro
130                 135                 140

Pro Lys Glu Cys Gly Asp Leu Cys Pro Gly Thr Met Glu Glu Lys Pro
145                 150                 155                 160

Met Cys Glu Lys Thr Thr Ile Asn Asn Glu Tyr Asn Tyr Arg Cys Trp
            165                 170                 175

Thr Thr Asn Arg Cys Gln Lys Met Cys Pro Ser Thr Cys Gly Lys Arg
            180                 185                 190

Ala Cys Thr Glu Asn Asn Glu Cys Cys His Pro Glu Cys Leu Gly Ser
            195                 200                 205

Cys Ser Ala Pro Asp Asn Asp Thr Ala Cys Val Ala Cys Arg His Tyr
210                 215                 220

Tyr Tyr Ala Gly Val Cys Val Pro Ala Cys Pro Pro Asn Thr Tyr Arg
225                 230                 235                 240

Phe Glu Gly Trp Arg Cys Val Asp Arg Asp Phe Cys Ala Asn Ile Leu
            245                 250                 255

Ser Ala Glu Ser Ser Asp Ser Glu Gly Phe Val Ile His Asp Gly Glu
            260                 265                 270

Cys Met Gln Glu Cys Pro Ser Gly Phe Ile Arg Asn Gly Ser Gln Ser
            275                 280                 285

Met Tyr Cys Ile Pro Cys Glu Gly Pro Cys Pro Lys Val Cys Glu Glu
            290                 295                 300

Glu Lys Lys Thr Lys Thr Ile Asp Ser Val Thr Ser Ala Gln Met Leu
305                 310                 315                 320

Gln Gly Cys Thr Ile Phe Lys Gly Asn Leu Leu Ile Asn Ile Arg Arg
            325                 330                 335

Gly Asn Asn Ile Ala Ser Glu Leu Glu Asn Phe Met Gly Leu Ile Glu
            340                 345                 350

Val Val Thr Gly Tyr Val Lys Ile Arg His Ser His Ala Leu Val Ser
            355                 360                 365

Leu Ser Phe Leu Lys Asn Leu Arg Leu Ile Leu Gly Glu Glu Gln Leu
            370                 375                 380

Glu Gly Asn Tyr Ser Phe Tyr Val Leu Asp Asn Gln Asn Leu Gln Gln
385                 390                 395                 400

Leu Trp Asp Trp Asp His Arg Asn Leu Thr Ile Lys Ala Gly Lys Met
                405                 410                 415

Tyr Phe Ala Phe Asn Pro Lys Leu Cys Val Ser Glu Ile Tyr Arg Met
            420                 425                 430

Glu Glu Val Thr Gly Thr Lys Gly Arg Gln Ser Lys Gly Asp Ile Asn

-continued

```
            435                 440                 445
Thr Arg Asn Asn Gly Glu Arg Ala Ser Cys Glu Ser Asp Val Leu His
        450                 455                 460

Phe Thr Ser Thr Thr Thr Ser Lys Asn Arg Ile Ile Ile Thr Trp His
465                 470                 475                 480

Arg Tyr Arg Pro Pro Asp Tyr Arg Asp Leu Ile Ser Phe Thr Val Tyr
                        485                 490                 495

Tyr Lys Glu Ala Pro Phe Lys Asn Val Thr Glu Tyr Asp Gly Gln Asp
                500                 505                 510

Ala Cys Gly Ser Asn Ser Trp Asn Met Val Asp Val Asp Leu Pro Pro
            515                 520                 525

Asn Lys Asp Val Glu Pro Gly Ile Leu Leu His Gly Leu Lys Pro Trp
        530                 535                 540

Thr Gln Tyr Ala Val Tyr Val Lys Ala Val Thr Leu Thr Met Val Glu
545                 550                 555                 560

Asn Asp His Ile Arg Gly Ala Lys Ser Glu Ile Leu Tyr Ile Arg Thr
                        565                 570                 575

Asn Ala Ser Val Pro Ser Ile Pro Leu Asp Val Leu Ser Ala Ser Asn
                580                 585                 590

Ser Ser Ser Gln Leu Ile Val Lys Trp Asn Pro Pro Ser Leu Pro Asn
            595                 600                 605

Gly Asn Leu Ser Tyr Tyr Ile Val Arg Trp Gln Arg Gln Pro Gln Asp
        610                 615                 620

Gly Tyr Leu Tyr Arg His Asn Tyr Cys Ser Lys Asp Lys Ile Pro Ile
625                 630                 635                 640

Arg Lys Tyr Ala Asp Gly Thr Ile Asp Ile Glu Glu Val Thr Glu Asn
                        645                 650                 655

Pro Lys Thr Glu Val Cys Gly Gly Glu Lys Gly Pro Cys Cys Ala Cys
                660                 665                 670

Pro Lys Thr Glu Ala Glu Lys Gln Ala Glu Lys Glu Glu Ala Glu Tyr
            675                 680                 685

Arg Lys Val Phe Glu Asn Phe Leu His Asn Ser Ile Phe Val Pro Arg
        690                 695                 700

Pro Glu Arg Lys Arg Arg Asp Val Met Gln Val Ala Asn Thr Thr Met
705                 710                 715                 720

Ser Ser Arg Ser Arg Asn Thr Thr Ala Ala Asp Thr Tyr Asn Ile Thr
                        725                 730                 735

Asp Pro Glu Glu Leu Glu Thr Glu Tyr Pro Phe Phe Glu Ser Arg Val
                740                 745                 750

Asp Asn Lys Glu Arg Thr Val Ile Ser Asn Leu Arg Pro Phe Thr Leu
            755                 760                 765

Tyr Arg Ile Asp Ile His Ser Cys Asn His Glu Ala Glu Lys Leu Gly
        770                 775                 780

Cys Ser Ala Ser Asn Phe Val Phe Ala Arg Thr Met Pro Ala Glu Gly
785                 790                 795                 800

Ala Asp Asp Ile Pro Gly Pro Val Thr Trp Glu Pro Arg Pro Glu Asn
                        805                 810                 815

Ser Ile Phe Leu Lys Trp Pro Glu Pro Glu Asn Pro Asn Gly Leu Ile
                820                 825                 830

Leu Met Tyr Glu Ile Lys Tyr Gly Ser Gln Val Glu Asp Gln Arg Glu
            835                 840                 845

Cys Val Ser Arg Gln Glu Tyr Arg Lys Tyr Gly Gly Ala Lys Leu Asn
        850                 855                 860
```

-continued

```
Arg Leu Asn Pro Gly Asn Tyr Thr Ala Arg Ile Gln Ala Thr Ser Leu
865                 870                 875                 880

Ser Gly Asn Gly Ser Trp Thr Asp Pro Val Phe Phe Tyr Val Gln Ala
                885                 890                 895

Lys Thr Gly Tyr Glu
            900

<210> SEQ ID NO 398
<211> LENGTH: 29
<212> TYPE: PRT
<213> ORGANISM: Artificial Sequence
<220> FEATURE:
<223> OTHER INFORMATION: Engineered IGF-1R Binding Polypeptide
<220> FEATURE:
<223> OTHER INFORMATION: Xaa at position 2  is G, P, or K.
<220> FEATURE:
<223> OTHER INFORMATION: Xaa at position 3  is F or Y.
<220> FEATURE:
<223> OTHER INFORMATION: Xaa at position 4 is Y or F.
<220> FEATURE:
<223> OTHER INFORMATION: Xaa at position 6 is A, L, S or G.
<220> FEATURE:
<223> OTHER INFORMATION: Xaa at position 7 is I, L, M or V.
<220> FEATURE:
<223> OTHER INFORMATION: Xaa at position 10 is I, L, or V.
<220> FEATURE:
<223> OTHER INFORMATION: Xaa at position 11 is T, A, S, G, L, Q, I or V.
<220> FEATURE:
<223> OTHER INFORMATION: Xaa at position 16 is N or T.
<220> FEATURE:
<223> OTHER INFORMATION: Xaa at position 17 is S, Q, H, R, N, K, P, A,
      D, E, G, or T.
<220> FEATURE:
<223> OTHER INFORMATION: Xaa at position 18 is S, Q, H, R, N, K, D, P, T
      or G.
<220> FEATURE:
<223> OTHER INFORMATION: Xaa at position 20 is S, Q, H, R, or W.
<220> FEATURE:
<223> OTHER INFORMATION: Xaa at position 21 is T, G, R, A, N, D, Q, E,
      K, or S.
<220> FEATURE:
<223> OTHER INFORMATION: Xaa at position 25 is T, G, R, A, N, D, Q, E,
      K, H, or S.
<220> FEATURE:
<223> OTHER INFORMATION: Xaa at position 28 is E, N, G, S, A, T, K, P,
      Q, or D.

<400> SEQUENCE: 398

Glu Xaa Xaa Xaa Ala Xaa Xaa Glu Ile Xaa Xaa Leu Pro Asn Leu Xaa
1               5                   10                  15

Xaa Xaa Gln Xaa Xaa Ala Phe Ile Xaa Ser Leu Xaa Asp
            20                  25

<210> SEQ ID NO 399
<211> LENGTH: 29
<212> TYPE: PRT
<213> ORGANISM: Artificial Sequence
<220> FEATURE:
<223> OTHER INFORMATION: Engineered IGF-1R Binding Polypeptide
<220> FEATURE:
<221> NAME/KEY: BINDING
<222> LOCATION: (7)...(8)
<223> OTHER INFORMATION: IGF-1 R binding motif located between positions
      7 and 8.

<400> SEQUENCE: 399

Ala Asp Asn Asn Phe Asn Lys Asp Pro Ser Gln Ser Ala Asn Leu Leu
1               5                   10                  15

Ser Glu Ala Lys Lys Leu Asn Glu Ser Gln Ala Pro Lys
            20                  25
```

```
<210> SEQ ID NO 400
<211> LENGTH: 29
<212> TYPE: PRT
<213> ORGANISM: Artificial Sequence
<220> FEATURE:
<223> OTHER INFORMATION: Engineered IGF-1R Binding Polypeptide
<220> FEATURE:
<221> NAME/KEY: BINDING
<222> LOCATION: (7)...(8)
<223> OTHER INFORMATION: IGF-1 R binding motif located between positions
      7 and 8.

<400> SEQUENCE: 400

Ala Asp Asn Lys Phe Asn Lys Asp Pro Ser Gln Ser Ala Asn Leu Leu
1               5                   10                  15

Ala Glu Ala Lys Lys Leu Asn Asp Ala Gln Ala Pro Lys
            20                  25

<210> SEQ ID NO 401
<211> LENGTH: 29
<212> TYPE: PRT
<213> ORGANISM: Artificial Sequence
<220> FEATURE:
<223> OTHER INFORMATION: Engineered IGF-1R Binding Polypeptide
<220> FEATURE:
<221> NAME/KEY: BINDING
<222> LOCATION: (7)...(8)
<223> OTHER INFORMATION: IGF-1 R binding motif located between positions
      7 and 8.

<400> SEQUENCE: 401

Ala Asp Asn Lys Phe Asn Lys Asp Pro Ser Val Ser Lys Glu Ile Leu
1               5                   10                  15

Ala Glu Ala Lys Lys Leu Asn Asp Ala Gln Ala Pro Lys
            20                  25

<210> SEQ ID NO 402
<211> LENGTH: 32
<212> TYPE: PRT
<213> ORGANISM: Artificial Sequence
<220> FEATURE:
<223> OTHER INFORMATION: Engineered IGF-1R Binding Polypeptide
<220> FEATURE:
<221> NAME/KEY: BINDING
<222> LOCATION: (10)...(11)
<223> OTHER INFORMATION: IGF-1 R binding motif located between positions
      10 AND 11.

<400> SEQUENCE: 402

Ala Asp Ala Gln Gln Asn Asn Phe Asn Lys Asp Pro Ser Gln Ser Thr
1               5                   10                  15

Asn Val Leu Gly Glu Ala Lys Lys Leu Asn Glu Ser Gln Ala Pro Lys
            20                  25                  30

<210> SEQ ID NO 403
<211> LENGTH: 27
<212> TYPE: PRT
<213> ORGANISM: Artificial Sequence
<220> FEATURE:
<223> OTHER INFORMATION: Engineered IGF-1R Binding Polypeptide
<220> FEATURE:
<221> NAME/KEY: BINDING
<222> LOCATION: (5)...(6)
<223> OTHER INFORMATION: IGF-1 R binding motif located between positions
      5 AND 6.
```

```
<400> SEQUENCE: 403

Ala Gln His Asp Glu Asp Pro Ser Gln Ser Ala Asn Val Leu Gly Glu
1               5                   10                  15

Ala Gln Lys Leu Asn Asp Ser Gln Ala Pro Lys
            20                  25

<210> SEQ ID NO 404
<211> LENGTH: 29
<212> TYPE: PRT
<213> ORGANISM: Artificial Sequence
<220> FEATURE:
<223> OTHER INFORMATION: Engineered IGF-1R Binding Polypeptide
<220> FEATURE:
<221> NAME/KEY: BINDING
<222> LOCATION: (7)...(8)
<223> OTHER INFORMATION: IGF-1 R binding motif located between positions
      7 and 8.

<400> SEQUENCE: 404

Val Asp Asn Lys Phe Asn Lys Asp Pro Ser Gln Ser Ala Asn Leu Leu
1               5                   10                  15

Ala Glu Ala Lys Lys Leu Asn Asp Ala Gln Ala Pro Lys
            20                  25
```